US011242353B2

(12) United States Patent
Schaus et al.

(10) Patent No.: US 11,242,353 B2
(45) Date of Patent: Feb. 8, 2022

(54) HETEROCYCLIC LSF INHIBITORS AND THEIR USES

(71) Applicant: TRUSTEES OF BOSTON UNIVERSITY, Boston, MA (US)

(72) Inventors: Scott E. Schaus, Boston, MA (US); Ulla Hansen, Bedford, MA (US); John A. Kavouris, Cambridge, MA (US); Emily A. York, Allston, MA (US); Niranjana Pokharel, Brighton, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 17/155,547

(22) Filed: Jan. 22, 2021

(65) Prior Publication Data

US 2021/0230173 A1 Jul. 29, 2021

Related U.S. Application Data

(60) Provisional application No. 62/965,384, filed on Jan. 24, 2020.

(51) Int. Cl.
*C07D 491/056* (2006.01)
*A61P 35/00* (2006.01)

(52) U.S. Cl.
CPC .......... *C07D 491/056* (2013.01); *A61P 35/00* (2018.01)

(58) Field of Classification Search
CPC .............................. C07D 491/56; A61P 35/00
See application file for complete search history.

(56) References Cited

U.S. PATENT DOCUMENTS

| | | | |
|---|---|---|---|
| 6,713,462 B2 | 3/2004 | Metcalf et al. | |
| 7,081,256 B2 | 7/2006 | Kubota et al. | |
| 8,440,705 B2 | 5/2013 | Lindquist et al. | |
| 9,802,948 B2 | 10/2017 | Hansen et al. | |
| 9,815,845 B2 | 11/2017 | Hansen et al. | |
| 2003/0130505 A1 | 7/2003 | Zhi et al. | |
| 2007/0287706 A1 | 12/2007 | Dickinson, Jr. et al. | |
| 2009/0081183 A1 | 3/2009 | Margolis et al. | |
| 2010/0004277 A1 | 1/2010 | Bulawa et al. | |
| 2010/0105906 A1 | 4/2010 | Bissantz et al. | |
| 2013/0158035 A1 | 6/2013 | Hansen | |
| 2013/0324570 A1 | 12/2013 | Hansen et al. | |
| 2017/0107227 A1 | 4/2017 | Hansen et al. | |
| 2018/0051033 A1 | 2/2018 | Hansen et al. | |
| 2019/0152949 A1 | 5/2019 | Cyr et al. | |
| 2020/0039996 A1* | 2/2020 | Schaus | A61P 35/00 |

FOREIGN PATENT DOCUMENTS

| | | |
|---|---|---|
| CN | 101410384 A | 4/2009 |
| EP | 2433634 A2 | 3/2012 |
| WO | 199836641 A1 | 8/1998 |
| WO | 2003066630 A2 | 8/2003 |
| WO | 2007136592 A2 | 11/2007 |
| WO | 2011123427 A2 | 10/2011 |
| WO | 2013052465 A1 | 4/2013 |

OTHER PUBLICATIONS

Andrews et al., "A rapid micropreparation technique for extraction of DNA-binding proteins from limiting numbers of mammalian cells", Nucleic Acids Res, 19(9): 2499 (1991).
Arand et al., "In vivo control of CpG and non-CpG DNA methylation by DNA methyltransferases", PLoS Genet, 8(6): e1002750. (2012).
Bing et al., "Nfkappa B interacts with serum amyloid A3 enhancer factor to synergistically activate mouse serum amyloid A3 gene transcription." J Biol Chem., 275:31616-31623 (2000).
Bovolenta et al., "In vivo adminislialion of recombinant IL-2 to individuals infected by HIV down-modulates the binding and expression of the transcriptioni factors Ying-Yang-1 and leader binding protein-1/late simian virus 40 factor." J. Immunol., 163:6892-6897 (1999).
Bruni et al., "Fe65, a ligand of the Alzheimer's beta-amyloid precursor protein, blocks cell cycle progression by down-regulating thymidylate synthase expression." J Biol Chem, 277:35481-35488 (2002).
Chang et al., "Design and Synthesis of 2-(3-Benzo[b]thienyl)-6,7-methylenedioxyquinolin-4-one Analogues as Potent Antitumor Agents that Inhibit Tubulin Assembly." J. Med. Chem., 52:4883-4891 (2009).
Chin, H.G., et al., "Transcription factor LSF-DNMT1 complex dissociation by FQI1 leads to aberrant DNA methylation and gene expression." Oncotarget, 7(50): 83627-83640 (2016).
Delcuve et al., "Mitotic partitioning of transcription factors", J Cell Biochem, 105(1): 1-8 (2008).
Dillon et al., "The SET-domain protein superfamily: protein lysine methyltransferases", Genome Biol, 6(8): 227 (2005).
Drouin et al., "The ubiquitously expressed DNA-binding protein Late SV40 Factor binds Ig switch regions and represses class switching to IgA." J Immunol, 168:2847-2856 (2002).
Esteve, P.O., et al., Direct interaction between DNMT1 and G9a coordinates DNA and histone methylation during replication. Genes Dev, 20(22): 3089-103 (2006).
Fang, J., et al., "Purification and functional characterization of SET8, a nucleosomal histone H4-lysine 20-specific methyltransferase." Curr Biol, 12(13): 1086-99 (2002).
Gottesfeld, J.M., "Mitotic repression of the transcriptional machinery" Trends Biochemistry Science, 22(6): 197-202 (1997).
Grant, T.J., et al., "Antiproliferative small-molecule inhibitors of transcription factor LSF reveal oncogene addiction to LSF in hepatocellular carcinoma", Proc Natl Acad Sci U S A, 109(12): 4503-4508 (2012).

(Continued)

*Primary Examiner* — Tracy Vivlemore
*Assistant Examiner* — Ebenezer O Sackey
(74) *Attorney, Agent, or Firm* — Nixon Peabody LLP; Ronald Eisenstein; Ravinderjit Braich

(57) ABSTRACT

The present invention is directed to heterocyclic SV40 Factor (LSF) inhibitors and their uses. In some implementations, the present invention discloses small-molecule compounds of Formula (I). In some implementations, the compounds of Formula (I) are used in methods for inhibiting LSF in a subject. In some implementations, the compounds of Formula (I) are used in methods for treating cancer in a subject.

30 Claims, 3 Drawing Sheets

(56) References Cited

OTHER PUBLICATIONS

Guo, et al., "A polymorphism at the miR-502 binding site in the 3'-untranslated region of the histone methyltransferase SET8 is associated with hepatocellular carcinoma outcome." International Journal of Cancer,131(6): 1318-1322 (2012).
Haigh et al., "Small molecule shape-fingerprints." J. Chem. Inf. Model, 45:673-684 (2005).
Hansen et al., "Transcriptions factors LSF and E2Fs: Tandem cyclists driving G0 to S?" Cell Cycle, 8:2146-2151 (2009).
Hou, et al., "SET8 induces epithelialmesenchymal transition and enhances prostate cancer cell metastasis by cooperating with ZEB1." Mol Med Rep, 13(2): 1681-8 (2016).
Huang et al., "Synergistic induction of mouse serum amyloid A3 promoter by the inflammatory mediators IL-1 and IL-6." Interferon Cytokine Res, 19:1403-1411 (1999).
Janke et al. "Post-translational regulation of the microtubule cytoskeleton: mechanisms and functions." Nat Rev Mol Cell Biol, 12(12): 773-86 (2011).
Janke C., "The tubulin code: molecular components, readout mechanisms, and functions." J Cell Biol, 206(4): 461-72 (2014).
Koehler et al., "A complex task? Direct modulation of transcription factors with small molecules." Curr. Opin. Chem. Biol., 14:331-340 (2010).
Komlodi-Pasztor et al., "Inhibitors targeting mitosis: tales of how great drugs against a promising target were brought down by a flawed rationale", Clin Cancer Res, 18(1): 51-63 (2012).
Laursen, L., "A preventable cancer." Nature, 516(7529): p. S2-3 (2014).
Li et al., "Trifluoroacetic acid-mediated hydroarylation: synthesis of dihydrocoumarins and dihydroquinolones." J. Org. Chem., 70:2881-2883 (2005).
Long et al., "Repression of TFIIH transcriptional activity and TFIIH-associated cdk7 kinase activity at mitosis", Mol Cell Biol,18(3): 1467-76 (1998).
Lu et al., "Increased alpha-tubulin1b expression indicates poor prognosis and resistance to chemotherapy in hepatocellular carcinoma", Dig Dis Sci, 58(9): 2713-20 (2013).
Milite et al., "The emerging role of lysine methyltransferase SETD8 in human diseases", Clin Epigenetics, 8(102): 1-15 (2016).
Murata et al. "Transcription factor CP2 is essential for lens-specific expression o fthe chicken alphaA-crystallin gene.", Genes to Cells, 3:443-457 (1998).
Nishioka, K., et al., "PR-Set7 is a nucleosome-specific methyltransferase that modifies lysine 20 of histone H4 and is associated with silent chromatin", Mol Cell, 9(6): 1201-1213 (2002).
Palozola, K.C., et al., "Mitotic transcription and waves of gene reactivation during mitotic exit", Science, 358 (6359):119-122 (2017).
Park, I.Y., et al., Dual Chromatin and Cytoskeletal Remodeling by SETD2. Cell, 166(4): 950-962 (2016).
Porta-de-la-Riva et al., "TFCP2c/LSF/LBP-1c is required for Snail1-induced fibronectin gene expression." J. Biochem., 435:563-568 (2011).
Powell et al., "Inhibition of the mammalian transcription factor LSF induces S-phase-dependent apoptosis by downregulating thymidylate synthase expression." EMBO J, 19:4665-4675 (2000).
Rice et al., Mitotic-specific methylation of histone H4 Lys 20 follows increased PR-Set7 expression and its localization to mitotic chromosomes. Genes Dev,16(17): 2225-30 (2002).
Saxena et al., "Phosphorylation by cyclin C/cyclin-dependent kinase 2 following mitogenic stimulation of murine fibroblasts inhibits transcriptional activity of LSF during G1 progression." Mol Cell Biol., 29:2335-2345 (2009).
Sharma et al.,"Exploiting the balance between life and death: targeted cancer therapy and 'oncogenic shock.'" Biochem. Pharmacol, 80:666-673 (2010).
Shi, X., et al., "Modulation of p53 function by SET8-mediated methylation at lysine 382", Mol Cell, 27(4): 636-46 (2007).
Shirra et al., "LSF and NTF-1 share a conserved DNA-recognition motif yet required different oligomerization states to form a stable protein-DNA complex." J Biol Chem., 273:19260-19268 (1998).
Singh et al.,"Design and Synthesis of C-Ring Lactone- and Lactam-Based Podophyllotoxin Analogues as Anticancer Agents." Chemical & Pharmaceutical Bulletin, 58(2):242-246 (2010).
Song et al., "Post-translational modifications of tubulin: pathways to functional diversity of microtubules", Trends Cell Biol, 25(3): 125-136(2015).
Stanton et al., "Drugs that target dynamic microtubules: a new molecular perspective", Med Res Rev, 31(3): 443-81 (2011).
STN Registry Database, RN: 599151-35-6.
STN Registry Database, RN: 717828-57-4.
STN Registry Database, RN: 725687-12-7.
STN Registry Database, RN: 847462-19-5.
STN Registry Database, RN: 847482-88-6.
STN Registry Database, RN: 900129-51-3.
Swendeman et al., "Characterization of the genomic structure chromosomal location, promoter and developmental expression fo the alpha-globin transcription factor CP2." J Biol Chem, 269:11663-11671 (1994).
Traylor-Knowles et al., "The evolutionary diversification of LSF and Grainyhead transcription factors preceded the radiation of basal animal lineages", BMC Evolutionary Biology, 10:101 (2010).
Yoo et al., "Transcription factor Late SV40 Factor (LSF) functions as an oncogene in hepatocellular carcinoma" Proc Natl Acad Sci U S A, 107(18): 8357-8362 (2010).
Rajasekaran et al., "Small molecule inhibitors of Late SV40 Factor (LSF) abrogate hepatocellular carcinoma (HCC): Evaluation using an endogenous HCC model." Oncotarget 6(28): 26266-26277 (2015).
Veljkovic et al., "Lineage-specific and ubiquitous biological roles of the mammalian transcription factor LSF." Gene, 343:23-40 (2004).
Verhey et al., "The tubulin code", Cell Cycle, 6(17): 2152-2160 (2007).
Weinstein et al., "Oncogene Addiction." Cancer Res, 68:3077-3080 (2008).
Wu et al., "A new regulator of the cell cycle: the PR-Set7 histone methyltransferase", Cell Cycle, 10(1): 68-72 (2011).
Yoo et al., "Astrocyte elevated gene-1 regulates hepatocellular carcinoma development and progression." J Clin Invest, 119:465-477 (2009).
Yoo et al.,"Identification of genes conferring resistance to 5-fluorouracil." PNAS, 106:12938-12943 (2009).
Yoo et al.,"Transcription factor late SV40 (LSF) functions as an oncogene in hepatocellular carcinoma." PNAS, 107:8357-8362 (2010).
Zhang et al., "The interplay of histone modifications—writers that read" EMBO Rep,16(11): 1467-1481 (2015).
Zhong et al., "Evidence that levels of the dimeric cellular transcription factor CP2 play little role in the activation of the HIV-1 long terminal repeat in vivo or following superinfection with herpes simplex virus type 1." J Biol Chem, 269:21269-21276 (1994).
PUBCHEM-CID: 2943604, Structure, 1-8, (2005).
STN-Chemical database registry # 725686-76-0 for 9-(2-ethoxyphenyl)-2,3,8,9-tetrahydro-1,4-Dioxino[2,3-g]quinolin-7 (6H)-one Entered STN: Aug. 12, 2004.
Online: "http://web.archive.org/web/20090414214134/http://www.htscompounds.com/index.html" dated Apr. 14, 2009, accessed Aug. 21, 2015.
Wisclicenus et al., "Adolph Strecker's Short Textbook of Organic Chemistry", Spottiswoode: London, 38-39, (1881).
Wolff et al., "Burger's Medicinal Chemistry, 5ed, Part 1", John Wiley & Sons, 975-977, (1995).
Banker et al., "Modern Pharmaceutics, 3ed", Marcel Dekker, New York, 451-596, (1996).
Rautio et al., "Prodrugs: design and clinical Applications", Nature Reviews Drug Discovery, 7, 255-270, (2008).
Beaumont, "Design of Ester Prodrugs to Enhance Oral Absorption of Poorly Permeable Compounds: Challenges to the Discovery Scientist", Current Drug Metabolism, 4, 461-485, (2003).

(56) References Cited

OTHER PUBLICATIONS

Santhekadur, "The transcription factor LSF: a novel oncogene for hepatocellular carcinoma", American Journal of Cancer Research, 2, (3.), 269-285, (2012).

* cited by examiner

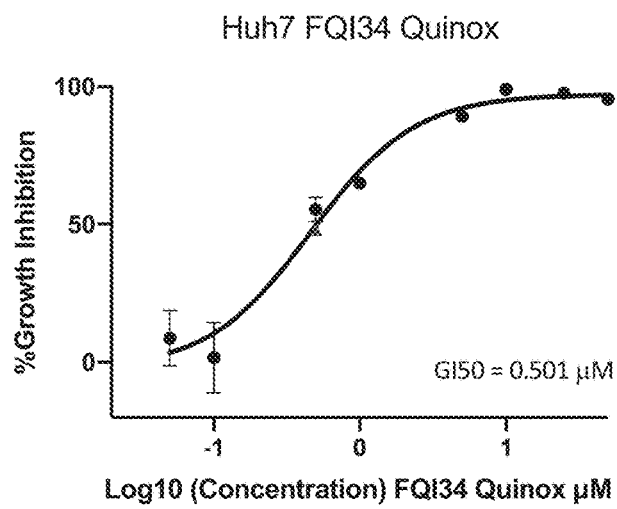
FIG. 2
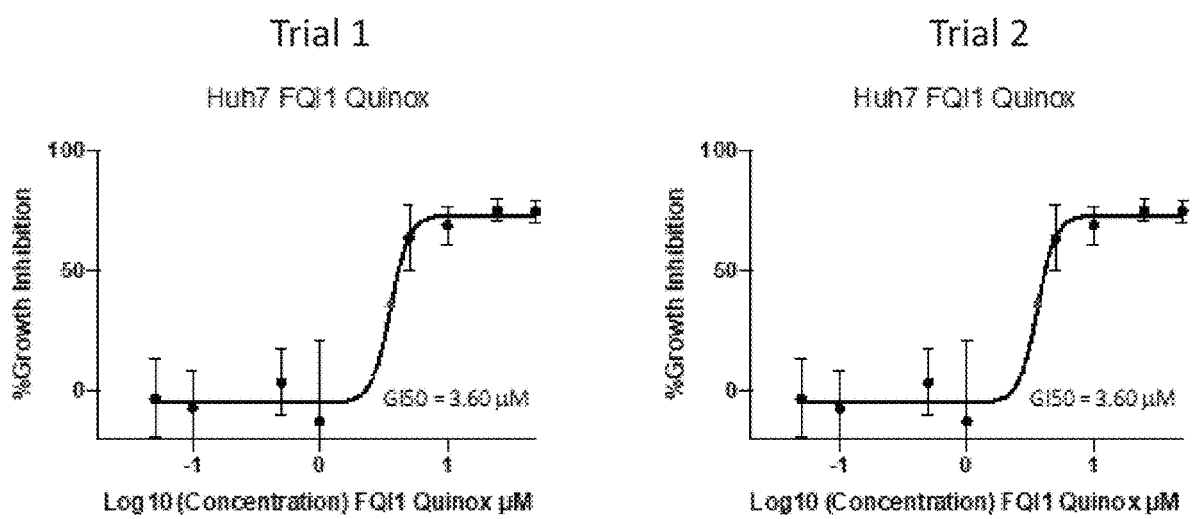
FIG. 3A
FIG. 3B

HETEROCYCLIC LSF INHIBITORS AND THEIR USES

RELATED APPLICATIONS

This application claims benefit under 35 U.S.C. § 119(e) of U.S. Provisional Application No. 62/965,384, filed Jan. 24, 2020, the content of which is incorporated herein by reference in its entirety.

FIELD OF THE INVENTION

The present invention generally relates to heterocyclic SV40 Factor (LSF) inhibitors and their uses, for example in a method for treating cancer, e.g., hepatocellular carcinoma (HCC).

BACKGROUND OF THE INVENTION

Transcription factor LSF is an oncogene in Hepatocellular Carcinoma (HCC), being dramatically overexpressed in HCC cell lines and patient samples. LSF is also generally required for cell cycle progression and cell survival. Initially, LSF was described as a regulator of G1/S progression, and essential for inducing expression of the gene encoding thymidylate synthase (TYMS) in late G1. However, the inventors have discovered, inter alia, additional involvement of LSF in mitosis. Particularly, inhibiting LSF with an exemplary small molecule inhibitor of LSF abrogated the DNA-binding and corresponding transcriptional activities of LSF, as well as specific LSF-protein interactions and inhibited growth of HCC tumors in multiple mouse models. In HCC cell lines, inhibition of LSF caused cell death via mitotic defect.

Hepatocellular carcinoma is a primary malignant tumor, which develops in the liver. HCC is one of the five most common cancers and the third leading cause of cancer deaths worldwide. The incidence of HCC is increasing despite a decrease in overall incidence of all cancers. In the United States, the estimated new cases of HCC for 2008 were 21,370, of which 18,410 were expected to die. There are multiple etiologies, with subcategories displaying distinct gene expression profiles. The prognosis of HCC remains poor. The mean 5-year survival rate is less than 10%. The mortality rate of HCC parallels that of its incidence because HCC is a tumor with rapid growth and early vascular invasion that is resistant to conventional chemotherapy.

Hepatocellular carcinoma (HCC) is characterized by late stage diagnosis and a poor prognosis for treatment, usually consisting of surgical resection of the tumor and chemotherapy. Currently, the only approved systemic treatments for late stage primary malignancies are sorafenib and regorafenib. The current treatment options for HCC are not optimal, especially following metastasis. Irradiation and chemotherapies have not so far proved to be satisfactory; surgery is the most effective treatment of HCC. However, surgery is only appropriate for patients with small resectable tumors. Only two, molecularly based drugs (Sorafenib and Regorafenib), which target tyrosine kinase receptors and the MEK/ERK pathway, have generated responses in patients as a single therapy. However, increased survival times with Sorafenib are only a few months. Regorafenib, a closely related compound, has recently been approved for treatment of sorafenib-resistant patients, although again with limited survival benefit. As such, it is imperative to discover novel, effective, and targeted therapies for this highly aggressive cancer. In particular, there is a strong need in the art for improved methods for treatment of HCC with small-molecule drugs.

SUMMARY OF THE INVENTION

The present invention is generally directed to compounds, and their preparation, represented by Formula (I), which are inhibitors of Late SV40 factor (LSF). In some implementations, the invention relates to methods, compositions and kits including the compounds (I) to treat cancer e.g. hepatocellular carcinoma (HCC). The compounds herein described retain potent activity against the LSF target while eliminating a chiral center contained in a previous genus and the attendant synthetic complications. Inter alia, the compounds offer manufacturing advantages and are readily formulated for therapeutic use. In some implementations, a compound of Formula (I) as disclosed herein, can be used to treat other cancers, for example, breast cancer, colon cancer, ovarian cancer, lung cancer, kidney cancer, cancers of the hematopoietic system, cancers of the endometrium, cervical cancer, cancers of the upper digestive tract, stomach cancer, pancreatic cancer, liver cancers, cancers of the small intestine, and the like.

According to some implementations the disclosure relates to a compound of Formula (I), or enantiomers, prodrugs, derivatives, and pharmaceutically acceptable salts thereof:

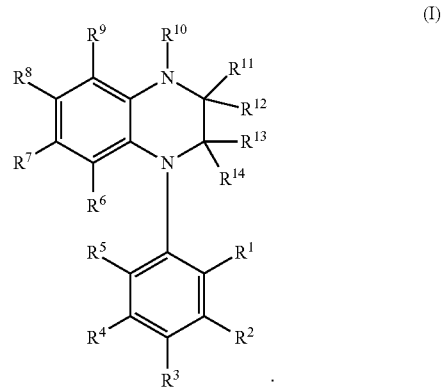

(I)

In compound (I), none, one, or more vicinal pairs of $R^1$, $R^2$, $R^3$, $R^4$, $R^5$, $R^6$, $R^7$, $R^8$, and $R^9$ each, together with the carbons to which they are attached, form a 5-8 membered cycloalkyl or heterocyle ring; and the remaining $R^1$, $R^2$, $R^3$, $R^4$, $R^5$, $R^6$, $R^7$, $R^8$ or $R^9$ are each independently selected from the group consisting of hydrogen, halogen, $OR^{14}$, $NR^{14}R^{24}$, $SR^{14}$, $SO_2R^{14}$, —$NO_2$, $C_1$-$C_6$ alkyl, $C_1$-$C_6$ haloalkyl, $C_1$-$C_6$ heteroalkyl, $C_2$-$C_8$alkenyl, aryl, and heteroaryl. In compound (I), $R^{10}$ is hydrogen, $C_1$-$C_6$ alkyl, $C_1$-$C_6$ haloalkyl, $C_1$-$C_6$ heteroalkyl, $C_2$-$C_8$alkenyl, aryl, heteroaryl, or halogen; or $R^{10}$ and one of the vicinal $R^{11}$ or $R^{12}$ groups together form a double bond between the carbon atoms they are attached to. In compound (I) none or a vicinal pair of $R^{11}$, $R^{12}$, $R^{13}$ and $R^{14}$ together form a double bond between the carbon atoms they are attached to and the remaining $R^{11}$, $R^{12}$, $R^{13}$ and $R^{14}$ are each independently selected from the group consisting of hydrogen, halogen, $C_1$-$C_6$ alkyl, $C_1$-$C_6$ haloalkyl, $C_1$-$C_6$ heteroalkyl, $C_2$-$C_8$alkenyl, $OR^{34}$, $SR^{34}$, $SO_2R^{34}$, $NR^{34}R^{44}$ halogen, heteroaryl, and aryl. Alternatively, in structure (I), one or two of a germinal pair of $R^{11}$, $R^{12}$, $R^{13}$ and $R^{14}$ together form a carbonyl (═O) and the remaining $R^{11}$, $R^{12}$, $R^{13}$ and $R^{14}$ are each independently selected from the group consisting of hydrogen, halogen, $C_1$-$C_6$ alkyl, $C_1$-$C_6$ haloalkyl, $C_1$-$C_6$ heteroalkyl, $C_2$-$C_8$alkenyl, $OR^{3A}$, $SR^{3A}$, $SO_2R^{3A}$, $NR^{3A}R^{4A}$ heteroaryl, and aryl. The $R^{1A}$, $R^{2A}$, $R^{3A}$ and $R^{4A}$ are each independently selected from the group consisting of hydrogen, $C_1$-$C_8$ alkyl, $C_2$-$C_8$ alkenyl, $C_2$-$C_8$ alkynyl, cycloalkyl, heterocyclyl, $C_1$-$C_8$ haloalkyl, $C_1$-$C_8$ heteroalkyl, heteroaryl, and aryl, wherein the alkyl, alkenyl, alkynyl, cycloalkyl, heterocyclyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl or $C_1$-$C_6$ alkoxy. Any one or more of the 5-8 membered cycloalkyl, the heterocyle ring, the alkyl, the haloalkyl, the heteroalkyl, the alkenyl, the heteroaryl, and the aryl can be optionally substituted with halogen, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono($C_1$-$C_6$ alkyl)amino or di($C_1$-$C_6$ alkyl)amino.

According to some implementations, the disclosure is a pharmaceutical composition comprising a compound (I) and a pharmaceutically acceptable excipient or carrier.

According to some implementations, the disclosure is for inhibiting LSF in a subject, the method comprising administering an effective amount of a compound (I), or a pharmaceutical composition including compound (I), to a subject in need thereof.

According to some implementations, the disclosure is method for treating cancer in a subject, the method comprising administering an effective amount of a compound (I), or a pharmaceutical composition including compound (I), to a subject in need thereof.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIGS. 1A-4 are line graph showing the cell growth inhibiting activity of some exemplary compounds.

DETAILED DESCRIPTION OF THE INVENTION

Figures 1A, 1B, 1C:
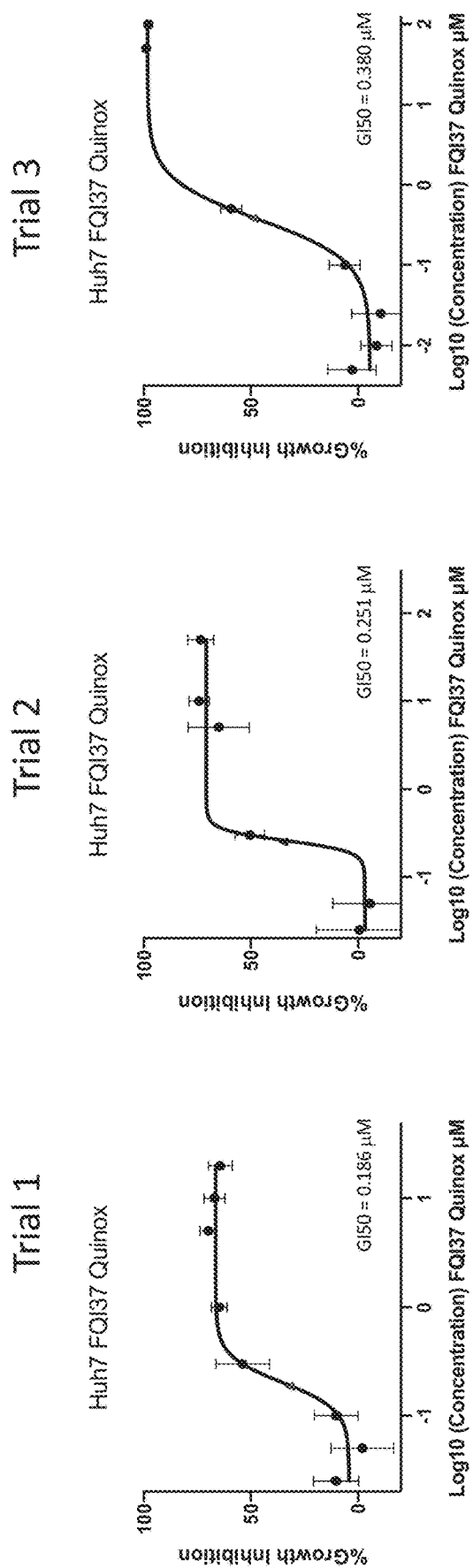

The inventors have discovered inter alia, small-molecule compounds of Formula (I). These small molecule compounds as disclosed herein can cause cell death of cancer cell lines and primary cancer cells in an in vitro assay, e.g., HCC cancer cell lines, pancreatic cancer lines, ductal cell lines, colorectal cell lines, breast cancer cell lines, colon cancer cell lines, ovarian cancer cell lines etc. Therefore, in one aspect, the disclosure provides small-molecule compounds of Formula (I). In some implementations, the compounds disclosed herein can be used in a method for inhibiting LSF and/or for treatment of cancers in subjects, e.g. HCC and other cancers.

Accordingly, in some implementations, the disclosure relates to a compound of Formula (I), or enantiomers, prodrugs, derivatives, and pharmaceutically acceptable salts thereof:

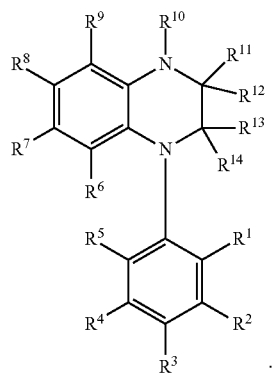

In compounds of Formula (I), none, one, or more vicinal pairs of $R^1$, $R^2$, $R^3$, $R^4$, $R^5$, $R^6$, $R^7$, $R^8$, and $R^9$ each, together with the carbons to which they are attached, form a 5-8 membered cycloalkyl or heterocyle ring; and the remaining $R^1$, $R^2$, $R^3$, $R^4$, $R^5$, $R^6$, $R^7$, $R^8$ or $R^9$ are each independently selected from the group consisting of hydrogen, halogen, $OR^{1A}$, $NR^{1A}R^{2A}$, $SR^{1A}$, $SO_2R^{1A}$, —$NO_2$, $C_1$-$C_6$ alkyl, $C_1$-$C_6$ haloalkyl, $C_1$-$C_6$ heteroalkyl, $C_2$-$C_8$alkenyl, aryl, and heteroaryl. In compound (I), $R^{10}$ is hydrogen, $C_1$-$C_6$ alkyl, $C_1$-$C_6$ haloalkyl, $C_1$-$C_6$ heteroalkyl, $C_2$-$C_8$alkenyl, aryl, heteroaryl, or halogen; or $R^{10}$ and one of the vicinal $R^{11}$ or $R^{12}$ groups together form a double bond between the carbon atoms they are attached to. In compounds of Formula (I) none or a vicinal pair of $R^{11}$, $R^{12}$, $R^{13}$ and $R^{14}$ together form a double bond between the carbon atoms they are attached to and the remaining $R^{11}$, $R^{12}$, $R^{13}$ and $R^{14}$ are each independently selected from the group consisting of hydrogen, halogen, $C_1$-$C_6$ alkyl, $C_1$-$C_6$ haloalkyl, $C_1$-$C_6$ heteroalkyl, $C_2$-$C_8$alkenyl, $OR^{3A}$, $SR^{3A}$, $SO_2R^{3A}$, $NR^{3A}R^{4A}$ heteroaryl, and aryl. Alternatively, in structure (I), one or two of a germinal pair of $R^{11}$, $R^{12}$, $R^{13}$ and $R^{14}$ together form a carbonyl (=O) and the remaining $R^{11}$, $R^{12}$, $R^{13}$ and $R^{14}$ are each independently selected from the group consisting of hydrogen, halogen, $C_1$-$C_6$ alkyl, $C_1$-$C_6$ haloalkyl, $C_1$-$C_6$ heteroalkyl, $C_2$-$C_8$alkenyl, $OR^{3A}$, $SR^{3A}$, $SO_2R^{3A}$ $NR^{3A}R^{4A}$ halogen, heteroaryl, and aryl.

In compounds of Formula (I), the $R^{1A}$, $R^{2A}$, $R^{3A}$ and $R^{4A}$ are each independently selected from the group consisting of hydrogen, $C_1$-$C_8$ alkyl, $C_2$-$C_8$ alkenyl, $C_2$-$C_8$ alkynyl, cycloalkyl, heterocyclyl, $C_1$-$C_8$ haloalkyl, $C_1$-$C_8$ heteroalkyl, heteroaryl, and aryl, wherein the alkyl, alkenyl, alkynyl, cycloalkyl, heterocyclyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl or $C_1$-$C_6$ alkoxy. any of the 5-8 membered cycloalkyl, the heterocyle ring, the alkyl, the haloalkyl, the heteroalkyl, the alkenyl, the heteroaryl, and the aryl can be optionally substituted with halogen, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono($C_1$-$C_6$ alkyl)amino or di($C_1$-$C_6$ alkyl)amino.

According to some implementations of compounds of Formula (I), $R^1$ is hydrogen, halogen, $OR^{1A}$, $NR^{1A}R^{2A}$, $SR^{1A}$, $C_1$-$C_6$alkyl or —$NO_2$. In some implementations $R^1$ is hydrogen, halogen, $OR^{1A}$ or $NR^{1A}R^{2A}$. In some implementations, $R^{1A}$ and $R^{2A}$ independently are H or $C_1$-$C_6$alkyl. In some implementations, $R^{1A}$ and $R^{2A}$ are hydrogen. In some implementations, $R^{1A}$ and $R^{2A}$ independently are H, methyl, ethyl, propyl, isopropyl, butyl, isobutyl, t-butyl or pentyl. In some implementations, $R^{1A}$ and $R^{2A}$ independently are methyl, ethyl, propyl or isopropyl. In some implementations, $R^{1A}$ and $R^{2A}$ are methyl. In some implementations, $R^1$ is hydrogen or $OR^{1A}$. In some implementations, $R^1$ is $OR^{1A}$. According to some of these implementations, $R^{1A}$ is H, alkyl, alkenyl, alkynyl, cycloalkyl, heterocyclyl, aryl or heteroaryl, for example, in some implementations, $R^{1A}$ is H or alkyl. In some implementations, $R^1$ is OH or $O(C_1$-$C_6$ alkyl). In some implementations, $R^1$ is OH, methoxy, ethoxy, propoxy or isopropoxy. For example, in some implementations, $R^1$ is ethoxy. In some implementations, $R^1$ is hydrogen.

According to some implementations of compounds of Formula (I), $R^2$ is hydrogen, halogen, $OR^{1A}$, $NR^{1A}R^{2A}$, $SR^{1A}$, $C_1$-$C_6$alkyl or $-NO_2$. In some implementations, $R^2$ is hydrogen, halogen, $C_1$-$C_6$alkyl, $OR^{1A}$ or $NR^{1A}R^{2A}$. In some implementations, $R^{1A}$ and $R^{2A}$ independently are H or $C_1$-$C_6$alkyl. In some implementations, $R^{1A}$ and $R^{2A}$ are hydrogen. In some implementations, $R^{1A}$ and $R^{2A}$ independently are H, methyl, ethyl, propyl, isopropyl, butyl, isobutyl, t-butyl or pentyl. In some implementations, $R^{1A}$ and $R^{2A}$ independently are methyl, ethyl, propyl or isopropyl. In some implementations, $R^{1A}$ and $R^{2A}$ are methyl. In some implementations, $R^2$ is hydrogen, halogen or $OR^{1A}$. In some implementations, $R^2$ is $OR^{1A}$. According to some of these implementations, $R^{1A}$ is H, alkyl, alkenyl, alkynyl, cycloalkyl, heterocyclyl, aryl or heteroaryl, for example, in some implementations, $R^{1A}$ is H or alkyl. In some implementations, $R^2$ is OH or $O(C_1$-$C_6$ alkyl). In some implementations, $R^2$ is OH, methoxy, ethoxy, propoxy or isopropoxy. For example, in some implementations, $R^2$ is ethoxy. In some implementations, $R^2$ is hydrogen.

According to some implementations of compounds of Formula (I), $R^3$ is hydrogen, halogen, $OR^{1A}$, $NR^{1A}R^{2A}$, $SR^{1A}$, $C_1$-$C_6$alkyl or $-NO_2$. In some implementations, $R^3$ is halogen, $OR^{1A}$, $NR^{1A}R^{2A}$, $C_1$-$C_6$alkyl or $-NO_2$. In some implementations, $R^3$ is halogen, $NR^{1A}R^{2A}$, $C_1$-$C_6$alkyl or $-NO_2$. In some implementations, $R^3$ is halogen, or $NR^{1A}R^{2A}$. According to some of these implementations, $R^{1A}$ and $R^{2A}$ independently are H, alkyl, alkenyl, cycloalkyl, heterocyclyl, aryl or heteroaryl. In some implementations, $R^{1A}$ and $R^{2A}$ independently are H or $C_1$-$C_6$alkyl. In some implementations, $R^{1A}$ and $R^{2A}$ are hydrogen. In some implementations, $R^{1A}$ and $R^{2A}$ independently are H, methyl, ethyl, propyl, isopropyl, butyl, isobutyl, t-butyl or pentyl. In some implementations, $R^{1A}$ and $R^{2A}$ independently are methyl, ethyl, propyl or isopropyl. In some implementations, $R^{1A}$ and $R^{2A}$ are methyl. In some implementations, $R^3$ is hydrogen. In some implementations, $R^3$ is $-NO_2$.

According to some implementations of compounds of Formula (I), $R^4$ is hydrogen, halogen, $OR^{1A}$, $NR^{1A}R^{2A}$, $SR^{1A}$, $C_1$-$C_6$alkyl or $-NO_2$. In some implementations, $R^4$ is hydrogen, halogen, $C_1$-$C_6$alkyl, $OR^{1A}$ or $NR^{1A}R^{2A}$. In some implementations, $R^{1A}$ and $R^{2A}$ independently are H or $C_1$-$C_6$alkyl. In some implementations, $R^{1A}$ and $R^{2A}$ are hydrogen. In some implementations, $R^{1A}$ and $R^{2A}$ independently are H, methyl, ethyl, propyl, isopropyl, butyl, isobutyl, t-butyl or pentyl. In some implementations, $R^{1A}$ and $R^{2A}$ independently are methyl, ethyl, propyl or isopropyl. In some implementations, $R^{1A}$ and $R^{2A}$ are methyl. In some implementations, $R^4$ is hydrogen, halogen or $OR^{1A}$. According to some of these implementations, $R^{1A}$ is H, alkyl, alkenyl, alkynyl, cycloalkyl, heterocyclyl, aryl or heteroaryl, for example, in some implementations, $R^{1A}$ is H or alkyl. In some implementations, $R^4$ is OH or $O(C_1$-$C_6$ alkyl). In some implementations, $R^4$ is OH, methoxy, ethoxy, propoxy or isopropoxy. For example, in some implementations, $R^4$ is ethoxy. In some implementations, $R^4$ is hydrogen.

According to some implementations of compounds of Formula (I), $R^5$ is hydrogen, halogen, $OR^{1A}$, $NR^{1A}R^{2A}$, $SR^{1A}$, $C_1$-$C_6$alkyl or $-NO_2$. In some implementations, $R^5$ is hydrogen, halogen, $C_1$-$C_6$alkyl, $OR^{1A}$ or $NR^{1A}R^{2A}$. In some implementations, $R^{1A}$ and $R^{2A}$ independently are H or $C_1$-$C_6$alkyl. In some implementations, $R^{1A}$ and $R^{2A}$ are hydrogen. In some implementations, $R^{1A}$ and $R^{2A}$ independently are H, methyl, ethyl, propyl, isopropyl, butyl, isobutyl, t-butyl or pentyl. In some implementations, $R^{1A}$ and $R^{2A}$ independently are methyl, ethyl, propyl or isopropyl. In some implementations, $R^{1A}$ and $R^{2A}$ are methyl. In some implementations, $R^5$ is hydrogen, halogen or $OR^{1A}$. According to some of these implementations, $R^{1A}$ is H, alkyl, alkenyl, alkynyl, cycloalkyl, heterocyclyl, aryl or heteroaryl, for example, in some implementations, $R^{1A}$ is H or alkyl. In some implementations, $R^5$ is OH or $O(C_1$-$C_6$ alkyl). In some implementations, $R^5$ is OH, methoxy, ethoxy, propoxy or isopropoxy. For example, in some implementations, $R^5$ is ethoxy. In some implementations, $R^5$ is hydrogen.

According to some implementations of compounds of Formula (I), $R^6$ is hydrogen, halogen, $OR^{1A}$, $NR^{1A}R^{2A}$, $SR^{1A}$, or $C_1$-$C_6$ alkyl. In some of these implementations, $R^{1A}$ and $R^{2A}$ independently are H or $C_1$-$C_6$alkyl. In some implementations, $R^{1A}$ and $R^{2A}$ are hydrogen. In some implementations, $R^{1A}$ and $R^{2A}$ independently are H, methyl, ethyl, propyl, isopropyl, butyl, isobutyl, t-butyl or pentyl. In some implementations, $R^{1A}$ and $R^{2A}$ independently are methyl, ethyl, propyl or isopropyl. In some implementations, $R^{1A}$ and $R^{2A}$ are methyl. In some implementations, $R^6$ is hydrogen, halogen, $OR^{1A}$, $SR^{1A}$, or $C_1$-$C_6$ alkyl. In some implementations, $R^6$ is hydrogen, halogen, or $OR^{1A}$. According to some of these implementations, $R^{1A}$ is H, alkyl, alkenyl, alkynyl, cycloalkyl, heterocyclyl, aryl or heteroaryl, for example, in some implementations, $R^{1A}$ is H or alkyl. In some implementations, $R^6$ is H.

According to some implementations of compounds of Formula (I), $R^7$ is hydrogen, halogen, $OR^{1A}$, $NR^{1A}R^{2A}$, $SR^{1A}$, or $C_1$-$C_6$ alkyl. In some of these implementations, $R^{1A}$ and $R^{2A}$ independently are H or $C_1$-$C_6$alkyl. In some implementations, $R^{1A}$ and $R^{2A}$ are hydrogen. In some implementations, $R^{1A}$ and $R^{2A}$ independently are H, methyl, ethyl, propyl, isopropyl, butyl, isobutyl, t-butyl or pentyl. In some implementations, $R^{1A}$ and $R^{2A}$ independently are methyl, ethyl, propyl or isopropyl. In some implementations, $R^{1A}$ and $R^{2A}$ are methyl. In some implementations, $R^7$ is hydrogen, halogen, $OR^{1A}$, $SR^{1A}$, or $C_1$-$C_6$ alkyl. In some implementations, $R^7$ is hydrogen, halogen, or $OR^{1A}$ In some implementations, $R^7$ is H or $OR^{1A}$. According to some of these implementations, $R^{1A}$ is H, alkyl, alkenyl, alkynyl, cycloalkyl, heterocyclyl, aryl or heteroaryl, for example, in some implementations, $R^{1A}$ is H or alkyl. In some implementations, $R^7$ is H.

According to some implementations of compounds of Formula (I), $R^8$ is hydrogen, halogen, $OR^{1A}$, $NR^{1A}R^{2A}$, $SR^{1A}$, or $C_1$-$C_6$ alkyl. In some of these implementations, $R^{1A}$ and $R^{2A}$ independently are H or $C_1$-$C_6$alkyl. In some implementations, $R^{1A}$ and $R^{2A}$ are hydrogen. In some implementations, $R^{1A}$ and $R^{2A}$ independently are H, methyl, ethyl, propyl, isopropyl, butyl, isobutyl, t-butyl or pentyl. In some implementations, $R^{1A}$ and $R^{2A}$ independently are methyl, ethyl, propyl or isopropyl. In some implementations, $R^{1A}$ and $R^{2A}$ are methyl. In some implementations, $R^8$ is hydrogen, halogen, $OR^{1A}$, $SR^{1A}$, or $C_1$-$C_6$ alkyl. In some implementations, $R^8$ is hydrogen, halogen, or $OR^{1A}$ In some implementations, $R^8$ is H or $OR^{1A}$. According to some of these implementations, $R^{1A}$ is H, alkyl, alkenyl, alkynyl, cycloalkyl, heterocyclyl, aryl or heteroaryl, for example, in some implementations, $R^{1A}$ is H or alkyl. In some implementations, $R^8$ is H.

According to some implementations of compounds of Formula (I), $R^9$ is hydrogen, halogen, $OR^{1A}$, $NR^{1A}R^{2A}$, $SR^{1A}$, or $C_1$-$C_6$ alkyl. In some of these implementations, $R^{1A}$ and $R^{2A}$ independently are H or $C_1$-$C_6$ alkyl. In some implementations, $R^{1A}$ and $R^{2A}$ are hydrogen. In some implementations, $R^{1A}$ and $R^{2A}$ independently are H, methyl, ethyl, propyl, isopropyl, butyl, isobutyl, t-butyl or pentyl. In some implementations, $R^{1A}$ and $R^{2A}$ independently are methyl, ethyl, propyl or isopropyl. In some implementations, $R^{1A}$ and $R^{2A}$ are methyl. In some implementations, $R^9$ is hydrogen, halogen, $OR^{1A}$, $SR^{1A}$, or $C_1$-$C_6$ alkyl. In some implementations, $R^9$ is hydrogen, halogen, or $OR^{1A}$ In some implementations, $R^9$ is H or $OR^{1A}$. According to some of these implementations, $R^{1A}$ is H, alkyl, alkenyl, alkynyl, cycloalkyl, heterocyclyl, aryl or heteroaryl, for example, in some implementations, $R^{1A}$ is H or alkyl. In some implementations, $R^9$ is H.

According to some implementations of compounds of Formula (I), $R^{10}$ is hydrogen, methyl, ethyl, propyl, isopropyl, butyl, isobutyl, t-butyl or pentyl. In some implementations, $R^{10}$ is hydrogen.

According to some implementations of compounds of Formula (I), $R^{11}$ is hydrogen, halogen, $OR^{1A}$ or $C_1$-$C_6$alkyl. In some implementations, $R^{11}$ is hydrogen or $C_1$-$C_6$alkyl. In some implementations, $R^{11}$ is hydrogen.

According to some implementations of compounds of Formula (I), $R^{12}$ is hydrogen, halogen, $OR^{1A}$ or $C_1$-$C_6$alkyl. In some implementations, $R^{12}$ is hydrogen or $C_1$-$C_6$alkyl. In some implementations, $R^{12}$ is hydrogen.

According to some implementations of compounds of Formula (I), $R^{13}$ is hydrogen, halogen, $OR^{1A}$ or $C_1$-$C_6$alkyl. In some implementations, $R^{13}$ is hydrogen or $C_1$-$C_6$alkyl. In some implementations, $R^{13}$ is hydrogen.

According to some implementations of compounds of Formula (I), $R^{14}$ is hydrogen, halogen, $OR^{1A}$ or $C_1$-$C_6$alkyl. In some implementations, $R^{14}$ is hydrogen or $C_1$-$C_6$alkyl. In some implementations, $R^{14}$ is hydrogen.

According to some implementations of compounds of Formula (I), $R^7$ and $R^8$ together with the carbons to which they are attached, form a 5-8 membered cycloalkyl or heterocycle ring. In some implementations, $R^7$ and $R^8$ together with the carbons to which they are attached to form an optionally substituted dioxolane. In these implementations, the compound is represented by Formula (IA):

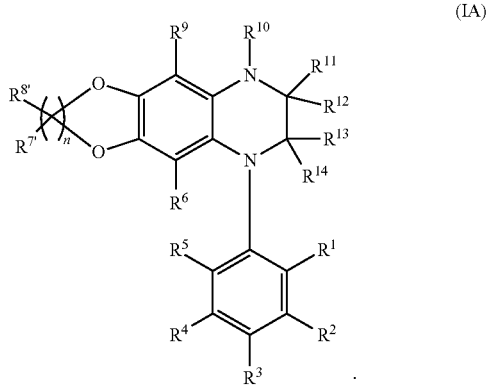

(IA)

In compounds of Formula (IA), n can be 1, 2, 3, or 4. For example, n can be 1 or 2. In some implementations, n is 1. In some other implementations, n is 2.

In compounds of Formula (IA) any combination of $R^1$ through $R^6$, IC, le, and $R^9$ through $R^{14}$ can be independently selected. In some implementations, $R^1$ is hydrogen, halogen, $OR^{1A}$, $NR^{1A}R^{2A}$, $SR^{1A}$, $C_1$-$C_6$alkyl or $-NO_2$. For example, $R^1$ is $O(C_1$-$C_6$ alkyl). In some implementations, $R^2$ is hydrogen, halogen, $OR^{1A}$, $NR^{1A}R^{2A}$, $SR^{1A}$, $C_1$-$C_6$alkyl or $-NO_2$. For example, optionally $R^2$ is hydrogen or halogen. In some implementation, $R^3$ is hydrogen, halogen, $OR^{1A}$, $NR^{1A}R^{2A}$, $C_1$-$C_6$alkyl, $C_2$-$C_8$alkenyl, or $-NO_2$. For example, optionally $R^3$ is $N(C_1$-$C_6$ alkyl)$_2$, halogen or $-NO_2$. In some implementations, $R^4$ is hydrogen, halogen, $OR^{1A}$, $NR^{1A}R^{2A}$, $SR^{1A}$, $C_1$-$C_6$alkyl or $-NO_2$. For example, optionally $R^4$ is hydrogen or halogen. In some implementations, $R^5$ is hydrogen, halogen, $OR^{1A}$, $NR^{1A}R^{2A}$, $SR^{1A}$, $C_1$-$C_6$alkyl or $-NO_2$. For example, optionally $R^5$ is hydrogen or halogen. In some implementations, $R^2$, $R^4$ and $R^5$ are hydrogen. In some implementations, $R^6$ is hydrogen, halogen, $OR^{1A}$, $NR^{1A}R^{2A}$, or $C_1$-$C_6$ alkyl. For example, optionally $R^6$ is hydrogen, halogen or $OR^{1A}$ In some implementations, $R^{7'}$ is hydrogen, halogen, $OR^{1A}$, $NR^{1A}R^{2A}$, $SR^{1A}$, or $C_1$-$C_6$ alkyl. For example, optionally $R^{7'}$ is H or F. In some implementations, 1eis hydrogen, halogen, $OR^{1A}$, $NR^{1A}R^{2A}$, $SR^{1A}$ or $C_1$-$C_6$ alkyl. For example, optionally $R^8$ is H or F. In some implementations, $R^9$ is hydrogen, halogen, $OR^{1A}$, $NR^{1A}R^{2A}$, or $C_1$-$C_6$ alkyl. For example, optionally $R^9$ is hydrogen, halogen or $OR^{1A}$ In some implementations, $R^{10}$ is hydrogen or $C_1$-$C_6$ alkyl. For example, in some implementations, $R^{10}$ is hydrogen. In some implementations, $R^{11}$ is hydrogen or $C_1$-$C_6$ alkyl. For example, optionally $R^{11}$ is hydrogen. In some implementations, $R^{12}$ is hydrogen or $C_1$-$C_6$ alkyl. For example, optionally $R^{12}$ is hydrogen. In some implementations, $R^{13}$ is hydrogen or $C_1$-$C_6$ alkyl. For example, optionally $R^{13}$ is hydrogen. In some implementations, $R^{14}$ is hydrogen or $C_1$-$C_6$ alkyl. For example, optionally $R^{14}$ is hydrogen. In some implementations at least one of $R^{11}$ and $R^{12}$ are hydrogen. In some implementations $R^{11}$ and $R^{12}$ are hydrogen. In some implementations at least one of $R^{13}$ and $R^{14}$ are hydrogen. In some implementations $R^{13}$ and $R^{14}$ are hydrogen. In some implementations $R^{11}$, $R^{12}$, $R^{13}$ and $R^{14}$ are hydrogen.

According to some implementations of compounds of Formula (I), $R^6$ and $R^7$ together with the carbons to which they are attached, form a 5-8 membered cycloalkyl or heterocycle ring. In some implementations, $R^7$ and $R^{7'}$ together with the carbons to which they are attached to form an optionally substituted dioxolane. In these implementations, the compound is represented by Formula (IB):

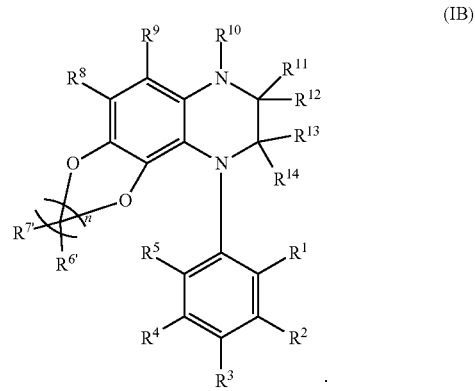

(IB)

In compounds of Formula (IB), n can be 1, 2, 3, or 4. For example, n can be 1 or 2. In some implementations, n is 1. In some other implementations, n is 2.

In compounds of Formula (IB) any combination of $R^1$ through $R^5$, $R^{6'}$, $R^{7'}$, and $R^8$ through $R^{14}$ can be independently selected. In some implementations, $R^1$ is hydrogen, halogen, $OR^{14}$, $NR^{14}R^{24}$, $SR^{14}$, $C_1$-$C_6$alkyl or —$NO_2$. For example, $R^1$ is $O(C_1$-$C_6$ alkyl). In some implementations, $R^2$ is hydrogen, halogen, $OR^{14}$, $NR^{14}R^{24}$, $SR^{14}$, $C_1$-$C_6$alkyl or —$NO_2$. For example, in some implementations, $R^2$ is hydrogen or halogen. In some implementation, $R^3$ is hydrogen, halogen, $OR^{14}$, $NR^{14}R^{24}$, $C_1$-$C_6$alkyl, $C_2$-$C_8$alkenyl or —$NO_2$. For example, in some implementations, $R^3$ is $N(C_1$-$C_6$ alkyl$)_2$, halogen or —$NO_2$. In some implementations, $R^4$ is hydrogen, halogen, $OR^{14}$, $NR^{14}R^{24}$, $SR^{14}$, $C_1$-$C_6$alkyl or —$NO_2$. For example, in some implementations, $R^4$ is hydrogen or halogen. In some implementations, $R^5$ is hydrogen, halogen, $OR^{14}$, $NR^{14}R^{24}$, $SR^{14}$, $C_1$-$C_6$alkyl or —$NO_2$. For example, optionally $R^5$ is hydrogen or halogen. In some implementations, $R^2$, $R^4$ and $R^5$ are hydrogen. In some implementations, $R^{6'}$ is hydrogen, halogen, $OR^{14}$, $NR^{14}R^{24}$, $SR^{14}$, or $C_1$-$C_6$ alkyl. For example, in some implementations, $R^{6'}$ is H or F. In some implementations, $R^{7'}$ is hydrogen, halogen, $OR^{14}$, $NR^{14}R^{24}$, or $C_1$-$C_6$ alkyl. For example, in some implementations, $R^{7'}$ is H or F. In some implementations, $R^8$ is hydrogen, halogen, $OR^{14}$, $NR^{14}R^{24}$, $SR^{14}$, or $C_1$-$C_6$ alkyl. For example, in some implementations, $R^8$ is hydrogen, halogen or $OR^{14}$. In some implementations, $R^9$ is hydrogen, halogen, $OR^{14}$, $NR^{14}R^{24}$, $SR^{14}$, or $C_1$-$C_6$ alkyl. For example, in some implementations, $R^9$ is hydrogen, halogen or $OR^{14}$. In some implementations, $R^{10}$ is hydrogen or $C_1$-$C_6$ alkyl. For example, in some implementations, $R^{10}$ is hydrogen. In some implementations, $R^{11}$ is hydrogen or $C_1$-$C_6$ alkyl. For example, in some implementations, $R^{11}$ is hydrogen. In some implementations, $R^{12}$ is hydrogen or $C_1$-$C_6$ alkyl. For example, in some implementations, $R^{12}$ is hydrogen. In some implementations, $R^{13}$ is hydrogen or $C_1$-$C_6$ alkyl. For example, in some implementations, $R^{13}$ is hydrogen. In some implementations, $R^{14}$ is hydrogen or $C_1$-$C_6$ alkyl. For example, in some implementations, $R^{14}$ is hydrogen. In some implementations at least one of $R^{11}$ and $R^{12}$ are hydrogen. In some implementations $R^{11}$ and $R^{12}$ are hydrogen. In some implementations at least one of $R^{13}$ and $R^{14}$ are hydrogen. In some implementations $R^{13}$ and $R^{14}$ are hydrogen. In some implementations $R^{11}$, $R^{12}$, $R^{13}$ and $R^{14}$ are hydrogen.

According to some implementations of compounds of Formula (I), $R^8$ and $R^9$ together with the carbons to which they are attached, form a 5-8 membered cycloalkyl or heterocycle ring. In some implementations, $R^8$ and $R^9$ together with the carbons to which they are attached to form an optionally substituted dioxolane. In these implementations, the compound is represented by Formula (IC):

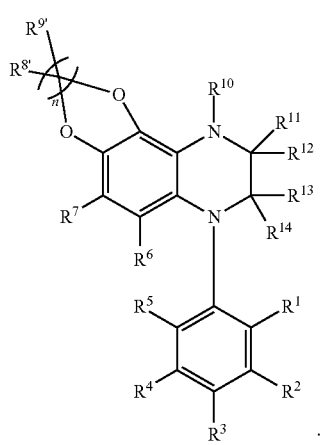

(IC)

In compounds of Formula (IC), n can be 1, 2, 3, or 4. For example, n can be 1 or 2. In some implementations, n is 1. In some other implementations, n is 2.

In compound of Formula (IC), any combination of $R^1$ through $R^7$, $R^{8'}$, $R^{9'}$, and $R^{10}$ through $R^{14}$ can be independently selected. In some implementations, $R^1$ is hydrogen, halogen, $OR^{14}$, $NR^{14}R^{24}$, $SR^{14}$, $C_1$-$C_6$alkyl or —$NO_2$. For example, $R^1$ is $O(C_1$-$C_6$ alkyl). In some implementations, $R^2$ is hydrogen, halogen, $OR^{14}$, $NR^{14}R^{24}$, $SR^{14}$, $C_1$-$C_6$alkyl or —$NO_2$. For example, in some implementations, $R^2$ is hydrogen or halogen. In some implementation, $R^3$ is hydrogen, halogen, $OR^{14}$, $NR^{14}R^{24}$, $C_1$-$C_6$alkyl, $C_2$-$C_8$alkenyl, or —$NO_2$. For example, in some implementations, $R^3$ is $N(C_1$-$C_6$ alkyl$)_2$, halogen or —$NO_2$. In some implementations, $R^4$ is hydrogen, halogen, $OR^{14}$, $NR^{14}R^{24}$, $SR^{14}$, $C_1$-$C_6$alkyl or —$NO_2$. For example, in some implementations, $R^4$ is hydrogen or halogen. In some implementations, $R^5$ is hydrogen, halogen, $OR^{14}$, $NR^{14}R^{24}$, $SR^{14}$, $C_1$-$C_6$alkyl or —$NO_2$. For example, optionally $R^5$ is hydrogen or halogen. In some implementations, $R^2$, $R^4$ and $R^5$ are hydrogen. In some implementations, $R^6$ is hydrogen, halogen, $OR^{14}$, $NR^{14}R^{24}$, $SR^{14}$, or $C_1$-$C_6$ alkyl. For example, in some implementations, $R^6$ is hydrogen, halogen or $OR^{14}$. In some implementations, $R^7$ is hydrogen, halogen, $OR^{14}$, $NR^{14}R^{24}$, or $C_1$-$C_6$ alkyl. For example, in some implementations, $R^7$ is hydrogen, halogen or $OR^{14}$. In some implementations, $R^{8'}$ is hydrogen, halogen, $OR^{14}$, $NR^{14}R^{24}$, $SR^{14}$, or $C_1$-$C_6$ alkyl. For example, in some implementations, le is H or F. In some implementations, $R^{9'}$ is hydrogen, halogen, $OR^{14}$, $NR^{14}R^{24}$, $SR^{14}$, or $C_1$-$C_6$ alkyl. For example, in some implementations, $R^{9'}$ is H or F. In some implementations, $R^{10}$ is hydrogen or $C_1$-$C_6$ alkyl. For example, in some implementations, $R^{10}$ is hydrogen. In some implementations, $R^{11}$ is hydrogen or $C_1$-$C_6$ alkyl. For example, in some implementations, $R^{11}$ is hydrogen. In some implementations, $R^{12}$ is hydrogen or $C_1$-$C_6$ alkyl. For example, in some implementations, $R^{12}$ is hydrogen. In some implementations, $R^{13}$ is hydrogen or $C_1$-$C_6$ alkyl. For example, in some implementations, $R^{13}$ is hydrogen. In some implementations, $R^{14}$ is hydrogen or $C_1$-$C_6$ alkyl. For example, in some implementations, $R^{14}$ is hydrogen. In some implementations at least one of $R^{11}$ and $R^{12}$ are hydrogen. In some implementations $R^{11}$ and $R^{12}$ are hydrogen. In some implementations at least one of $R^{13}$ and $R^{14}$ are hydrogen. In some implementations $R^{13}$ and $R^{14}$ are hydrogen. In some implementations $R^{11}$, $R^{12}$, $R^{13}$ and $R^{14}$ are hydrogen.

According to some implementations of compounds of Formula (I), at least one germinal pair of $R^{11}$, $R^{12}$, $R^{13}$ and $R^{14}$ together forms a carbonyl (=O).

According to some implementations of compounds of Formula (I), geminal $R^{11}$ and $R^{12}$ form a carbonyl providing the compound having the Formula (II):

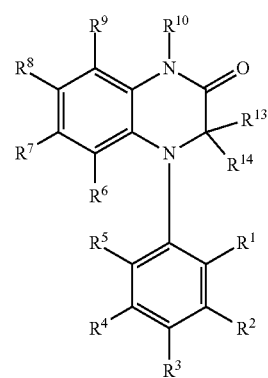

(II)

In compounds of Formula (II), any combination of $R^1$ through $R^{10}$, $R^{13}$ and $R^{14}$ can be independently selected. In some implementations, $R^1$ is hydrogen, halogen, $OR^{14}$, $NR^{14}R^{24}$, $SR^{14}$ $C_1$-$C_6$alkyl or —$NO_2$. For example, in some implementations, $R^1$ is $O(C_1$-$C_6$ alkyl). In some implementations, $R^2$ is hydrogen, halogen, $OR^{14}$, $NR^{14}R^{24}$, $SR^{14}$, $C_1$-$C_6$alkyl or —$NO_2$. For example, in some implementations, $R^2$ is hydrogen or halogen. In some implementation, $R^3$ is hydrogen, halogen, $OR^{14}$, $NR^{14}R^{24}$, $C_1$-$C_6$alkyl, $C_2$-$C_8$alkenyl, or —$NO_2$. For example, in some implementations, $R^3$ is $N(C_1$-$C_6$ alkyl)$_2$, halogen or —$NO_2$. In some implementations, $R^4$ is hydrogen, halogen, $OR^{14}$, $NR^{14}R^{24}$, $SR^{14}$, $C_1$-$C_6$alkyl or —$NO_2$. For example, in some implementations, $R^4$ is hydrogen or halogen. In some implementations, $R^5$ is hydrogen, halogen, $OR^{14}$, $NR^{14}R^{24}$, $SR^{14}$, $C_1$-$C_6$alkyl or —$NO_2$. For example, in some implementations, $R^5$ is hydrogen or halogen. In some implementations, $R^2$, $R^4$ and $R^5$ are hydrogen. In some implementations, $R^6$ is hydrogen, halogen, $OR^{14}$, $NR^{14}R^{24}$, $SR^{14}$, or $C_1$-$C_6$ alkyl. For example, in some implementations, $R^6$ is hydrogen, halogen or $OR^{14}$. In some implementations, $R^7$ is hydrogen, halogen, $OR^{14}$, $NR^{14}R^{24}$, $SR^{14}$, or $C_1$-$C_6$ alkyl. For example, in some implementations, $R^7$ is hydrogen, halogen or $OR^{14}$. In some implementations, $R^8$ is hydrogen, halogen, $OR^{14}$, $NR^{14}R^{24}$, $SR^{14}$, or $C_1$-$C_6$ alkyl. For example, in some implementations, $R^8$ is hydrogen, halogen or $OR^{14}$. In some implementations, $R^9$ is hydrogen, halogen, $OR^{14}$, $NR^{14}R^{24}$, $SR^{14}$, or $C_1$-$C_6$ alkyl. For example, in some implementations, $R^9$ is hydrogen, halogen or $OR^{14}$. In some implementations, $R^{10}$ is hydrogen or $C_1$-$C_6$ alkyl. For example, in some implementations, $R^{10}$ is hydrogen. In some implementations, $R^{13}$ is hydrogen or $C_1$-$C_6$ alkyl. For example, in some implementations, $R^{13}$ is hydrogen. In some implementations, $R^{14}$ is hydrogen or $C_1$-$C_6$ alkyl. For example, in some implementations, $R^{14}$ is hydrogen. In some implementations at least one of $R^{13}$ and $R^{14}$ are hydrogen. In some implementations $R^{13}$ and $R^{14}$ are hydrogen. In some implementations, $R^7$ and $R^8$ together with the carbons to which they are attached, form a 5-8 membered cycloalkyl or heterocycle ring. In some implementations, $R^7$ and $R^8$ together with the carbons to which they are attached to form an optionally substituted dioxolane, For example, in some implementations, the compound is of Formula (IIA) wherein n is, 1, 2 or 3, and $R^{7'}$ and $R^{8'}$ independently are hydrogen or halogen. In some implementations, $R^6$ and $R^7$ together with the carbons to which they are attached, form a 5-8 membered cycloalkyl or heterocycle ring. In some implementations, $R^6$ and $R^7$ together with the carbons to which they are attached to form an optionally substituted dioxolane. For example, in some implementations, the compound is of Formula (IIB) wherein n is, 1, 2 or 3, and $R^{6'}$ and $R^{7'}$ independently are hydrogen or halogen. In some implementations, $R^8$ and $R^9$ together with the carbons to which they are attached, form a 5-8 membered cycloalkyl or heterocycle ring. In some implementations, $R^8$ and $R^9$ together with the carbons to which they are attached to form an optionally substituted dioxolane. For example, in some implementations, the compound is of Formula (IIC) wherein n is, 1, 2 or 3, and $R^{8'}$ and $R^{9'}$ independently are hydrogen or halogen. In some implementations of compounds (IIA), (IIB) and (IIC), n is 1 or 2. In some implementations of compound (IIA) $R^{7'}$ is H or F. In some implementations of compound (IIA) $R^{8'}$ is H or F. In some implementations of compounds (IIB) $R^{6'}$ is H or F. In some implementations of compounds (JIB) $R^{7'}$ is H or F. In some implementations of compound (IIC) $R^{8'}$ is H or F. In some implementations of compound (IIC) $R^{9'}$ is H or F. In some implementations, the compound is (FQI-34Q). In some implementations, the compound is (FQI-37Q). In some implementations, the compound is (FQI-1Q). The compounds (IIA), (IIB), (IIC), (FQI-34Q), (FQI-37Q), and FQI-1Q) are:

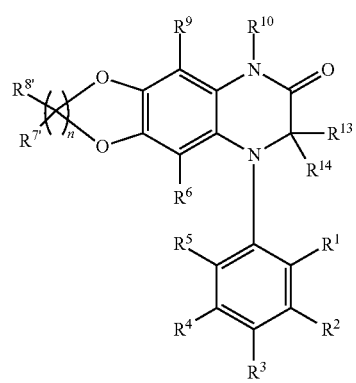

(IIA)

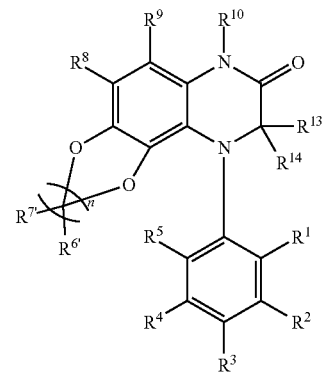

(IIB)

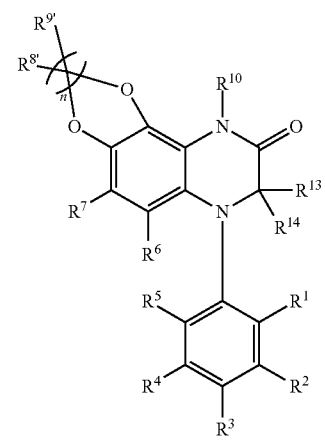

(IIC)

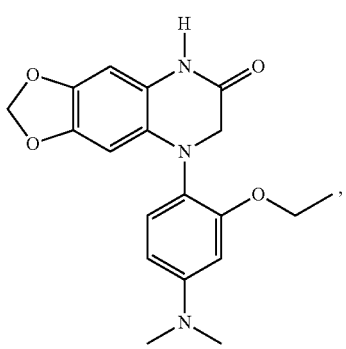

(FQI-34Q)

(FGI-37Q)

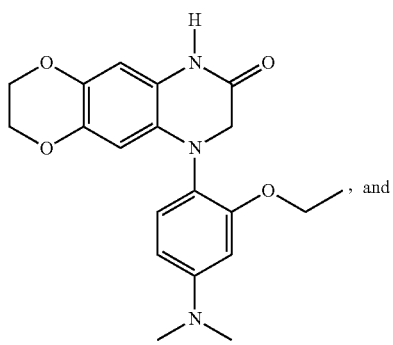

, and (FQI-1Q)

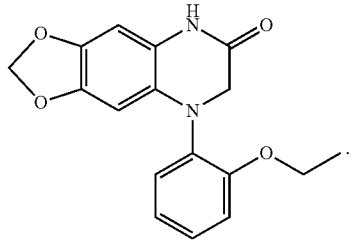

.

According to some implementations of the compounds of Formula (I), geminal $R^{13}$ and $R^{14}$ form a carbonyl providing the compound having the Formula (III):

(III)

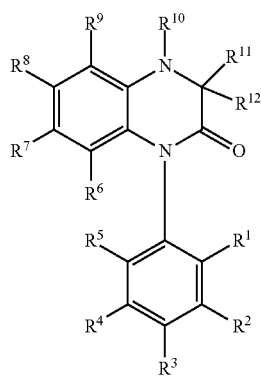

In compounds of Formula (III) any combination of $R^1$ through $R^{12}$ can be independently selected. In some implementations, $R^1$ is hydrogen, halogen, $OR^{1A}$, $NR^{1A}R^{2A}$, $SR^{1A}$, $C_1$-$C_6$alkyl or —$NO_2$. For example, in some implementations, $R^1$ is $O(C_1$-$C_6$ alkyl). In some implementations, $R^2$ is hydrogen, halogen, $OR^{1A}$, $NR^{1A}R^{2A}$, $SR^{1A}$, $C_1$-$C_6$alkyl or —$NO_2$. For example, in some implementations, $R^2$ is hydrogen or halogen. In some implementation, $R^3$ is hydrogen, halogen, $OR^{1A}$, $NR^{1A}R^{2A}$, $C_1$-$C_6$alkyl, $C_2$-$C_8$alkenyl, or —$NO_2$. For example, in some implementations, $R^3$ is $N(C_1$-$C_6$ alkyl)$_2$, halogen or —$NO_2$. In some implementations, $R^4$ is hydrogen, halogen, $OR^{1A}$, $NR^{1A}R^{2A}$, $SR^{1A}$, $C_1$-$C_6$alkyl or —$NO_2$. For example, in some implementations, $R^4$ is hydrogen or halogen. In some implementations, $R^5$ is hydrogen, halogen, $OR^{1A}$, $NR^{1A}R^{2A}$, $SR^{1A}$, $C_1$-$C_6$alkyl or —$NO_2$. For example, in some implementations, $R^5$ is hydrogen or halogen. In some implementations, $R^2$, $R^4$ and $R^5$ are hydrogen. In some implementations, $R^6$ is hydrogen, halogen, $OR^{1A}$, $NR^{1A}R^{2A}$, $SR^{1A}$, or $C_1$-$C_6$ alkyl. For example, in some implementations, $R^6$ is hydrogen, halogen or $OR^{1A}$. In some implementations, $R^7$ is hydrogen, halogen, $OR^{1A}$, $NR^{1A}R^{2A}$, $SR^{1A}$, or $C_1$-$C_6$ alkyl. For example, in some implementations, $R^7$ is hydrogen, halogen or $OR^{1A}$. In some implementations, $R^8$ is hydrogen, halogen, $OR^{1A}$, $NR^{1A}R^{2A}$, $SR^{1A}$, or $C_1$-$C_6$ alkyl. For example, in some implementations, $R^8$ is hydrogen, halogen or $OR^{1A}$. In some implementations, $R^9$ is hydrogen, halogen, $OR^{1A}$, $NR^{1A}R^{2A}$, $SR^{1A}$, or $C_1$-$C_6$ alkyl. For example, in some implementations, $R^9$ is hydrogen, halogen or $OR^{1A}$. In some implementations, $R^{10}$ is hydrogen or $C_1$-$C_6$ alkyl. For example, in some implementations, $R^{10}$ is hydrogen. In some implementations, $R^{11}$ is hydrogen or $C_1$-$C_6$ alkyl. For example, in some implementations, $R^{11}$ is hydrogen. In some implementations, $R^{12}$ is hydrogen or $C_1$-$C_6$ alkyl. For example, in some implementations, $R^{12}$ is hydrogen. In some implementations at least one of $R^{11}$ and $R^{12}$ are hydrogen. In some implementations $R^{11}$ and $R^{12}$ are hydrogen. In some implementations, $R^7$ and $R^8$ together with the carbons to which they are attached, form a 5-8 membered cycloalkyl or heterocycle ring. In some implementations, $R^7$ and $R^8$ together with the carbons to which they are attached to form an optionally substituted dioxolane. For example, in some implementations, the compound is of Formula (IIIA) wherein n is, 1, 2 or 3, and $R^{7'}$ and $R^{8'}$ independently are hydrogen or halogen. In some implementations, $R^6$ and $R^7$ together with the carbons to which they are attached, form a 5-8 membered cycloalkyl or heterocycle ring. In some implementations, $R^6$ and $R^7$ together with the carbons to which they are attached to form an optionally substituted dioxolane. For example, in some implementations, the compound is of Formula (IIIB) wherein n is, 1, 2 or 3, and $R^{6'}$ and $R^{7'}$ independently are hydrogen or halogen. In some implementations, $R^8$ and $R^9$ together with the carbons to which they are attached, form a 5-8 membered cycloalkyl or heterocycle ring. In some implementations, $R^8$ and $R^9$ together with the carbons to which they are attached to form an optionally substituted dioxolane. For example, in some implementations, the compound is of Formula (IIIC) wherein n is, 1, 2 or 3, and $R^{8'}$ and $R^{9'}$ independently are hydrogen or halogen. In some implementations of compounds (IIIA), (IIIB) and (IIIC), n is 1 or 2. In some implementations of compound (IIIA) $R^{7'}$ is H or F. In some implementations of compound (IIIA) $R^{8'}$ is H or F. In some implementations of compounds (IIIB) $R^{6'}$ is H or F. In some implementations of compounds (IIIB) $R^{7'}$ is H or F. In some implementations of compound (IIIC) $R^{8'}$ is H or F. In some implementations of compound (IIIC) $R^{9'}$ is H or F. Where the compounds (IIIA), (IIIB), and (IIIC) are:

(IIIA)

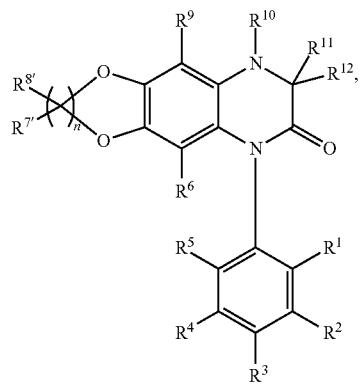

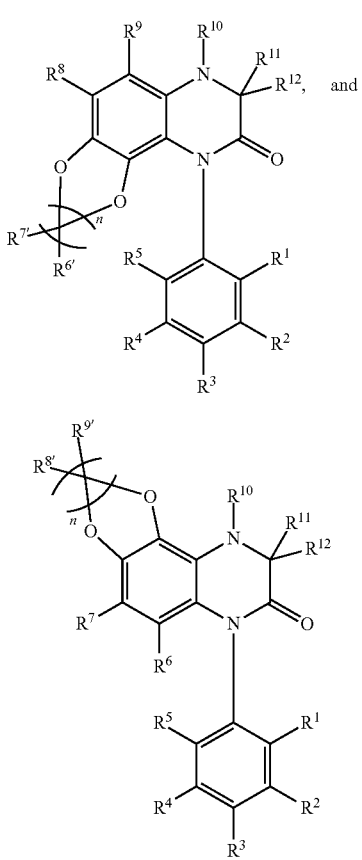

In in some implementations of compounds of Formula (I), both geminal $R^{11}$ and $R^{12}$, and geminal $R^{13}$ and $R^{14}$ form a carbonyls providing the compound having the Formula (IV):

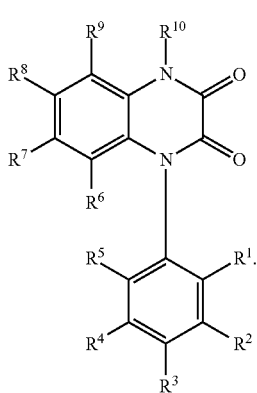

In compound of Formula (IV) any combination of $R^1$ through $R^{10}$ can be independently selected. In some implementations, $R^1$ is hydrogen, halogen, $OR^{1A}$, $NR^{1A}R^{2A}$, $SR^{1A}$, $C_1$-$C_6$alkyl or $-NO_2$. For example, in some implementations, $R^1$ is $O(C_1$-$C_6$ alkyl). In some implementations, $R^2$ is hydrogen, halogen, $OR^{1A}$, $NR^{1A}R^{2A}$, $SR^{1A}$, $C_1$-$C_6$alkyl or $-NO_2$. For example, in some implementations, $R^2$ is hydrogen or halogen. In some implementation, $R^3$ is hydrogen, halogen, $OR^{1A}$, $NR^{1A}R^{2A}$ $C_1$-$C_6$alkyl, $C_2$-$C_8$alkenyl, or $-NO_2$. For example, in some implementations, $R^3$ is $N(C_1$-$C_6$ alkyl)$_2$, halogen or $-NO_2$. In some implementations, $R^4$ is hydrogen, halogen, $OR^{1A}$, $NR^{1A}R^{2A}$, $SR^{1A}$, $C_1$-$C_6$alkyl or $-NO_2$. For example, in some implementations, $R^4$ is hydrogen or halogen. In some implementations, $R^5$ is hydrogen, halogen, $OR^{1A}$, $NR^{1A}R^{2A}$, $SR^{1A}$, $C_1$-$C_6$alkyl or $-NO_2$. For example, in some implementations, $R^5$ is hydrogen or halogen. In some implementations, $R^2$, $R^4$ and $R^5$ are hydrogen. In some implementations, $R^6$ is hydrogen, halogen, $OR^{1A}$, $NR^{1A}R^{2A}$, $SR^{1A}$, or $C_1$-$C_6$ alkyl. For example, in some implementations, $R^6$ is hydrogen, halogen or $OR^{1A}$. In some implementations, $R^7$ is hydrogen, halogen, $OR^{1A}$, $NR^{1A}R^{2A}$, $SR^{1A}$, or $C_1$-$C_6$ alkyl. For example, in some implementations, $R^7$ is hydrogen, halogen or $OR^{1A}$. In some implementations, $R^8$ is hydrogen, halogen, $OR^{1A}$, $NR^{1A}R^{2A}$, $SR^{1A}$, or $C_1$-$C_6$ alkyl. For example, in some implementations, $R^8$ is hydrogen, halogen or $OR^{1A}$. In some implementations, $R^9$ is hydrogen, halogen, $OR^{1A}$, $NR^{1A}R^{2A}$, $SR^{1A}$, or $C_1$-$C_6$ alkyl. For example, in some implementations, $R^9$ is hydrogen, halogen or $OR^{1A}$. In some implementations, $R^{10}$ is hydrogen or $C_1$-$C_6$ alkyl. For example, in some implementations, $R^{10}$ is hydrogen. In some implementations, $R^7$ and $R^8$ together with the carbons to which they are attached, form a 5-8 membered cycloalkyl or heterocycle ring. In some implementations, $R^7$ and $R^8$ together with the carbons to which they are attached to form an optionally substituted dioxolane. For example, in some implementations, the compound is of Formula (IVA) wherein n is, 1, 2 or 3, and $R^{7'}$ and $R^{8'}$ independently are hydrogen or halogen. In some implementations, $R^6$ and $R^7$ together with the carbons to which they are attached, form a 5-8 membered cycloalkyl or heterocycle ring. In some implementations, $R^6$ and $R^7$ together with the carbons to which they are attached to form an optionally substituted dioxolane. For example, in some implementations, the compound is of Formula (IVB) wherein n is, 1, 2 or 3, and $R^{6'}$ and $R^{7'}$ independently are hydrogen or halogen. In some implementations, $R^8$ and $R^9$ together with the carbons to which they are attached, form a 5-8 membered cycloalkyl or heterocycle ring. In some implementations, $R^8$ and $R^9$ together with the carbons to which they are attached to form an optionally substituted dioxolane. For example, in some implementations, the compound is of Formula (IVC) wherein n is, 1, 2 or 3, and $R^{8'}$ and $R^{9'}$ independently are hydrogen or halogen. In some implementations of compounds (IVA), (IVB) and (IVC), n is 1 or 2. In some implementations of compound (IVA) $R^{7'}$ is H or F. In some implementations of compound (IVA) $R^{8'}$ is H or F. In some implementations of compounds (IVB) $R^{6'}$ is H or F. In some implementations of compounds (IVB) $R^{7'}$ is H or F. In some implementations of compound (IVC) $R^{8'}$ is H or F. In some implementations of compound (IVC) $R^{9'}$ is H or F. Where the compounds of Formula (IVA), (IVB), and (IVC) are:

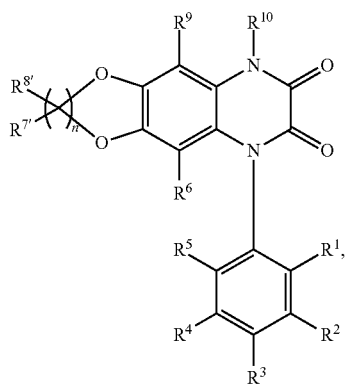

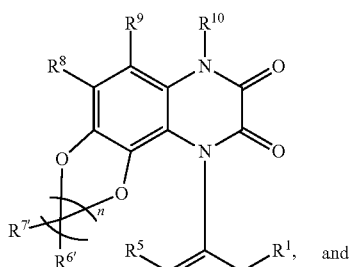

(IVB)

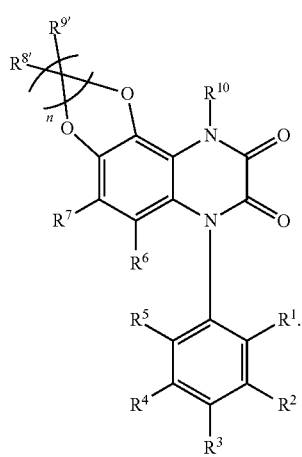

(IVC)

In some implementations, $R^{12}$ and $R^{14}$ together form a double bond between the carbon atoms they are attached to providing the compound having the Formula (V):

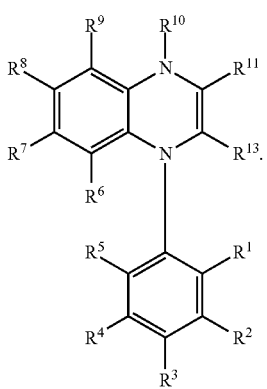

(V)

In compound of Formula (V), any combination of $R^1$ through $R^{11}$ and $R^{13}$ can be independently selected. In some implementations, $R^1$ is hydrogen, halogen, $OR^{14}$, $NR^{14}R^{24}$, $SR^{14}$ $C_1$-$C_6$alkyl or —$NO_2$. For example, in some implementations, $R^1$ is $O(C_1$-$C_6$ alkyl). In some implementations, $R^2$ is hydrogen, halogen, $OR^{14}$, $NR^{14}R^{24}$, $SR^{14}$, $C_1$-$C_6$alkyl or —$NO_2$. For example, in some implementations, $R^2$ is hydrogen or halogen. In some implementation, $R^3$ is hydrogen, halogen, $OR^{14}$, $NR^{14}R^{24}$, $C_1$-$C_6$alkyl, $C_2$-$C_8$alkenyl, or —$NO_2$. For example, in some implementations, $R^3$ is $N(C_1$-$C_6$ alkyl)$_2$, halogen or —$NO_2$. In some implementations, $R^4$ is hydrogen, halogen, $OR^{14}$, $NR^{14}R^{24}$, $SR^{14}$, $C_1$-$C_6$alkyl or —$NO_2$. For example, in some implementations, $R^4$ is hydrogen or halogen. In some implementations, $R^5$ is hydrogen, halogen, $OR^{14}$, $NR^{14}R^{24}$, $SR^{14}$, $C_1$-$C_6$alkyl or —$NO_2$. For example, in some implementations, $R^5$ is hydrogen or halogen. In some implementations, $R^2$, $R^4$ and $R^5$ are hydrogen. In some implementations, $R^6$ is hydrogen, halogen, $OR^{14}$, $NR^{14}R^{24}$, $SR^{14}$, or $C_1$-$C_6$ alkyl. For example, in some implementations, $R^6$ is hydrogen, halogen or $OR^{14}$. In some implementations, $R^7$ is hydrogen, halogen, $OR^{14}$, $NR^{14}R^{24}$, $SR^{14}$, or $C_1$-$C_6$ alkyl. For example, in some implementations, $R^7$ is hydrogen, halogen or $OR^{14}$. In some implementations, $R^8$ is hydrogen, halogen, $OR^{14}$, $NR^{14}R^{24}$, $SR^{14}$, or $C_1$-$C_6$ alkyl. For example, in some implementations, $R^8$ is hydrogen, halogen or $OR^{14}$. In some implementations, $R^9$ is hydrogen, halogen, $OR^{14}$, $NR^{14}R^{24}$, $SR^{14}$, or $C_1$-$C_6$ alkyl. For example, in some implementations, $R^9$ is hydrogen, halogen or $OR^{14}$. In some implementations, $R^{10}$ is hydrogen or $C_1$-$C_6$ alkyl. For example, in some implementations, $R^{10}$ is hydrogen. In some implementations, $R^{11}$ is hydrogen or $C_1$-$C_6$ alkyl. For example, in some implementations, $R^{11}$ is hydrogen. In some implementations at least one of $R^{11}$ and $R^{13}$ are hydrogen. In some implementations $R^{11}$ and $R^{13}$ are hydrogen. In some implementations, $R^7$ and $R^8$ together with the carbons to which they are attached, form a 5-8 membered cycloalkyl or heterocycle ring. In some implementations, $R^7$ and $R^8$ together with the carbons to which they are attached to form an optionally substituted dioxolane. For example, in some implementations, the compound is of Formula (VA) wherein n is, 1, 2 or 3, and $R^{7'}$ and $R^{8'}$ independently are hydrogen or halogen. In some implementations, $R^6$ and $R^7$ together with the carbons to which they are attached, form a 5-8 membered cycloalkyl or heterocycle ring. In some implementations, $R^6$ and $R^7$ together with the carbons to which they are attached to form an optionally substituted dioxolane. For example, in some implementations, the compound is of Formula (VB) wherein n is, 1, 2 or 3, and $R^{6'}$ and $R^{7'}$ independently are hydrogen or halogen. In some implementations, $R^8$ and $R^9$ together with the carbons to which they are attached, form a 5-8 membered cycloalkyl or heterocycle ring. In some implementations, $R^8$ and $R^9$ together with the carbons to which they are attached to form an optionally substituted dioxolane. For example, in some implementations, the compound is of Formula (VC) wherein n is, 1, 2 or 3, and $R^{8'}$ and $R^{9'}$ independently are hydrogen or halogen. In some implementations of compounds (VA), (VB) and (VC), n is 1 or 2. In some implementations of compound (VA) $R^{7'}$ is H or F. In some implementations of compound (VA) $R^{8'}$ is H or F. In some implementations of compounds (VB) $R^{6'}$ is H or F. In some implementations of compound (VB) $R^{7'}$ is H or F. In some implementations of compound (VC) $R^{8'}$ is H or F. In some implementations of compound (VC) $R^{9'}$ is H or F. Where the compounds of Formula (VA), (VB), and (VC) are:

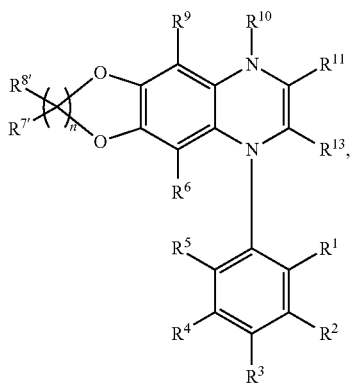

(VA)

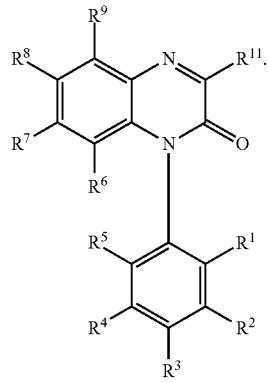

(VI)

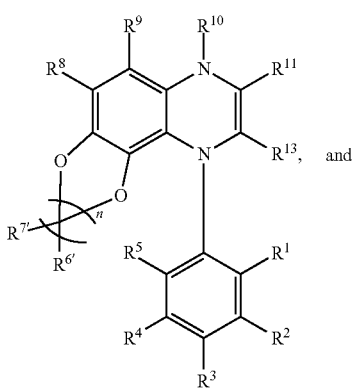

(VB)

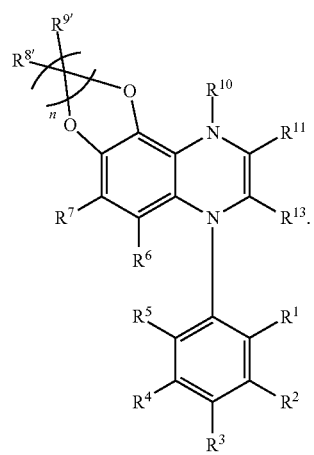

(VC)

In some implementations, vicinal $R^{10}$ and $R^{12}$ together form a double bond between the carbon atoms they are attached, and geminal R13 and R14 together form a carbonyl (C=O). In this implementation, the compound has Formula (VI):

In compound of Formula (VI), any combination of $R^1$ through $R^9$ and $R^{11}$ can be independently selected. In some implementations, $R^1$ is hydrogen, halogen, $OR^{1A}$, $NR^{1A}R^{2A}$, $SR^{1A}$, $C_1$-$C_6$alkyl or —$NO_2$. For example, in some implementations, $R^1$ is $O(C_1$-$C_6$ alkyl). In some implementations, $R^2$ is hydrogen, halogen, $OR^{1A}$, $NR^{1A}R^{2A}$, $SR^{1A}$, $C_1$-$C_6$alkyl or —$NO_2$. For example, in some implementations, $R^2$ is hydrogen or halogen. In some implementation, $R^3$ is hydrogen, halogen, $OR^{1A}$, $NR^{1A}R^{2A}$, $C_1$-$C_6$alkyl, $C_2$-$C_8$alkenyl, or —$NO_2$. For example, in some implementations, $R^3$ is $N(C_1$-$C_6$ alkyl)$_2$, halogen or —$NO_2$. In some implementations, $R^4$ is hydrogen, halogen, $OR^{1A}$, $NR^{1A}R^{2A}$ $SR^{1A}$, $C_1$-$C_6$alkyl or —$NO_2$. For example, in some implementations, $R^4$ is hydrogen or halogen. In some implementations, $R^5$ is hydrogen, halogen, $OR^{1A}$, $NR^{1A}R^{2A}$, $SR^{1A}$, $C_1$-$C_6$alkyl or —$NO_2$. For example, in some implementations, $R^5$ is hydrogen or halogen. In some implementations, $R^2$, $R^4$ and $R^5$ are hydrogen. In some implementations, $R^6$ is hydrogen, halogen, $OR^{1A}$, $NR^{1A}R^{2A}$, $SR^{1A}$, or $C_1$-$C_6$ alkyl. For example, in some implementations, $R^6$ is hydrogen, halogen or $OR^{1A}$. In some implementations, $R^7$ is hydrogen, halogen, $OR^{1A}$, $NR^{1A}R^{2A}$, $SR^{1A}$, or $C_1$-$C_6$ alkyl. For example, in some implementations, $R^7$ is hydrogen, halogen or $OR^{1A}$. In some implementations, $R^8$ is hydrogen, halogen, $OR^{1A}$, $NR^{1A}R^{2A}$, $SR^{1A}$, or $C_1$-$C_6$ alkyl. For example, in some implementations, $R^8$ is hydrogen, halogen or $OR^{1A}$. In some implementations, $R^9$ is hydrogen, halogen, $OR^{1A}$, $NR^{1A}R^{2A}$, $SR^{1A}$, or $C_1$-$C_6$ alkyl. For example, in some implementations, $R^9$ is hydrogen, halogen or $OR^{1A}$. In some implementations, $R^{11}$ is hydrogen or $C_1$-$C_6$ alkyl. For example, in some implementations, $R^{11}$ is hydrogen. In some implementations, $R^7$ and $R^8$ together with the carbons to which they are attached, form a 5-8 membered cycloalkyl or heterocycle ring. In some implementations, $R^7$ and $R^8$ together with the carbons to which they are attached to form an optionally substituted dioxolane. For example, in some implementations, the compound is of Formula (VIA) wherein n is, 1, 2 or 3, and $R^{7'}$ and $R^{8'}$ independently are hydrogen or halogen. In some implementations, $R^6$ and $R^7$ together with the carbons to which they are attached, form a 5-8 membered cycloalkyl or heterocycle ring. In some implementations, $R^6$ and $R^7$ together with the carbons to which they are attached to form an optionally substituted dioxolane. For example, in some implementations, the compound is of Formula (VIB) wherein n is, 1, 2 or 3, and $R^{6'}$ and $R^{7'}$ independently are hydrogen or halogen. In some implementations, $R^8$ and $R^9$ together with the carbons to which they are attached, form a 5-8 membered cycloalkyl or heterocycle ring. In some implementations, $R^8$ and $R^9$ together with the carbons to which they are attached to form an optionally substituted dioxolane. For example, in some implementations, the compound is of Formula (VIC) wherein n is, 1, 2 or 3, and $R^{8'}$ and $R^{9'}$ independently are hydrogen or halogen. In some implementations of compounds (VIA), (VIB) and (VIC), n is 1 or 2. In some implementations of compound (VIA) $R^{7'}$ is H or F. In some implementations of compound (VIA) $R^{8'}$ is H or F. In some implementations of compounds (VIB) $R^{6'}$ is H or F. In some implementations of compounds (VIB) $R^{7'}$ is H or F. In some implementations of compound (VIC) $R^{8'}$ is H or F. In some implementations of compound (VIC) $R^{9'}$ is H or F. In some implementations, the compound is (JAK 196-22). In some implementations, the compound is (JAK 196.23). Where the compounds of Formula (VIA), (VIB), (VIC), (JAK 196-22) and (JAK 196.23) are:

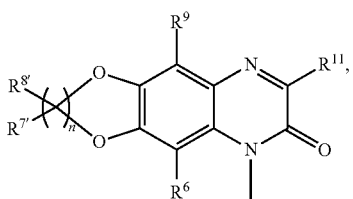
(VIA)

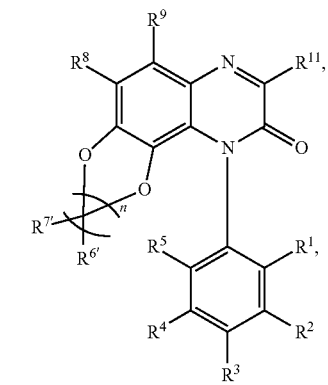
(VIB)

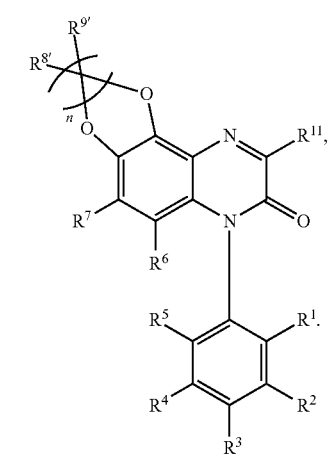
(VIC)

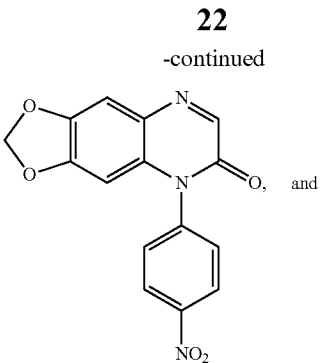
(JAK 196-22)

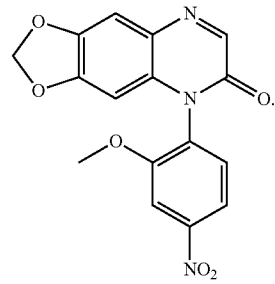
(JAK 196.23)

In some implementations, vicinal $R^{10}$ and $R^{12}$ together form a double bond between the carbon atoms they are attached, providing the compound having Formula (VII):

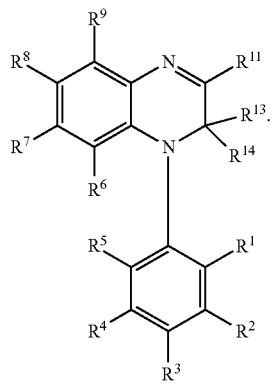
(VII)

In compound of Formula (VII), any combination of $R^1$ through $R^9$, $R^{11}$, $R^{13}$ and $R^{14}$ can be independently selected. In some implementations, $R^1$ is hydrogen, halogen, $OR^{1A}$, $NR^{1A}R^{2A}$, $SR^{1A}$, $C_1$-$C_6$alkyl or —$NO_2$. For example, in some implementations, $R^1$ is $O(C_1$-$C_6$ alkyl). In some implementations, $R^2$ is hydrogen, halogen, $OR^{1A}$, $NR^{1A}R^{2A}$, $SR^{1A}$, $C_1$-$C_6$alkyl or —$NO_2$. For example, in some implementations, $R^2$ is hydrogen or halogen. In some implementation, $R^3$ is hydrogen, halogen, $OR^{1A}$, $NR^{1A}R^{2A}$, $C_1$-$C_6$alkyl, $C_2$-$C_8$alkenyl, or —$NO_2$. For example, in some implementations, $R^3$ is $N(C_1$-$C_6$ alkyl$)_2$, halogen or —$NO_2$. In some implementations, $R^4$ is hydrogen, halogen, $OR^{1A}$, $NR^{1A}R^{2A}$, $SR^{1A}$, $C_1$-$C_6$alkyl or —$NO_2$. For example, in some implementations, $R^4$ is hydrogen or halogen. In some implementations, $R^5$ is hydrogen, halogen, $OR^{1A}$, $NR^{1A}R^{2A}$, $SR^{1A}$, $C_1$-$C_6$alkyl or —$NO_2$. For example, in some implementations, $R^5$ is hydrogen or halogen. In some implementations, $R^2$, $R^4$ and $R^5$ are hydrogen. In some implementations, $R^6$ is hydrogen, halogen, $OR^{1A}$, $NR^{1A}R^{2A}$, $SR^{1A}$, or $C_1$-$C_6$ alkyl. For example, in some implementations, $R^6$ is hydrogen, halogen or OR$^{14}$. In some implementations, R$^7$ is hydrogen, halogen, OR$^{14}$, NR$^{14}$R$^{24}$, SR$^{14}$, or C$_1$-C$_6$ alkyl. For example, in some implementations, R$^7$ is hydrogen, halogen or OR$^{14}$. In some implementations, R$^8$ is hydrogen, halogen, OR$^{14}$, NR$^{14}$R$^{24}$, SR$^{14}$, or C$_1$-C$_6$ alkyl. For example, in some implementations, R$^8$ is hydrogen, halogen or OR$^{14}$. In some implementations, R$^9$ is hydrogen, halogen, OR$^{14}$, NR$^{14}$R$^{24}$, SR$^{14}$, or C$_1$-C$_6$ alkyl. For example, in some implementations, R$^9$ is hydrogen, halogen or OR$^{14}$. In some implementations, R$^{11}$ is hydrogen or C$_1$-C$_6$ alkyl. For example, in some implementations, R$^{11}$ is hydrogen. In some implementations, R$^{13}$ is hydrogen or C$_1$-C$_6$ alkyl. For example, in some implementations, R$^{13}$ is hydrogen. In some implementations, R$^{14}$ is hydrogen or C$_1$-C$_6$ alkyl. For example, in some implementations, R$^{14}$ is hydrogen. In some implementations, R$^7$ and R$^8$ together with the carbons to which they are attached, form a 5-8 membered cycloalkyl or heterocycle ring. In some implementations, R$^7$ and R$^8$ together with the carbons to which they are attached to form an optionally substituted dioxolane. For example, in some implementations, the compound is of Formula (VIIA) wherein n is, 1, 2 or 3, and R$^{7'}$ and R$^{8'}$ independently are hydrogen or halogen. In some implementations, R$^6$ and R$^7$ together with the carbons to which they are attached, form a 5-8 membered cycloalkyl or heterocycle ring. In some implementations, R$^6$ and R$^7$ together with the carbons to which they are attached to form an optionally substituted dioxolane. For example, in some implementations, the compound is of Formula (VIIB) wherein n is, 1, 2 or 3, and R$^{6'}$ and R$^{7'}$ independently are hydrogen or halogen. In some implementations, R$^8$ and R$^9$ together with the carbons to which they are attached, form a 5-8 membered cycloalkyl or heterocycle ring. In some implementations, R$^8$ and R$^9$ together with the carbons to which they are attached to form an optionally substituted dioxolane. For example, in some implementations, the compound is of Formula (VIIC) wherein n is, 1, 2 or 3, and R$^{8'}$ and R$^{9'}$ independently are hydrogen or halogen. In some implementations of compounds (VIIA), (VIIB) and (VIIC), n is 1 or 2. In some implementations of compound (VIIA) R$^{7'}$ is H or F. In some implementations of compound (VIIA) R$^{8'}$ is H or F. In some implementations of compounds (VIIB) R$^{6'}$ is H or F. In some implementations of compounds (VIB) R$^{7'}$ is H or F. In some implementations of compound (VIIC) R$^{8'}$ is H or F. In some implementations of compound (VIIC) R$^{9'}$ is H or F. Where the compounds of Formula (VIIA), (VIIB), and (VIIC) are:

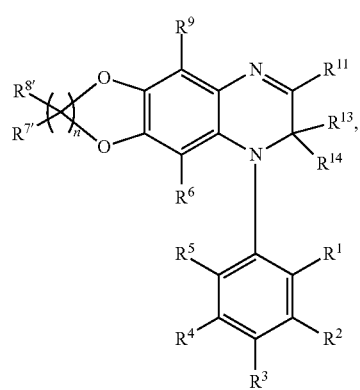

(VIIA)

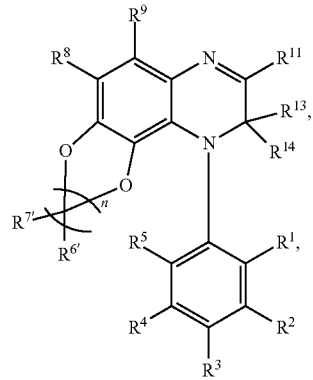

(VIIB)

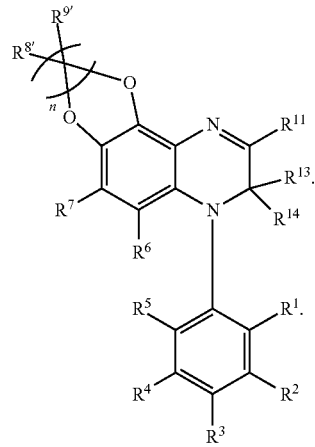

(VIIC)

According to some implementations of the description is a method for making compounds of Formula (I). For example, in some implementations the method includes a method of making compound (II). Compound (II) can be further reacted, such as by alkylation to provide compounds of Formula (I). In some implementations, a method of preparing a compound of Formula (II) includes providing a first compound and a second compound in a first solution, and reacting the first compound with the second compound. The first compound has the Formula (IX) and the second compound has the Formula (X):

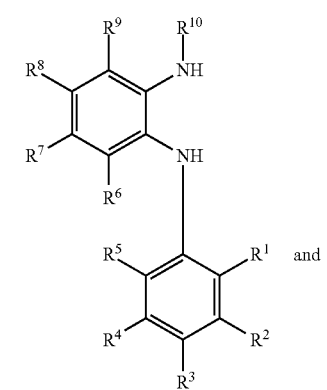

(IX) and

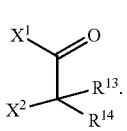

(X)

In compounds of Formula (X), $X^1$ and $X^2$ are each independently selected from $C_l$, Br or I; and $R^{13}$ and $R^{14}$ together form a carbonyl (=O), or are each independently selected from the group consisting of hydrogen, halogen, $C_1$-$C_6$ alkyl, $C_1$-$C_6$ haloalkyl, $C_1$-$C_6$ heteroalkyl, $OR^{3A}$, $SR^{3A}$, $SO_2R^{3A}$, $NR^{3A}R^{4A}$, halogen, heteroaryl, and aryl. In compounds of Formula (IX) none, one, or more vicinal pairs of $R^1$, $R^2$, $R^3$, $R^4$, $R^5$, $R^6$, $R^7$, $R^8$, and $R^9$ each, together with the carbons to which they are attached, form a 5-8 membered cycloalkyl or heterocyle ring; and the remaining $R^1$, $R^2$, $R^3$, $R^4$, $R^5$, $R^6$, $R^7$, $R^8$, or $R^9$ are each independently selected from the group consisting of hydrogen, halogen, $OR^{1A}$, $NR^{1A}R^{2A}$, $SR^{1A}$, $SO_2R^{1A}$, —$NO_2$, $C_1$-$C_6$ alkyl, $C_1$-$C_6$ haloalkyl, $C_1$-$C_6$ heteroalkyl, aryl, and heteroaryl. Also in Formula (IX) $R^{10}$ is hydrogen, $C_1$-$C_6$ alkyl, $C_1$-$C_6$ haloalkyl, $C_1$-$C_6$ heteroalkyl, aryl, heteroaryl, or halogen. In Formula (IX) $R^{1A}$, $R^{2A}$, $R^{3A}$, and $R^{4A}$ are each independently selected from the group consisting of hydrogen, $C_1$-$C_8$ alkyl, $C_2$-$C_8$ alkenyl, $C_2$-$C_8$ alkynyl, cycloalkyl, heterocyclyl, $C_1$-$C_8$ haloalkyl, $C_1$-$C_8$ heteroalkyl, heteroaryl, and aryl, wherein the alkyl, alkenyl, alkynyl, cycloalkyl, heterocyclyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl or $C_1$-$C_6$ alkoxy. Also in Formula (IX), any of the 5-8 membered cycloalkyl, the heterocyle ring, the alkyl, the haloalkyl, the heteroalkyl, the heteroaryl, and the aryl can be optionally substituted with halogen, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono($C_1$-$C_6$ alkyl)amino or di($C_1$-$C_6$ alkyl)amino.

In some implementations, the first compound (IX) and second compound (X) react to form an intermediate compound (XI):

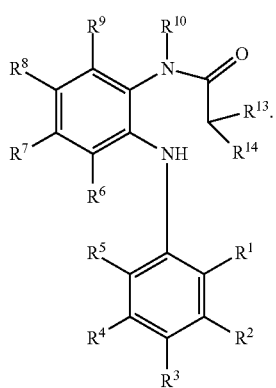

(XI)

In some implementations the intermediate compound of Formula (XI) is concentrated. For example, in some implementations, at least a portion of the first solution is removed e.g. in vacuo. In some implementations, the intermediate is isolated, for example by precipitation, crystallization, filtration, sublimation, chromatographic separation, preparatory HPLC, evaporation of the solvent, or combinations of these. In some implementations, the intermediate is not isolated and is reacted in a one-pot reaction only using the first solvent, optionally with concentration of the first solvent after the first step producing the intermediate (VI). In some implementations, the intermediate compound (XI) is isolated and then combined with a second solution. The first and second solution can include the same or a different solvent. In some implementations, the solvent is selected from tetrahydrofuran (THF), 2-methyl-THF, 1,8-Diazabicyclo[5.4.0]undec-7-ene (DBU), triethyl amine, diethyl ether, t-butyl ether, acetone, an mixtures of these. The intermediate compound (XI) undergoes a cyclization reaction providing the compound (II). In some implementations, the cyclization reaction done under heating conditions, such as refluxing the solvent.

In some implementations, the first compound having Formula (IX) having R10=H is provided by coupling a nitro aromatic compound of Formula (XII) with an aromatic amine of Formula (XIII):

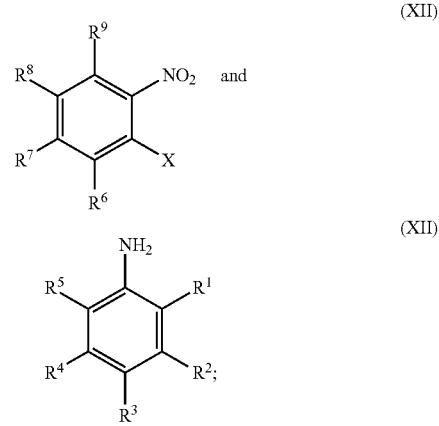

wherein X is a halide (e.g. Br).

The nitro aromatic compound of Formula (XII) and aromatic amine of Formula (XIII) are combined in a third solvent and coupled, for example using a palladium catalyst coupling the amine to the carbon attached to the halide (X). In some implementations, a portion of the third solvent is removed (e.g., in vacuo). The coupled product is reduced, for example, by provided a reducing solution. The reducing solution can include the third solution and hydrogen, such as an atmosphere of hydrogen or hydrogen bubbling in the solution. Reaction reduces the nitro group, providing the first compound (IX) having $R^{10}$=hydrogen.

According to some implementations, the present disclosure provides a pharmaceutical composition including a compound selected from the group consisting of compounds of Formula (I) and a pharmaceutically acceptable excipient or carrier. In some implementations, the compound of Formula (I) is formulated with the pharmaceutically acceptable excipient or carrier for administration to a subject orally, subcutaneously, parenterally, topically, rectally, by intravenous injection or by subcutaneous injection. According to some implementations, a pharmaceutically acceptable derivative includes, but is not limited to, pharmaceutically acceptable salts, esters, salts of such esters, or a pro-drug or other adduct or derivative of a compounds of Formula (I) which upon administration to a patient in need is capable of providing, directly or indirectly, a compound as otherwise described herein, or a metabolite or residue thereof. In some implementations, the compound is selected from the group consisting of compounds of Formula (II). In some implementations, the compound is selected from the group consisting of compounds of Formula (IIA). In some implementations, the compound is (FQI-37Q). In some implementations, the compound is (FQI-34Q). In some implementations, the compound is (FQI-1Q).

Amount of compounds of Formula (I) in the pharmaceutical composition can be based on weight, moles, or volume. In some implementations, the pharmaceutical composition comprises at least 0.0001% of compounds of Formula (I). In some implementations, the pharmaceutical composition comprises at least 0.1% of compounds of Formula. In some implementations, the pharmaceutical composition comprises at least 0.5% of compounds of Formula (I). In some implementations, the pharmaceutical composition comprises at least 1% of compounds of Formula (I). In some implementations, the pharmaceutical composition comprises at least 2% of compounds of Formula. In some implementations, the pharmaceutical composition comprises at least 3% of compounds of Formula. In some implementations, the pharmaceutical composition comprises at least 4% of compounds of Formula. In some implementations, the pharmaceutical composition comprises at least 5% of compounds of Formula. In some implementations, the pharmaceutical composition comprises at least 10% of compounds of Formula (I). In some implementations, the pharmaceutical composition comprises 0.01%-99% of the compounds of Formula (I). In some implementations, the pharmaceutical composition comprises 0.05%-90% of the compounds of Formula (I). In some implementations, the pharmaceutical composition comprises 0.1%-85% of the compounds of Formula (I). In some implementations, the pharmaceutical composition comprises 0.5%-80% of the compounds of Formula (I). In some implementations, the pharmaceutical composition comprises 1%-75% of the compounds of Formula (I). In some implementations, the pharmaceutical composition comprises 2% 70% of the compounds of Formula. In some implementations, the pharmaceutical composition comprises 3%-65% of the compounds of Formula (I). In some implementations, the pharmaceutical composition comprises 4%-60% of the compounds of Formula (I). In some implementations, the pharmaceutical composition comprises 5%-50% of the compounds of Formula (I).

As described above, the pharmaceutical compositions in some implementations optionally comprise a pharmaceutically acceptable excipient, which, as used herein, includes any and all solvents, diluents, or other liquid vehicle, dispersion or suspension aids, surface active agents, isotonic agents, thickening or emulsifying agents, preservatives, antioxidants, solid binders, lubricants, and the like, as suited to the particular dosage form desired.

According to some implementations, the present disclosure is a method to inhibit late SV40 factor or late Simian Virus 40 factor (LSF) in a subject. LSF is also known as aliases LBP-1c (leader binding protein-1c), LBP-1d, SEF (SAA3 enhancer factor), TFCP2 (transcription factor CP2) and CP2. The method includes administering an effective amount of the compound of Formula (I) or a pharmaceutical composition including the compound of Formula (I) to a subject in need thereof. In some implementations, the compound is selected from the group consisting of compounds of Formula (II). In some implementations, the compound is selected from the group consisting of compounds of Formula (IIA). In some implementations, the compound (FQI-37Q). In some implementations, the compound (FQI-34Q). In some implementations, compound (FQI-1Q).

Inhibiting LSF has previously shown to inhibit growth or proliferation of cells. Accordingly, another aspect of the present invention relates to a method of inhibiting growth or proliferation of a cell, e.g., a cell expressing LSF, the method comprising administering to the cell an effective amount of a compound of Formula (I).

Inhibiting LSF has previously shown to abrogate LSF-tubulin interactions in cells, and disrupt mitotic spindle formation via a non-transcriptional mechanism. See, for example, U.S. patent application Ser. No. 16/530,080, content of which is incorporated by reference in its entirety. Accordingly, yet another aspect of the present invention relates to a method of inhibiting tubulin methylation or modulating chromatin/cytoskeleton modification in a cell, the method comprising administering to the cell an effective amount of a compound of Formula (I).

It is noted that administering to the cell can be in vino or in-vivo. Methods for administering a compound to a cell are well known and available to one of skill in the art. As used herein, administering the compound to the cell means contacting the cell with the compound so that the compound is taken up by the cell. Generally, the cell can be contacted with the compound in a cell culture e.g., in vitro or ex vivo, or the compound can be administrated to a subject, e.g., in vivo. The term "contacting" or "contact" as used herein in connection with contacting a cell includes subjecting the cells to an appropriate culture media, which comprises a compound of Formula (I). Where the cell is in vivo, "contacting" or "contact" includes administering the compound, e.g., in a pharmaceutical composition to a subject via an appropriate administration route such that the compound contacts the cell in vivo.

For example, when the cell is in vitro, said administering to the cell can include subjecting the cell to an appropriate culture media which comprises the indicated compound. Where the cell is in vivo, said administering to the cell includes administering the compound to a subject via an appropriate administration route such that the compound is administered to the cell in vivo.

The cell to be administered a compound of Formula (I) can be any desired cell expressing LSF. For example, the cell can be a mammalian cell, e.g., a human cell. In some embodiments of any one of the aspects, the cell is a liver cell. For example, the cell to be administered a compound of Formula (I) can be a hepatocyte, in some embodiments, the cell can be a cancer cell or tumor cell.

In some implementations, the subject in need of treatment to inhibit LSF suffers or is at risk of cancer. In some implementations, the cancer is HCC. In some implementations, the cancer is selected from the group consisting of breast cancer, colon cancer, ovarian cancer, lung cancer, kidney cancer, cancers of the hematopoietic system, cancers of the endometrium, cervical cancer, cancers of the upper digestive tract, stomach cancer, pancreatic cancer, liver cancers and cancers of the small intestine. In some implementations, the method further comprises administering an additional anti cancer therapy to the subject. In some implementations, the subject suffers from or is at risk of HIV or is in need of lower inflammatory responses. In some implementations, the administering is topical, enteral, or parenteral. In some implementations, the administering is oral, intravenous injection or subcutaneous injection. In some implementations, the subject is human.

LSF is a DNA-binding transcription factor that is required in multiple cell types for cell cycle progression and regulates diverse cellular and viral promoters. It binds to the alpha-globin promoter and activates transcription of the alpha-globin gene. It has been reported that LSF facilitates entry into G1/S phase of the cell cycle, promotes DNA synthesis, and functions as an antiapoptotic factor. LSF also regulates erythroid gene expression, plays a role in the transcriptional switch of globin gene promoters, and it activates many other cellular and viral gene promoters. The gene product interacts with certain inflammatory response factors, and polymorphisms of this gene can be involved in the pathogenesis of Alzheimer's disease.

A major cellular target of LSF is the thymidylate synthase (TS) gene (TYMS), which encodes the rate-limiting enzyme in the production of dTTP, required for DNA synthesis. TS has been a long-standing chemotherapeutic target for cancer treatments, and recently it was discussed that elevated levels of LSF in hepatocellular carcinoma cell lines can contribute to chemoresistance to one commonly utilized thymidylate synthetase inhibitor, 5-fluorouracil. Inhibition of LSF abrogates TS induction, induces either arrest at the G1/S transition, or in apoptosis after entry into S phase. Thus, LSF plays an important role in DNA synthesis and cell survival. In the liver, LSF is activated by inflammatory cytokines and regulates the expression of acute phase proteins.

In some implementations, the genes downstream of LSF are tumor-associated genes, such as relating to invasion and metastasis, angiogenesis, epithelial-mesenchymal transition (EMT), cell growth, drug metabolism, senescence, cell adhesion, glycolysis, Wnt signaling, Hippo signaling, growth and regeneration, inflammatory response, e.g. acute phase proteins, and modulators of matrix-degrading enzymes e.g. MMP9. LSF is a transcription factor encoded by TFCP2. Thus, inhibiting LSF can disrupt or inhibit LSF binding to DNA and/or interaction of LSF with other proteins to form a complex.

Accordingly, in some implementations, inhibition of cellular LSF activity can be determined by measuring the level of downstream genes regulated by the transcription factor LSF. The effect of LSF on expression (level) of LSF-targeted or LSF-downstream genes can be stimulatory or inhibitory. For example, one gene induced by LSF is SPP1 encoding OPN. Thus, an inhibition of biological activity of LSF results in a decrease in level of SPP1 mRNA and/or a decrease in the amount of the respective encoded protein, OPN. In another implementation, one gene inhibited by LSF is TAGLN. Thus, an inhibition of biological activity of LSF leads to an increase in level of TAGLN mRNA. In some implementations, the cellular activity of LSF can be measured by a reduction in the level of TS.

In further implementations, inhibition of LSF can decrease expression of LSF, for example, a reduction in protein level, and/or a decrease in gene transcript level (e.g. mRNA) of LSF.

As disclosed herein, inhibitors of LSF can decrease functional transcriptional activity or the expression of LSF (e.g., such as protein level of LSF, and/or gene transcript level of LSF), by at least about 10%, at least about 15%, at least about 20%, at least about 30%, at least about 40%, at least about 50%, at least about 60%, at least about 70%, at least about 80%, at least about 90%, 95%, 99% or even 100%, as compared to the expression in the absence of inhibitors of LSF. The expression of LSF can be measured by standard methods known to a skilled artisan such as western blot, ELISA, and quantitative PCR as well as the methods provided in Examples section.

In some implementations, inhibitors of LSF as disclosed herein can inhibit or decrease cellular LSF activity by at least about 10%, relative to the activity level in the absence of inhibitors of LSF, e.g., at least about 15%, at least about 20%, at least about 30%, at least about 40%, at least about 50%, at least about 60%, at least about 70%, at least about 80%, at least about 90%, 95%, 99% or even 100%. In certain implementations, inhibitors of LSF as disclosed herein can decrease expression of downstream genes up-regulated by LSF, e.g. SPP1 encoding OPN, by about at least 10%, at least about 15%, at least about 20%, at least about 30%, at least about 40%, at least about 50%, at least about 60%, at least about 70%, at least about 80%, at least about 90%, 95%, 99% or even 100%, as compared to the expression in the absence of inhibitors of LSF. In alternative implementations, inhibitors of LSF can increase expression of downstream genes down-regulated by LSF, e.g. TAGLN, by about at least 10%, at least about 15%, at least about 20%, at least about 30%, at least about 40%, at least about 50%, at least about 60%, at least about 70%, at least about 80%, at least about 90%, 95%, 99% or even 100%, as compared to the expression in the absence of inhibitors of LSF.

Inhibition of LSF has been previously discussed as a potential treatment of latent HIV infection or cancer in general, or as a therapeutic regulator of immune function, specifically when there is a need thereof to decrease inflammatory response (U.S. Patent Application No.: US 2009/0081183 and International Patent Application No.: WO1998/36641, which are incorporated herein in their entirety by reference). However, these patent applications do not teach or describe any small-molecule LSF inhibitors of the invention as disclosed herein, or the use thereof for treatment of hepatocellular carcinoma (HCC). Small-molecule LSF inhibitors have been described (U.S. Pat. No. 10,393,398, which is incorporated herein in their entirety by reference). However, this patent describes chiral compounds which add complexity to their preparation.

The ability of a compound to inhibit LSF can be assessed in some instances by measuring a decrease in expression of LSF as compared to the level of LSF in the absence of inhibitors of LSF. In some implementations, the ability of a compound to inhibit LSF can be assessed by measuring a decrease in the biological activity, e.g., transcriptional activity of LSF as compared to the level of transcriptional activity of LSF in the absence of inhibitors of LSF. The expression of LSF includes the amount of RNA transcribed from a gene, e.g. TFCP2 that encodes LSF, and/or the amount of LSF proteins that is obtained by translation of RNA transcribed from a gene, e.g. TFCP2. For example, a LSF inhibitor as disclosed herein can inhibit expression of LSF by at least about 10%, at least about 15%, at least about 20%, at least about 30%, at least about 40%, at least about 50%, at least about 60%, at least about 70%, at least about 80%, at least about 90%, 95%, 99% or even 100%, as compared to a reference level in the absence of a LSF inhibitor.

Additionally, ability of a compound to inhibit LSF can be also assessed by measuring a decrease in or an inhibition of biological activity of LSF as compared to a negative control, e.g. the experimental condition in the absence of LSF inhibitors. The biological activity of LSF can refer to the ability of LSF to modulate expression of LSF-targeted genes such as thymidylate synthase (TYMS) and/or LSF-downstream genes, such as secreted phosphoprotein 1 (SPP1), complement factor H (CFH) and other tumor-associated genes (see Yoo et al., PNAS, 2010, 107; 8357-8362, which is incorporated herein in its entirety by reference). Accordingly, a LSF inhibitor as disclosed herein can inhibit biological activity of LSF, such as a decrease in expression of SPP1 that encodes OPN (also known as secreted phosphoprotein 1, SPP1), by at least about 10%, at least about 15%, at least about 20%, at least about 30%, at least about 40%, at least about 50%, at least about 60%, at least about 70%, at least about 80%, at least about 90%, 95%, 99% or even 100%, as compared to a reference level in the absence of a LSF inhibitor. In some implementations, ability of a compound to inhibit LSF is assessed by inhibition of LSF-induced tumorigenesis and metastasis of cancer cells, e.g. hepatocellular carcinoma cells in vitro or in an in vivo animal model as demonstrated in WO2012/050985, U.S. Pat. Nos. 9,802,948, 9,815,845 and 9,597,325, contents of all which are incorporated herein by reference in their entirety, as compared to a reference condition without treatment with such a LSF inhibitor. In such implementations, a LSF inhibitor can decrease a tumor weight and volume by at least about 15%, at least about 20%, at least about 30%, at least about 40%, at least about 50%, at least about 60%, at least about 70%, at least about 80%, at least about 90%, 95%, 99% or even 100%, as compared to no treatment with a LSF inhibitor.

It was previously reported in Yoo et al., (PNAS, 2010; 107; 8357-8362) that the level of LSF expression is useful to identify a subject with HCC. Accordingly, a subject amenable to treatment using the methods and compositions as disclosed herein can be identified by measuring the level of LSF in a biological sample obtained from the subject and if the level of LSF in the biological sample from the subject is higher by a statistically significant amount relative to a reference level of LSF, the subject likely is at risk of having HCC, and accordingly, can be administered a composition comprising at least one small molecule inhibitor of LSF selected from any of Formula (I) as disclosed herein.

A subject is identified as suffering from HCC or having a disordered characterized by increased LSF expression, when the expression level of LSF in a biological sample obtained from the subject is higher relative to a reference level of LSF by at least about 20%, at least about 30%, at least about 40%, at least about 50%, at least about 60%, at least about 70%, at least about 80%, at least about 90%, at least about 95%, at least about 98%, about 99% or about 100%. The extent of increase in LSF expression can indicate the grades and stages of HCC (See Yoo et al., PNAS, 2010; 107; 8357-8362). Accordingly, subjects identified with HCC or having a disorder characterized by increased LSF expression can be treated with an effective dose of a pharmaceutical composition as disclosed herein comprising a LSF inhibitor selected from any of Formula (I) as disclosed herein to inhibit or delay progression of HCC.

In some implementations, a biological sample is a tissue sample, e.g. a liver sample.

In some implementations, the level of LSF in a biological sample is compared to a reference level, or a reference biological sample, such as a biological sample from adjacent liver tissue (not pathologically abnormal, or such as biological sample obtained from an age-matched normal control (e.g. an age-matched subject not having HCC or an age-matched normal healthy subject).

In other implementations, in order to determine the therapeutic efficacy of the treatment (e.g. treatment of HCC), a reference level can be the level of LSF expression or the level of expression of LSF target genes measured at a previous time point from the same subject on a treatment regimen.

The methods according to some implementations of the description also are useful for monitoring a course of treatment being administered to a subject. The methods can be used to monitor both therapeutic treatment on symptomatic subject and prophylactic treatment on asymptomatic subject.

A treatment administered to a subject is considered to be effective if the level of expression of LSF or of LSF target genes in a biological sample obtained from the subject is decreased relative to a reference level of LSF by at least about 20%, at least about 30%, at least about 40%, at least about 50%, at least about 60%, at least about 70%, at least about 80%, at least about 90%, at least about 95%, at least about 98%, about 99% or about 100%. In such implementations, the reference level is the measurement of LSF or of LSF target genes at a previous time point from the same subject who has been administered to the treatment regimen. Based on the outcome of treatment, the dosage and frequency of administration using the methods and compositions as disclosed herein can be adjusted accordingly by one of skill in the art.

In one implementation, the biological sample for analysis is a liver sample, wherein the sample comprises at least one cell. One can use any immunoassay to determine the level of LSF or of LSF target genes in a biological sample, such as ELISA or immunohistochemical methods of detecting LSF or LSF target genes which are commonly known in the art and are encompassed for use according to some implementations.

In some implementations, a method of determining the presence and/or level of LSF in a biological sample from a subject comprises performing a binding assay. Any reasonably specific binding partner can be used. For example, the binding partner is labeled. For example, the assay is an immunoassay, especially between LSF and an antibody that recognizes LSF, especially a labeled antibody. It can be an antibody raised against part or all of it, such as a monoclonal antibody or a polyclonal antiserum of high specificity for LSF. In some implementations, the antibodies is specific to mammalian LSF, such as human LSF.

Thus, any anti-LSF antibody can be used in the method to determine the presence and/or level of LSF in a biological sample, which can be used to detect the increased or decreased level of LSF present in a diagnostic sample. Such antibodies can be raised by any of the methods well known in the immunodiagnostics field.

In some implementations, an immunoassay is carried out by measuring the extent of the protein/antibody interaction of the LSF/antibody interaction. Any known method of immunoassay may be used. In some implementations, a sandwich assay or ELISA is used. In this method, a first antibody to the marker protein is bound to the solid phase such as a well of a plastics microtitre plate, and incubated with the sample and with a labeled second antibody specific to the protein to be assayed. Alternatively, an antibody capture assay could be used. In some implementations, a biological test sample is allowed to bind to a solid phase, and the anti-LSF protein antibody is then added and allowed to bind. After washing away unbound material, the amount of antibody bound to the solid phase is determined using a labeled second antibody against the first.

In some implementations, a label is preferably an enzyme. The substrate for the enzyme may be, for example, color-forming, fluorescent or chemiluminescent.

In some implementations, a binding partner, e.g. an antibody or a ligand binding to LSF in the binding assay is preferably a labeled specific binding partner, but not necessarily an antibody. The binding partner will usually be labeled itself, but alternatively it may be detected by a secondary reaction in which a signal is generated, e.g. from another labeled substance.

In some implementations, one can use an amplified form of assay, whereby an enhanced "signal" is produced from a relatively low level of protein to be detected. One particular form of amplified immunoassay is enhanced chemiluminescent assay. Conveniently, the antibody is labeled with horseradish peroxidase, which participates in a chemiluminescent reaction with luminol, a peroxide substrate and a compound which enhances the intensity and duration of the emitted light, typically 4-iodophenol or 4-hydroxycinnamic acid.

In another implementation, an amplified immunoassay can be used which is immuno-PCR. In this technique, the antibody is covalently linked to a molecule of arbitrary DNA comprising PCR primers, whereby the DNA with the antibody attached to it is amplified by the polymerase chain reaction. See E. R. Hendrickson et al., Nucleic Acids Research 23: 522-529 (1995). The signal is read out as before.

Alternatively, in some implementations, one method to determine the level of LSF in a biological sample is to use a two dimensional gel electrophoresis to yield a stained gel and the increased or decreased level of the protein detected by an increased an increased or decreased intensity of a protein-containing spot on the stained gel, compared with a corresponding control or comparative gel.

In some implementations, methods to determine the amount of LSF in a biological sample does not necessarily require a step of comparison of the level of LSF with a control sample (e.g. from a normal healthy subject), but it can be carried out with reference either to a control or a comparative sample. Thus, in relation to HCC, measuring the amount of LSF in a biological sample can be used to determine the stage of progression, if desired with reference to results obtained earlier from the same subject or by reference to standard values that are considered typical of the stage of the disease. In this way, the methods can be used to determine whether, for example after treatment of the subject with a LSF inhibitor, the disease has progressed or not. The result can lead to a prognosis of the outcome of the disease.

In some implementations, one method to detect the presence and/or the level of LSF in a biological sample is to perform immunohistochemical assay on a biopsy sample, such as a liver sample. The methods for detecting the presence and/or a level of protein on a biopsy sample are well within the level of skill in the art. In alternative implementations, the mRNA level of LSF in a biological sample is determined by quantitative PCR with primers designed according to the nucleotide sequence of LSF. The design for primers of LSF can be performed easily by one of the skill in the art.

In various implementations, the level of LSF can be measured and used in combination with other biomarkers for HCC such as AFP to diagnose HCC in a subject. Other biomarkers for HCC include, but not limited to, those described, for example, in US 2013/0107227, content of which is incorporated herein by reference in its entirety.

In some implementations, a compound of Formula (I) as disclosed herein can be used for therapeutic or prophylactic treatment of various cancers in a subject in need thereof. In some implementations, the cancer is liver cancer (hepatocellular carcinoma-HCC). In some implementations, the cancer is selected from the group consisting of breast cancer, colon cancer, ovarian cancer, lung cancer, kidney cancer, cancers of the hematopoietic system, cancers of the endometrium, cervical cancer, cancers of the upper digestive tract, stomach cancer, pancreatic cancer, liver cancers and cancers of the small intestine. In some implementations, the method further comprises administering an additional anti-cancer therapy to the subject. In some implementations, the subject suffers from, or is at risk of HIV. In some implementations the subject suffers from or is at risk of an inflammation-related diseases such as hepatitis B virus (HBV), hepatitis C (HCV), cirrhosis and Alzheimer's disease. In some implementations, the liver diseases can be any selected from, but not limited to, HBV, HCV, cirrhosis, hepatic adenoma, hepatic angiosarcoma and hepatic angiosarcomas; emphysema; and hereditary hemochromatosis. In some implementations, the administering is topical, enteral, or parenteral. In some implementations, the administering is oral, intravenous injection or subcutaneous injection. In some implementations, the subject is human. In some implementations, the compound is selected from the group consisting of compounds of Formula (II). In some implementations, the compound is selected from the group consisting of compounds of Formula (IIA). In some implementations, the compound (FQI-37Q). In some implementations, the compound (FQI-34Q). In some implementations, compound (FQI-1Q).

In some implementations, a compound of Formula (I) as disclosed herein can be used to treat other cancers, for example, brain cancer, head and neck squamous cell carcinoma, pancreatic cancer, ductal adenocarcinoma, colorectal adenocarcinoma, rectosigmoid carcinoma, kidney cancer, monocytic lymphoma, ovarian cancer, and thyroid cancer melanomas and the like. Other cancers which can be treated include any cancer with overexpression of LSF in the tumor, for example, but not limited to, oligodendroglioma, meningioma, GBM, breast cancer, colon cancer, Non-Hodgkin's small cell carcinoma (HNSCC), lung cancer (adrenocarcinomas), lung cancer (small cell carcinoma), pancreatic cancer, ovarian cancer, thyroid cancer and undifferentiated cancer.

In some implementations, a compound of Formula (I) as disclosed herein can be used to treat any cancer cell type. Cancers include, but are not limited to, bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS associated leukemias and adult T-cell leukemia lymphoma; intraepithelial neoplasms including Bowen's disease and Paget's disease, liver cancer; lung cancer including small cell lung cancer and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilm's tumor.

In some implementations, a compound of Formula (I) as disclosed herein is used to treat a subject with hepatocellular carcinoma (HCC). In another implementation, a subject at high risk of developing HCC is suitable for treatment with the compositions of the invention comprising at least a LSF inhibitor as disclosed herein.

Hepatocellular carcinoma (HCC) is one of the five most common cancers worldwide. The incidence of HCC is increasing despite a decrease in overall incidence of all cancers. In the United States, the estimated new cases of HCC for 2008 were 21,370, of which 18,410 were expected to die. The mean 5-year survival rate is less than 10%. The mortality rate of HCC parallels that of its incidence because HCC is a tumor with rapid growth and early vascular invasion that is resistant to conventional chemotherapy, and only suboptimal systemic therapy is available for the advanced disease.

To date, other than curative resection, treatments for HCC have had minimal impact on survival. Unfortunately, approximately 90% of HCC patients have unresectable HCC. Moreover, even after potentially curative hepatectomy in patients with resectable HCC, new HCC arises in the cirrhotic remnants in 70% of these patients, and frequently arises in the grafted liver following orthotopic liver transplantation. Other approaches to treating HCC, such as intralesional ethanol injection, chemoembolization, radiofrequency ablation, cryosurgery and radiation therapy have demonstrated some success in selected patient populations; however, the efficacies of these approaches have not been definitively established. Both percutaneous intralesional ethanol injection and transarterial chemoembolization have shown limited success, but not without risks of serious side effects. Radiotherapy is not usually an option because liver is very radiosensitive.

All systemic therapies for HCC to date are associated with uniformly poor outcomes, and only two chemotherapeutic agents (sorafenib and regorafenib), alone or in combination with other treatments, have been associated with any improvement in survival rates (Fuchs et al., 94 Cancer 3186 (2002) and Bruix et al., Lancet (2017), 389(10064), 56-66). In addition, most patients with HCC have underlying liver disease so their ability to tolerate to undergo surgery is compromised. Therefore, there is a strong need in the art to provide improved methods for treatment of HCC.

In some implementations, compounds of Formula (I) or a pharmaceutical composition thereof as disclosed herein can be used in conjunction with other therapeutic treatment of HCC such as hepatointralesional ethanol injection, chemoembolization, radiofrequency ablation, cryosurgery, radiation therapy, percutaneous intralesional ethanol injection, transarterial chemoembolization, and radiotherapy.

In some implementations of the various aspects disclosed herein, the composition or method can further comprise administering an additional anti-cancer therapy to the subject. For example, administering a standard of care chemotherapeutic to the subject. Non-limiting examples of a standard of care chemotherapeutics or other anti-cancer therapy can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX);

lapatinib (Tykerb®); inhibitors of PKC-alpha, Raf, H-Ras, EGFR (e.g., erlotinib (TARCEVA®)) and VEGF-A that reduce cell proliferation and pharmaceutically acceptable salts, acids or derivatives of any of the above. Additional anti-cancer treatment can further include the use of radiation or radiation therapy. Further, the additional anti-cancer treatment can also include the use of surgical treatments.

In some implementations of the various aspects disclosed herein, the treatment is administered to a subject currently receiving standard of care chemotherapeutics or other alternative anti-cancer treatments. Generally, cancer treatment may involve one or more of the treatment options, but not limited to surgery, radiation, chemotherapy, immunotherapy, targeted therapy and hormonal therapy. The single agent therapy or current combination therapies for the treatment of cancer cause side effects such as nausea, rashes, swelling, flu-like symptoms, fatigue, digestive tract problems, allergic reactions and immunosuppression. In some implementations, the treatments described herein provides a more effective treatment of cancer by administering one or more compounds represented by Formula (I) in combination with other cancer treatments. In some implementations, the combination therapy induces additive or synergistic therapeutic effect. In some implementations, the method described herein can reduce or prevent one or more adverse effects or toxicities associated with the administration of a chemotherapeutic agent or radiation therapy. In some implementations, the method described herein can increase the anti-tumor activity of a chemotherapeutic agent or radiation therapy or increase the selective cytotoxicity of a chemotherapeutic agent.

The phrase "combination therapy" as described herein means administration of one or more compounds represented by Formula (I) and a therapeutic agent as part of a specific treatment regimen intended to provide a beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period. The time period may be in minutes, hours, days or weeks depending upon the combination selected.

Combination therapy includes administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be done, for example, by administering to the subject a single pill having a fixed ratio of each therapeutic agent or in multiple, single pills for each of the therapeutic agents. Sequential or substantially simultaneous administration of each therapeutic agent can be effected by any appropriate route including, but not limited to, oral routes, intravenous routes, subcutaneous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered may or may not be important.

Combination therapy also can mean the administration of one or more compounds represented by Formula (I) in further combination with other compounds and non-drug therapies, such as, but not limited to, surgery or radiation treatment. Where the combination therapy further comprises radiation treatment, the radiation treatment may be conducted at any suitable time so long as a beneficial effect from the co-action of the combination of the therapeutic agents and radiation treatment is achieved.

In some implementations, compounds represented by Formula (I) as disclosed herein or a pharmaceutical composition thereof can be used to treat HCC subjects who are not responsive to any prior treatment of HCC, or show little/no improvement from any prior treatment of HCC, e.g. continued progression or worsening of HCC. In such implementations, the HCC subjects can be treated again with the previous therapeutic method in combination with an inhibitor of LSF. In alternative implementations, they can be administered with a LSF inhibitor or a pharmaceutical composition thereof alone, or concurrently with alternative therapeutic methods.

It has been previously reported that LSF is a downstream gene of astrocyte elevated gene-1 (AEG-1), which is overexpressed in >90% of human HCC patients and induces chemoresistance of HCC to a chemotherapeutic agent, such as 5-fluorouracil (5-FU). Accordingly, in some implementations, an inhibitor of LSF described herein can be administered prior to, or concurrently with at least one chemotherapeutic agent such as 5-FU. Other exemplary chemotherapeutic agents include Doxorubicin, 5-FU, Paclitaxel, Irinotecan, Patupilone, Everolimus, multikinase inhibitors (Sorafenib and Sunitinib), and EGFR inhibitors (Cetuximab, Erlotinib, Gefitinib, Brivanib, Lapatinib). In one implementation, a LSF inhibitor or a pharmaceutical composition thereof as disclosed herein can be combined with Sorafenib for treatment of HCC.

As a prophylactic measure against HCC recurrence or metastasis, compounds represented by Formula (I) as disclosed herein or a pharmaceutical composition thereof can be administered after surgery or after aforementioned treatments for HCC where solid tumors have been removed or eliminated. In some implementations, subjects with resectable HCC can be treated with any of compounds represented by Formula (I) or a pharmaceutical composition thereof after hepatectomy or liver transplantation to prevent the recurrence of HCC.

Most cases of HCC are developed from either chronic infection with hepatitis B or hepatitis C virus (HBV or HCV, respectively), or hepatic cirrhosis due to alcoholism. Chronic hepatitis can progress into cirrhosis (a noncancerous liver disease associated with fibrosis and abnormal nodules), which increases the risk of developing HCC. Subjects with chronic hepatitis and/or cirrhosis, therefore form a high risk population. Accordingly, in some implementations, any of compounds represented by Formula (I) can be used in conjunction with other therapeutic treatment for liver diseases such as infection with HBV, HCV or cirrhosis, as a preventive measure against the onset of HCC.

In some implementations, any of compounds of Formula (I) as disclosed herein can be administered to a subject with a high risk of developing hepatocellular carcinoma. For example, subjects amenable to treatment by methods and compositions as disclosed herein, e.g. using an inhibitor of LSF, are subjects having a risk factor for HCC. Examples of risk factors for HCC include, but not limited to, HBV, HCV, chronic alcohol consumption, exposure to aflatoxin B1 in food (which is a liver carcinogenic chemical produced by a mold called *Aspergillus flavus* after exposure of food to a hot and humid environment), hepatic adenoma resulted from the use of female hormones (estrogens) and protein-building (anabolic) steroids, exposure to thorotrast (a previously used contrast agent for imaging, which caused a cancer of the blood vessels in the liver called hepatic angiosarcoma), hepatic angiosarcomas (resulted from a prolonged exposure to vinyl chloride, a compound used in the plastics industry), hereditary hemochromatosis (a disorder that causes the body to accumulate excessive amounts of iron), emphysema and cirrhosis (resulted from alpha 1 anti-trypsin deficiency) and hereditary tyrosinemia. In some implementations, a LSF inhibitor can be used alone or combined with other therapeutic treatment of the aforementioned diseases or disorders. In further implementations, subjects who have been previously subjected to high risk of developing HCC can be continually treated with an inhibitor of LSF or a pharmaceutical composition thereof, even after they have discontinued treatment of liver diseases such as HBV, HCV or cirrhosis.

Other indications that can be contemplated for the use of LSF inhibitors as disclosed herein include diseases or disorders, in which expression and/or biological activity of LSF is up-regulated, e.g. by inflammatory cytokines, or in which it is desirable to decrease or inhibit LSF. Non-limiting examples of such diseases or disorders include HIV and inflammation-associated diseases including Alzheimer's disease.

It has been previously reported that LSF activates cell survival-regulating pathways, such as MEK/ERK and NF-κB pathways, and is up-regulated in various cancers (see Yoo et al., PNAS, 2010, 107; 8357-8362 and Kotarba et al., Cancer Lett. (2018), 28 (420), 72-79). Accordingly, in some implementations, a LSF inhibitor disclosed herein can be used alone or in combination with chemotherapeutic agents for treatment of other various cancers such as brain cancer, breast cancer, colon cancer, cervical cancer, head and neck squamous cell carcinoma, lung cancer, pancreatic cancer, ovarian cancer, and thyroid cancer. Exemplary chemotherapeutic agents include Doxorubicin, 5-FU, Paclitaxel, Irinotecan, Patupilone, Everolimus, multikinase inhibitors (Sorafenib and Sunitinib), and EGFR inhibitors (Cetuximab, Erlotinib, Gefitinib, Brivanib, Lapatinib). In some implementations, diseases or disorders associated with LSF-induced MEK/ERK activation can be contemplated for treatment with a LSF inhibitor as disclosed herein alone or in combination with inhibitors of MEK/ERK pathway such as PD98059 and U0126.

In some implementations, a subject amenable or suitable for treatment with a composition comprising any of compounds of Formula (I) as disclosed herein can be selected based on an increased level of LSF expression in a biological sample, or tumor or cancer sample as compared to a control reference LSF expression level, e.g., in a normal non-cancerous sample. In some implementations, a subject is at risk of having a cancer if the level of LSF expression in the biological sample from the subject is above a pre-determined reference LSF expression threshold level. In some implementations, the reference LSF expression threshold level is based on the level of LSF expression in a non-cancer cell or non-tumor tissue, or a control cell line, or cells from a normal tissue sample, where the tissue sample is from adjacent, non-pathological tissue of the subject, or a biological tissue sample from a tissue matched, and species matched and age matched biological sample. In some implementations, the reference level is based on a reference sample is from a non-cancer matched tissue sample.

In some implementations, the level of LSF expression is measured in a biological sample comprising a tumor sample. In some implementations, a biological sample obtained from the subject comprises cancer cells, and can be a biological sample which is serum plasma, blood or tissue sample. In some implementations, a biological sample is selected from the group consisting of; a tissue sample; a tumor sample; a tumor cell; a biopsy sample; ex vivo cultivated sample; ex vivo cultivated tumor sample; surgically dissected tissue sample, blood sample, plasma sample, cancer sample, lymph fluid sample or primary ascite sample. In alternative implementations, the biological sample includes, for example blood, plasma, serum, urine, spinal fluid, plural fluid, nipple aspirates, lymph fluid, external secretions of the skin, respiratory, internal and genitoururinary tracts, bile, tears, sweat, saliva, organs, milk cells and primary ascite cells, biopsy tissue sample, a cancer biopsy tissue sample, an in vitro or ex vivo cultivated biopsy tissue sample.

Screening for HCC: In some implementations, a subject amenable to treatment according to the methods as disclosed herein is screened for HCC. A convention biomarker for HCC is alpha-fetoproteins (AFP). Yang et al., 123 J. Cancer Res Clin Oncol. 357 (1997). Individuals with elevated serum levels of AFP can be an indication of hepatocellular carcinoma. Other biomarkers for HCC include, but not limited to, the ones disclosed in the U.S. Patent Application Nos.: US2009/0317844, US2010/0015605, US 2010/0120631, and International Patent Application Nos.: WO 2010/048304, WO 2005/0233392, and WO2008/056854, which are incorporated herein in their entirety by reference. One of the skill in the art can easily perform the measurement of mRNA or protein level of these biomarkers in a biological sample e.g. blood from a subject such as human, using the standard methods in the art. In some implementations, a subject identified with HCC is administered a LSF inhibitor according to the methods as disclosed herein.

As disclosed herein, a subject with HCC can also be selected by detecting a high level of LSF expression in a biological sample such as a liver sample from the subject as compared to a reference level. In one Implementation, the reference level is the level of LSF in a normal healthy subject.

In addition, a biopsy can be used to diagnose HCC. (Walter et al., 24 Curr Opin Gastroenterol. 312 (2008)). Other diagnostic methods for HCC known to one of the skill in the art include imaging methods such as ultrasound, computed tomography (CT) scan and MRI (Scholmerich et al., 52 Gut. 1224 (2004)). In various implementations, a pharmaceutical composition comprising compounds of Formula (I) as disclosed herein can be administered to a subject diagnosed with HCC or HCC susceptibility.

In some implementations, a subject undergoing treatment of HCC, e.g. chemotherapy, can be treated alone or in combination with the methods and compositions as disclosed herein. For example, the inventors have previously reported in collaboration with other scientists that inhibition of LSF can increase sensitivity of HCC cells to chemotherapeutic agents, such as, but not limited to 5-fluorouracil (5-FU) (see Yoo et al., PNAS, 2010; 107; 8357-8362). Accordingly, in some implementations, subjects with no response to current HCC therapeutic treatment, e.g. HCC subjects who have shown chemoresistance to chemotherapeutic agents such as 5-FU, can be administered with a LSF small molecule inhibitor as disclosed herein using the methods and compositions of the described herein, prior to or concurrently with chemotherapy.

Detection of hepatocellular carcinoma can be difficult as most of the patients who develop this tumor have no symptoms other than those inflicted with their longstanding liver disease. The onset of abdominal pain, weight loss, early satiety, jaundice and a palpable mass in the upper abdomen usually indicate an advanced cancer. Accordingly, in some implementations, subjects at high risk for HCC can be administered an inhibitor of LSF as disclosed herein in the methods and compositions for prevention of the development of HCC (e.g. prophylactic treatment). For example, subjects highly susceptible to HCC are subjects with HBV, HCV, chronic alcohol consumption, an exposure to aflatoxin B1 in food (which is a liver carcinogenic chemical produced by a mold called *Aspergillus flavus* after food has been stored in a hot and humid environment), hepatic adenoma resulted from the use of female hormones (estrogens) and protein-building (anabolic) steroids, an exposure to thorotrast (a previously used contrast agent for imaging, which caused a cancer of the blood vessels in the liver called hepatic angiosarcoma), hepatic angiosarcomas (resulted from a prolonged exposure to vinyl chloride, a compound used in the plastics industry), hereditary hemochromatosis (a disorder that causes the body to accumulate excessive amounts of iron), emphysema and cirrhosis (resulted from alpha 1 anti-trypsin deficiency) and hereditary tyrosinemia.

In additional implementations, for prophylactic treatment (e.g. to prevent reoccurrence of HCC), subjects who was diagnosed with HCC before and HCC is in remission can be selected for treatment with a LSF inhibitor as disclosed herein using the methods and compositions described herein. For example, subjects who had their HCC tumor removed by hepatectomy and/or liver transplantation, or who had their HCC tumor reduced or stabilized by other therapeutic methods are amenable to administration of a LSF inhibitor or a pharmaceutical composition thereof as disclosed herein.

In yet other implementations, subjects amenable to therapeutic treatment with methods and compositions described herein, e.g. using a LSF inhibitor as disclosed herein, include subjects in need of inhibition of LSF. For example, it has been reported that HIV patients, or individuals in need for a decrease in inflammatory response or immune function can be treated by inhibiting LSF (Bovolenta et al, 163 J. Immuno. 6892, (1999), U.S. Patent Application No.: US2009/0081183 and International Application No.: WO1998/36641, which are incorporated herein in their entirety by reference). Accordingly, a LSF inhibitor according to some implementations as disclosed herein can be administered alone, or concurrently with other LSF inhibitors such as IL2, or peptides, antibodies or antisense RNA against LSF, to subjects in which inhibition of LSF is desirable, such as HIV.

In still another implementation, a subject who has other cancers such as breast cancer but has an up-regulated expression of LSF as compared to a reference level can be selected for therapeutic treatment with methods and compositions using a LSF inhibitor as disclosed herein. In some implementations, a reference level is the expression of LSF in a normal healthy subject. In other implementations, a reference level is the expression of LSF in the same subject measured at the previous time point of the treatment regime. Other cancer indications that can be used according to some implementations include brain cancer, colon cancer, head and neck squamous cell carcinoma, lung cancer, pancreatic cancer, cervical cancer, ovarian cancer, and thyroid cancer.

Another aspect according to some implementations relates to pharmaceutical compositions for treatment of diseases or disorders where it is therapeutically beneficial to inhibit LSF, e.g. hepatocellular carcinoma. In some implementations, a pharmaceutical composition comprises a therapeutically effective amount of at least one LSF inhibitor selected from any of the compounds represented by Formula (I) disclosed herein. In one implementation, the LSF inhibitor is a compound of Formula (I). In some implementations, the LSF inhibitor is a compound selected from the group consisting of compounds of Formula (I). In some implementations, the LSF inhibitor is selected from the group consisting of compounds of Formula (II). In some implementations, the LSF inhibitor is selected from the group consisting of compounds of Formula (IIA). In some implementations, the LSF inhibitor is the compound (FQI-37Q). In some implementations, the LSF inhibitor is compound (FQI-34Q). In some implementations, the LSF inhibitor is compound (FQI-1Q).

A LSF inhibitor as disclosed herein selected from compounds of Formula (I) can be used in an amount of about 0.001 to 10 mg/kg of body weight or about 0.005 to 8 mg/kg of body weight or about 0.01 to 6 mg/kg of body weight or about 0.1 to 0.2 mg/kg of body weight or about 1 to 2 mg/kg of body weight. In some implementations, an inhibitor of LSF can be used in an amount of about 0.1 to 1000 µg/kg of body weight or about 1 to 100 µg/kg of body weight or about 10 to 50 µg/kg of body weight. In some implementations, a LSF inhibitor as disclosed herein selected from Formula (I) can be used at a concentration of about 0.001 mg/ml or 0.1 mg/ml or a higher concentration of 0.1 mg/ml. In some implementations, a pharmaceutical composition comprises at least one LSF inhibitor at a concentration of about 0.01 µM to 300 µM, or about 0.1 µM to 150 µM, or about 1 µM to 50 µM, or about 1 µM to 25 µM. The dosage may vary within this range depending upon the dosage form employed and the route of administration utilized. In some implementations, a pharmaceutical composition does not comprise LSF inhibitors of Formula (V). In some implementations, a pharmaceutical composition does not comprise LSF inhibitors described in U.S. application Ser. No. 15/713,956, U.S. Pat. Nos. 9,802,948, 9,815,845, 9,597,325 and WO 2012/050985 which are incorporated herein in their entirety by reference.

Depending on routes of administration, one of skill in the art can determine and adjust an effective dosage of a LSF inhibitor disclosed herein to a subject such as a human subject accordingly, by determining pharmacokinetics and bioavailability of a LSF inhibitor and analyzing dose-response relationship specific to a LSF inhibitor in animal models such as a mouse.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. In some implementations, compositions that exhibit large therapeutic indices, are used.

The data obtained from the cell culture assays and animal studies can be used in formulating a range of dosage for use in humans. The therapeutically effective dose can be determined by one of ordinary skill in the art, e.g. using cell culture assays. An effective dose of a LSF inhibitor can be determined in an animal model by measuring the tumor weight and tumor volume over the course of treatment with a LSF inhibitor as compared to no treatment. In some implementations, a dosage comprising a LSF inhibitor is considered to be effective if the dosage inhibits or decreases the growth of tumor weight and/or tumor volume by at least about 15%, at least about 20%, at least about 30%, at least about 40%, at least about 50%, at least about 60%, at least about 70%, at least about 80%, at least about 90%, 95%, 99% or even 100%, as compared to a control (e.g. in the absence of a LSF inhibitor). In some implementations, a therapeutically effective amount of a LSF inhibitor administered to a subject is dependent upon factors known to a person of ordinary skill, including bioactivity and bioavailability of a LSF inhibitor (e.g. half-life and stability of a LSF inhibitor in the body), chemical properties of a LSF inhibitor (e.g. molecular weight, hydrophobicity and solubility); route and frequency of administration, time of administration (e.g. before or after a meal), and the like. Further, it will be understood that the specific dose of the pharmaceutical composition comprising a LSF inhibitor as disclosed herein to provide the therapeutic or prophylactic benefits can depend on a variety of factors including physical condition of the subject (e.g. age, gender, weight), medical history of the subject (e.g. medications being taken, other diseases or disorders) and clinical condition of the subject (e.g. health condition, stage of the disease). The precise dose of a pharmaceutical composition comprising a LSF inhibitor can be determined by methods known to a skilled artisan such as pharmacologists and physicians.

According to some implementations, an LSF inhibitor as disclosed herein selected from compounds of Formula (I) can be administered prophylactically or therapeutically to a subject prior to, simultaneously or sequentially with other therapeutic regimens or agents (e. g. multiple drug regimens), in a therapeutically effective amount. In some implementations, a LSF inhibitor administered concurrently with other therapeutic agents can be administered in the same or different compositions.

In some implementations, a pharmaceutical composition comprising at least one LSF inhibitor further comprises a second therapeutic agent. In one implementation, the second therapeutic agent is a chemotherapeutic agent such as Sorafenib or 5-FU. In some implementations, the second therapeutic agent is a second LSF inhibitor, e.g. a compound selected from any of formula (I). In other implementations, the second therapeutic agent is a therapeutic for liver diseases such as HBV, HCV and cirrhosis.

In prophylactic applications, pharmaceutical compositions (or medicaments) comprising a LSF inhibitor can be administered to a subject susceptible to, or otherwise at risk of, a disease or disorder mediated by elevated levels of LSF in an amount sufficient to eliminate or reduce the risk or delay the onset of the disease. In one implementation, the disease or disorder to be prevented is hepatocellular carcinoma (HCC). As most HCCs are generated from the background of hepatitis B virus (HBV) or hepatitis C virus (HCV), a subject with HBV or HCV can be subjected to an effective amount or dose of a pharmaceutical composition comprising a LSF inhibitor described herein. In one implementation, a pharmaceutical composition disclosed herein comprises a compound of Formula (I), or enantiomers, prodrugs, derivatives or pharmaceutically acceptable salts thereof. In some implementations, an effective amount or dose of a pharmaceutical composition comprising a LSF inhibitor disclosed herein can be administered to a subject at high risk of HCC. In additional implementations, a pharmaceutical composition further comprises a second therapeutic agent, e.g. therapeutics to treat high-risk factors such as liver diseases (e.g. HBV). Representative high-risk factors of HCC include hepatic cirrhosis, chronic alcohol consumption, (prolonged) exposure to liver carcinogenic chemicals such as aflatoxin B1 in food, thorotrast in diagnostic contrast agent and vinyl chloride, hepatic adenoma, hepatic angiosarcoma, hepatic angiosarcomas, hereditary hemochromatosis, emphysema and cirrhosis resulted from alpha 1 anti-trypsin deficiency, and hereditary tyrosinemia. In various implementations, individuals that have discontinued treatment for high-risk factors of HCC can still be subjected to a pharmaceutical composition comprising an effective dose of compound selected from any compound of Formula (I) as disclosed herein for prevention of development of HCC. For such implementations, an effective dose of a LSF inhibitor can be higher or lower than the previous dosage.

In therapeutic applications, according to some implementations provided herein, when an effective amount or effective dose of a pharmaceutical composition comprising a LSF inhibitor selected from Formula (I) is administered to the subject with cancer, e.g. hepatocellular carcinoma, progression of cancer, e.g. HCC, can be delayed or inhibited. In some implementations, administration of an effective amount or effective dose of a pharmaceutical composition comprising a LSF inhibitor selected from any compound of Formula (I) to a subject with hepatocellular carcinoma can inhibit or delay progression of HCC. In further implementations, treating subjects with an effective dose of a pharmaceutical composition comprising a LSF inhibitor can prevent or delay metastasis of HCC in the subject. In some implementations, a LSF inhibitor used for therapeutic treatment of various diseases, e.g. HCC, using the methods and compositions disclosed herein is the compound FQI-37. In some implementations, a LSF inhibitor used for therapeutic treatment of various diseases, e.g. HCC, using the methods and compositions disclosed herein is the compound FQI-34Q, FQI-37Q, or prodrugs, derivatives or pharmaceutically acceptable salts thereof.

In therapeutic applications, a relatively high dosage in relatively short intervals is sometimes required until progression of the disease is reduced or terminated, or until the subject shows partial or complete amelioration of symptoms of disease. Thereafter, the subject can be administered a prophylactic regime. For example, subjects with HCC can be treated with a LSF inhibitor as disclosed herein at an effective dose in a therapeutic regimen accordingly to prevent or delay the progression of HCC or metastasis. In other implementations, a LSF inhibitor can be administered using the methods and compositions as disclosed herein to chemotherapy subjects in order to increase sensitivity to chemotherapy. In some implementations, an inhibitor of LSF as disclosed herein can be administered to subjects prior to, concurrently with, or sequentially to treatment with chemotherapeutic drugs, e.g. Sorafenib. In further implementations, HCC subjects selected for other therapeutic procedures or surgeries, such as hepatectomy, intralesional ethanol injection, or chemoembolization, can be subjected to a treatment with a LSF inhibitor as disclosed herein. For example, a pharmaceutical composition according to some implementations can be administered prior to, during or after therapeutic procedures. Route of administration can vary with therapeutic procedures or surgeries and can be determined by a skilled artisan. In yet another implementation, compositions and methods can be used as an adjuvant therapy.

In some implementations, the subject is a human, and in alternative implementations the subject is a non-human mammal. Treatment dosages need to be titrated to optimize safety and efficacy. The amount of a LSF inhibitor depends on the stage of the disease, e.g. HCC as well as whether a second therapeutic agent is also administered. The second therapeutic agent can be an agent to treat a different disease or disorder. In some implementations, the second therapeutic agent can be a chemotherapeutic agent such as Doxorubicin, 5-FU, Paclitaxel, Irinotecan, Patupilone, Everolimus, multikinase inhibitors (Sorafenib and Sunitinib), and EGFR inhibitors (Cetuximab, Erlotinib, Gefitinib, Brivanib, Lapatinib). In alternative implementations, the second therapeutic agent can be a second LSF inhibitor. In some implementations, a second LSF inhibitor can be selected from the group consisting of compounds of Formula (I), and enantiomers, prodrugs and pharmaceutically acceptable salts thereof. In one implementation, a second LSF inhibitor can be an enantiomer of a first LSF inhibitor. In further implementations, a second therapeutic agent is another therapeutics to target another disease, or another disorder, or a different symptom. In combination with other therapeutics, the dosage of a LSF inhibitor can be reduced, compared to the standard dosage of a LSF inhibitor when administered alone.

In some implementations, the frequency of administration can vary significantly from once a day, once every other day, once every 3 days, once weekly, once monthly to once a year, depending on the disease of cancer (e.g., stage of cancer) such as HCC stage, and/or mode of administration.

Generally, effective dosages and dosing schedules can be adjusted based on, for example, the outcome of the treatment such as whether the progression rate of HCC is slower or terminated, or whether at least one of the symptoms associated with HCC is reduced. In accordance with the teachings provided herein, the effectiveness of the treatment can be monitored by obtaining a biological sample from a subject, e.g. a blood serum sample, and determining the level of biomarkers for HCC, such as AFP in the serum sample, using methods well known in the art and the diagnostic methods. The efficacy of the treatment can also be monitored by imaging modalities such as CT scan, MRI, ultrasound, and the like that are known to a skilled artisan.

In some implementations, the daily dose administered to a subject in a form of a bolus composition comprising a LSF inhibitor can be given in a single dose, in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease. It is also within the skill of the art to start doses at levels lower than required to achieve the desired therapeutic effect and to gradually increase the dosage until the desired effect is achieved.

In various implementations, a LSF inhibitor selected from any compound of Formula (I) can be a pro-drug, where it is activated by a second agent. Accordingly, in such implementations, administration of such the second agent which activates the pro-drug into its active form can be administered the same time, concurrent with, or prior to, or after the administration of the pharmaceutical composition comprising a LSF inhibitor as disclosed herein.

In some implementations, a LSF inhibitor selected from any compound of Formula (I) as disclosed herein is often administered as pharmaceutical compositions comprising an active therapeutic agent, i.e. a LSF inhibitor, and a variety of other pharmaceutically acceptable components. See Remington's Pharmaceutical Science (15th ed., Mack Publishing Company, Easton, Pa., 1980). The formulation of the compositions depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, non-therapeutic, non-immunogenic stabilizers and the like. However, some reagents suitable for administration to animals may not necessarily be used in compositions for human use.

Some embodiments of the various aspects described herein can be described as in the following numbered paragraphs:

1. A compound of Formula (I) or enantiomers, prodrugs, derivatives, and pharmaceutically acceptable salts thereof.
2. The compound according to paragraph 1, wherein $R^1$ is hydrogen, halogen, $OR^{1A}$, $NR^{1A}R^{2A}$, $SR^{1A}$, $C_1$-$C_6$alkyl or $-NO_2$.
3. The compound according to any one of paragraphs 1-2, wherein $R^1$ is hydrogen, halogen, $OR^{1A}$ or $NR^{1A}R^{2A}$.
4. The compound according to any one of paragraphs 1-3, wherein $R^1$ is hydrogen or $OR^{1A}$.
5. The compound according to paragraph 4, wherein $R^{1A}$ is H, alkyl, alkenyl, alkynyl, cycloalkyl, heterocyclyl, aryl or heteroaryl.
6. The compound according to paragraph 5, wherein $R^{1A}$ is H or alkyl.
7. The compound according to any one of paragraphs 1-6, wherein $R^1$ is OH or $O(C_1$-$C_6$ alkyl).
8. The compound according to any one of paragraphs 1-7, wherein $R^1$ is OH, methoxy, ethoxy, propoxy or isopropoxy.
9. The compound according to any one paragraphs 1-8, wherein $R^1$ is ethoxy.
10. The compound according to any one of paragraphs 1-9, wherein $R^2$ is hydrogen, halogen, $OR^{1A}$, $NR^{1A}R^{2A}$, $SR^{1A}$, $C_1$-$C_6$alkyl or $-NO_2$.
11. The compound according to any one of paragraphs 1-10, wherein $R^2$ is hydrogen, halogen, $C_1$-$C_6$alkyl, $OR^{1A}$ or $NR^{1A}R^{2A}$.
12. The compound according to any one of paragraphs 1-11, wherein $R^2$ is hydrogen, halogen or $OR^{1A}$.
13. The compound according to any one of paragraphs 1-12, wherein $R^2$ is hydrogen.
14. The compound according to any one of paragraphs 1-13, wherein $R^3$ is hydrogen, halogen, $OR^{1A}$, $NR^{1A}R^{2A}$, $SR^{1A}$, $C_1$-$C_6$alkyl or $-NO_2$.
15. The compound according to any one of paragraphs 1-14, wherein $R^3$ is halogen, $OR^{1A}$, $NR^{1A}R^{2A}$, $C_1$-$C_6$alkyl or $-NO_2$.
16. The compound according to any one of paragraphs 1-15, wherein $R^3$ is halogen, $NR^{1A}R^{2A}$, $C_1$-$C_6$alkyl or $-NO_2$.
17. The compound according to any one of paragraphs 1-16, wherein $R^3$ is halogen, $NR^{1A}R^{2A}$.
18. The compound according to any one of paragraphs 1-17, wherein $R^{1A}$ and $R^{2A}$ independently are H, alkyl, alkenyl, cycloalkyl, heterocyclyl, aryl or heteroaryl.
19. The compound according to any one of paragraphs 1-18, wherein $R^{1A}$ and $R^{2A}$ independently are H or $C_1$-$C_6$alkyl.

20. The compound according to any one of paragraphs 1-19, wherein $R^{1A}$ and $R^{2A}$ independently are H, methyl, ethyl, propyl, isopropyl, butyl, isobutyl, t-butyl or pentyl.
21. The compound according to any one paragraphs 1-20, wherein $R^{1A}$ and $R^{2A}$ independently are methyl, ethyl, propyl or isopropyl.
22. The compound according to any one paragraphs 1-21, wherein $R^{1A}$ and $R^{2A}$ are methyl.
23. The compound according to any one of paragraphs 1-22, wherein $R^4$ is hydrogen, halogen, $OR^{1A}$, $NR^{1A}R^{2A}$, $SR^{1A}$, $C_1$-$C_6$alkyl or —$NO_2$.
24. The compound according to any one of paragraphs 1-23, wherein $R^4$ is hydrogen, halogen, $C_1$-$C_6$alkyl, $OR^{1A}$ or $NR^{1A}R^{2A}$.
25. The compound according to any one of paragraphs 1-24, wherein $R^4$ is hydrogen, halogen or $OR^{1A}$.
26. The compound according to any one of paragraphs 1-25, wherein $R^4$ is hydrogen.
27. The compound according to any one of paragraphs 1-26, wherein $R^5$ is hydrogen, halogen, $OR^{1A}$, $NR^{1A}R^{2A}$, $SR^{1A}$, $C_1$-$C_6$alkyl or —$NO_2$.
28. The compound according to any one of paragraphs 1-27, wherein $R^5$ is hydrogen, halogen, $C_1$-$C_6$alkyl, $OR^{1A}$ or $NR^{1A}R^{2A}$.
29. The compound according to any one of paragraphs 1-28, wherein $R^5$ is hydrogen, halogen or $OR^{1A}$.
30. The compound according to any one of paragraphs 1-29, wherein $R^5$ is hydrogen.
31. The compound according to any one of paragraphs 1-30, wherein $R^6$ is hydrogen, halogen, $OR^{1A}$, $NR^{1A}R^{2A}$, or $C_1$-$C_6$ alkyl.
32. The compound according to any one of paragraphs 1-31, wherein $R^6$ is hydrogen, halogen, $OR^{1A}$, $SR^{1A}$, or $C_1$-$C_6$ alkyl.
33. The compound according to any one of paragraphs 1-32, wherein $R^6$ is hydrogen, halogen, or $OR^{1A}$.
34. The compound according to any one of paragraphs 1-33, wherein $R^6$ is H.
35. The compound according to any one of paragraphs 1-34, wherein $R^7$ is hydrogen, halogen, $OR^{1A}$, $NR^{1A}R^{2A}$, $SR^{1A}$, or $C_1$-$C_6$ alkyl.
36. The compound according to any one of paragraphs 1-35, wherein $R^7$ is hydrogen, halogen, $OR^{1A}$, $SR^{1A}$, or $C_1$-$C_6$ alkyl.
37. The compound according to any one of paragraphs 1-36, wherein $R^7$ is hydrogen, halogen, or $OR^{1A}$.
38. The compound according to any one of paragraphs 1-37, wherein $R^7$ is H or $OR^{1A}$.
39. The compound according to any one of paragraphs 1-30, wherein $R^6$ and $R^7$ together with the carbons to which they are attached to form an optionally substituted 5-8 membered cycloalkyl or heterocycle ring.
40. The compound according to paragraph 39, wherein $R^6$ and $R^7$ together with the carbons to which they are attached to form an optionally substituted 5-8 membered cycloalkyl or heterocycle ring.
41. The compound according to paragraph 40, wherein $R^6$ and $R^7$ together with the carbons to which they are attached to form an optionally substituted dioxolane.
42. The compound according to paragraph 40, wherein $R^6$ and $R^7$ together with the carbons to which they are attached to form an optionally substituted dioxane.
43. The compound according to any one of paragraphs 1-42, wherein $R^8$ is hydrogen, halogen, $OR^{1A}$, $NR^{1A}R^{2A}$, or $C_1$-$C_6$ alkyl.
44. The compound according to any one of paragraphs 1-43, wherein $R^8$ is hydrogen, halogen, $OR^{1A}$, $SR^{1A}$, or $C_1$-$C_6$ alkyl.
45. The compound according to any one of paragraphs 1-44, wherein $R^8$ is hydrogen, halogen, or $OR^{1A}$.
46. The compound according to any one of paragraphs 1-45, wherein $R^8$ is H or $OR^{1A}$.
47. The compound according to any one of paragraphs 1-34, wherein $R^7$ and $R^8$ together with the carbons to which they are attached to form an optionally substituted 5-8 membered cycloalkyl or heterocycle ring.
48. The compound according to paragraph 47, wherein $R^7$ and $R^8$ together with the carbons to which they are attached to form an optionally substituted 5-8 membered cycloalkyl or heterocycle ring.
49. The compound according to paragraph 48, wherein $R^7$ and $R^8$ together with the carbons to which they are attached to form an optionally substituted dioxolane.
50. The compound according to paragraph 48, wherein $R^7$ and $R^8$ together with the carbons to which they are attached to form an optionally substituted dioxane.
51. The compound according to any one of paragraphs 1-50, wherein $R^9$ is hydrogen, halogen, $OR^{1A}$, $NR^{1A}R^{2A}$, or $C_1$-$C_6$ alkyl.
52. The compound according to any one of paragraphs 1-51, wherein $R^9$ is hydrogen, halogen, $OR^{1A}$, $SR^{1A}$, or $C_1$-$C_6$ alkyl.
53. The compound according to any one of paragraphs 1-52, wherein $R^9$ is hydrogen, halogen, or $OR^{1A}$.
54. The compound according to any one of paragraphs 1-53, wherein $R^9$ is H or $OR^{1A}$.
55. The compound according to any one of paragraphs 1-38, wherein $R^8$ and $R^9$ together with the carbons to which they are attached to form an optionally substituted 5-8 membered cycloalkyl or heterocycle ring.
56. The compound according to paragraph 55, wherein $R^8$ and $R^9$ together with the carbons to which they are attached to form an optionally substituted 5-8 membered cycloalkyl or heterocycle ring.
57. The compound according to paragraph 56, wherein $R^8$ and $R^9$ together with the carbons to which they are attached to form an optionally substituted dioxolane.
58. The compound according to paragraph 56, wherein $R^7$ and $R^8$ together with the carbons to which they are attached to form an optionally substituted dioxane.
59. The compound according to any one of paragraphs 1-58, wherein $R^{10}$ is hydrogen or $C_1$-$C_6$ alkyl.
60. The compound according to any one of paragraphs, 1-59, wherein $R^{10}$ is hydrogen, methyl, ethyl, propyl, isopropyl, butyl, isobutyl, t-butyl or pentyl.
61. The compound according to any one of paragraphs 1-60, wherein $R^{10}$ is hydrogen.
62. The compound according to any one of paragraphs 1-61, wherein $R^{11}$ is hydrogen, halogen, $OR^{1A}$ or $C_1$-$C_6$alkyl.
63. The compound according to any one of paragraphs 1-62, wherein $R^{11}$ is hydrogen or $C_1$-$C_6$alkyl.
64. The compound according to any one of paragraph 1-63, wherein $R^{11}$ is hydrogen.
65. The compound according to any one of paragraphs 1-58, wherein $R^{10}$ and $R^{11}$ together form a double bond between the carbon atoms they are attached to.
66. The compound according to any one of paragraphs 1-65, wherein $R^{12}$ is hydrogen, halogen, $OR^{1A}$ or $C_1$-$C_6$alkyl.
67. The compound according to any one of paragraphs 1-66, wherein $R^{12}$ is hydrogen or $C_1$-$C_6$alkyl.

68. The compound according to any one of paragraph 1-67, wherein $R^{12}$ is hydrogen.
69. The compound according to any one of paragraphs 1-58 or 62-64, wherein $R^{10}$ and $R^{12}$ together form a double bond between the carbon atoms they are attached to.
70. The compound according to any one of paragraphs 1-58, wherein $R^{11}$ and $R^{12}$ together form a carbonyl.
71. The compound according to any one of paragraphs 1-70, wherein $R^{13}$ is hydrogen, halogen, $OR^{14}$ or $C_1$-$C_6$alkyl.
72. The compound according to any one of paragraphs 1-71, wherein $R^{13}$ is hydrogen or $C_1$-$C_6$alkyl.
73. The compound according to any one of paragraph 1-72, wherein $R^{13}$ is hydrogen.
74. The compound according to any one of paragraphs 1-64, wherein $R^{12}$ and $R^{13}$ together form a double bond between the carbon atoms they are attached to.
75. The compound according to any one of paragraphs 1-74, wherein $R^{14}$ is hydrogen, halogen, $OR^{14}$ or $C_1$-$C_6$alkyl.
76. The compound according to any one of paragraphs 1-75, wherein $R^{14}$ is hydrogen or $C_1$-$C_6$alkyl.
77. The compound according to any one of paragraph 1-76, wherein $R^{14}$ is hydrogen.
78. The compound according to any one of paragraphs 1-64 or 71-73, wherein $R^{12}$ and $R^{14}$ together form a double bond between the carbon atoms they are attached to.
79. The compound according to any one of paragraphs 1-70, wherein $R^{13}$ and $R^{14}$ together form a carbonyl (=O).
80. The compound according to paragraph 1, wherein the compound is FQI-34Q, FGI-37Q, FQI-1Q, JAK-196-22 or JAK 196.23.
81. The compound according to paragraph 80, wherein the compound is FQI-34Q, FGI-37Q or FQI-1Q,
82. A pharmaceutical composition comprising a compound of any one of paragraphs 1 to 81 and a pharmaceutically acceptable excipient or carrier.
83. A method for inhibiting LSF in a subject, the method comprising administering an effective amount of a compound of any one of paragraphs 1 to 81 or the pharmaceutical composition of paragraph 82 to a subject in need thereof.
84. The method of paragraph 83, wherein the subject suffers from or is at risk of cancer.
85. A method for treating cancer in a subject, the method comprising administering an effective amount of a compound of any one of paragraphs 1 to 81 or the pharmaceutical composition of paragraph 82 to a subject in need thereof.
86. The method of paragraph 84 or 85, wherein the cancer is selected from the group consisting of breast cancer, colon cancer, ovarian cancer, pancreatic cancer, lung cancer, kidney cancer, cancers of the hematopoietic system, cancers of the endometrium, cervical cancer, cancers of the upper digestive tract, stomach cancer, liver cancers and cancers of the small intestine.
87. The method of any one paragraphs 84-86, wherein the cancer is hepatocellular carcinoma (HCC).
88. The method of any one paragraphs 83-87, further comprising administering an additional anti-cancer therapy to the subject.
89. The method of any one paragraphs 83-88, wherein the subject suffers from or is at risk of HIV or is in need of lower inflammatory responses.
90. The method of any one paragraphs 83-89, wherein the administering is topical, enteral, or parenteral.
91. The method of any one paragraphs 83-90, wherein administering is oral, intravenous injection or subcutaneous injection.
92. The method of any one paragraphs 83-91, wherein the subject is human.
93. A method of inhibiting growth or proliferation of a cell, the method comprising contacting the cell with a compound of any one of paragraphs 1-81 to a cell expressing LSF.
94. The method of paragraph 93, wherein an in-vitro growth inhibition (GI50) for the cell is less than 5 µM, or less than about 0.5 µM, or less than 0.3 µM.
95. A method of inhibiting tubulin methylation in a cell, the method comprising administering to the cell an effective amount of a compound of any one of paragraphs 1-81.
96. A method of modulating chromatin or cytoskeleton modification in a cell, the method comprising administering to the cell an effective amount of a compound of any one of paragraphs 1-81.
97. The method of any one of paragraphs 93-96, wherein the cell is a mammalian cell.
98. The method of any one of paragraphs 93-97, wherein the cell is a human cell.
99. The method of any one of paragraphs 93-98, wherein said administering to the cell is in vivo.
100. The method of any one of paragraphs 93-98, wherein said administering to the cell is in vitro.
101. A method of preparing a compound having Formula (II), the method comprising:
    providing a first compound and a second compound in a first solution, and reacting the first compound with the second compound, wherein the first compound has the Formula (IX) and the second compound has the Formula (X).
102. The method of paragraph 101, wherein the first compound and second compound react to form and intermediate compound, at least a portion of the first solution is removed, the intermediate compound is combined with a second solution, and the intermediate compound undergoes an intermolecular cyclization reaction to provide compound of Formula (II), wherein the intermediate compound has the structure of Formula (XI).
103. The method of paragraph 101 or 102, wherein $R^{10}$ is hydrogen and providing the first compound comprises:
    providing a nitro-aromatic compound and an aromatic amine in coupling solution, and reacting the nitro aromatic compound with the aromatic amine to provide a coupled nitro-aromatic compound;
    removing at least a portion of the coupling solution and adding a reducing solution;
    and reducing the nitro-aromatic compound, providing the first compound (IX) having $R^{10}$ is hydrogen,
    wherein the nitro-aromatic compound has the structure of Formula (XII), the aromatic amine has the structure of Formula (XIII), and the coupled nitro-aromatic compound has the structure of Formula (XIV).

Definitions

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular implementations, and are not intended to limit the claimed invention, because the scope of the invention is limited only by the claims. Unless otherwise defined, all technical and scientific terms used herein have the same meaning as commonly understood by one of ordinary skill in the art to which this invention belongs.

Structures

As used herein the term "geminal" refers to a pair of atoms or pair of groups bonded to the same carbon. For example, in compound (I), $R^{11}$ and $R^{12}$ are a geminal pair, and $R^{13}$ and $R^{14}$ are a geminal pair.

As used herein the term "vicinal" refers to a pair of atoms or groups bonded to adjacent carbons. For example, in compound (I), $R^{11}$ and $R^{12}$ are vicinal to $R^{13}$ and $R^{14}$, i.e. the $R^{11}$ and $R^{13}$ are a vicinal pair, $R^{12}$ and $R^{14}$ are a vicinal pair, $R^{11}$ and $R^{13}$ are a vicinal pair, and $R^{12}$ and $R^{14}$ are a vicinal pair.

The structure definitions such as "alkyl" are provided below for nomenclature purposes. They do not exclude the meaning as those acquired in the art to which this invention pertains. The term "alkyl" as used herein refers to a linear, branched, or cyclic saturated hydrocarbon group typically although not necessarily containing 1 to about 24 carbon atoms, for example 1 to about 12, 1 to about 6 carbon atoms or a lower alkyl, such as methyl, ethyl, n-propyl, isopropyl, n-butyl, isobutyl, sec-butyl, tert-butyl, pentyl, hexyl, and the like, as well as cycloalkyl groups such as cyclopropyl, cyclobutryl, cyclopentyl, cyclohexyl, cycloheptyl, cyclooctyl and the like. The term "cycloalkyl" intends a cyclic alkyl group, for example having 3 to 10, 5 to 8, or 3 to 8, carbon atoms. The term "substituted alkyl" refers to alkyl substituted with one or more substituent groups, and the terms "heteroalkyl" and "heteroatom-containing alkyl" refer to alkyl in which at least one carbon atom is replaced with a heteroatom. The term "heterocycle" and "heterocycle ring" intends a cyclic heteroalkyl, for example having 3 to 10, 5 to 8, or 3 to 8, carbon atoms. The term "haloalkyl" as used herein refers to an alkyl structure with at least one substituent of a halide such as fluorine, chorine, bromine or iodine, or with combinations thereof. If not otherwise indicated, the term "alkyl" includes linear, branched, cyclic, unsubstituted, substituted, and/or heteroatom-containing alkyl, respectively.

The term "alkenyl" as used herein refers to a linear, branched, or cyclic hydrocarbon group of 2 to about 16 carbon atoms containing at least one double bond, such as ethenyl, n-propenyl, isopropenyl, n-butenyl, isobutenyl, n-pentenyl, iso-pentenyl, hexenyl, heptenyl, octenyl, decenyl, tetradecenyl, hexadecenyl, eicosenyl, tetracosenyl, and the like. For example, alkenyl groups herein can contain 2 to about 12 carbon atoms, 2 to about 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the term "alkenyl" includes linear, branched, cyclic, unsubstituted, substituted, and/or heteroatom-containing alkenyl, respectively.

The term "alkynyl" as used herein refers to a linear or branched-chain hydrocarbon group having one or more carbon-carbon triple-bonds and having from 2 to about 16 carbon atoms, 2 to 12 carbon atoms, or 2 to 8 carbon atoms. Examples of alkynyl groups include ethynyl, propynyl, butynyl, pentynyl and the like.

The term "alkoxy" as used herein intends an alkyl group bound through a single, terminal ether linkage; that is, an "alkoxy" group may be represented as —O-alkyl where alkyl is as defined herein. Exemplary alkoxy groups include, but are not limited to O-methyl, O-ethyl, O-n-propyl, O-isopropyl, O-n-butyl, O-isobutyl, O-sec-butyl, O-tert-butyl, O-pentyl, O-hexyl, O-cyclopropyl, O-cyclobutyl, O-cyclopentyl, O-cyclohexyl and the like.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). In some implementations, aryl groups contain 5 to 24 carbon atoms. In some implementations, aryl groups contain 5 to 14 carbon atoms. Exemplary aryl groups contain one aromatic ring or two fused or linked aromatic rings, e.g., phenyl, 1-naphthyl, 2-naphthyl, biphenyl, pyridine, quinoline, furan, thiophene, pyrrole, imidazole, pyrazole, diphenylether, diphenylamine, benzophenone, and the like. "Substituted aryl" refers to an aryl moiety substituted with one or more, (e.g., one, two, three, four or more) substituent groups, and the terms "heteroatom-containing aryl" and "heteroaryl" refer to aryl substituents in which at least one carbon atom is replaced with a heteroatom such as oxygen, nitrogen and sulfur. The term "heteroaryl" includes ring systems such as pyridine, quinoline, furan, thiophene, pyrrole, imidazole and pyrazole and the like.

The term "heterocycyl" as used herein refers to a single ring or multiple rings that are fused together, directly linked, or indirectly inked (such that the different rings are bound to a common group such as a methylene or ethylene moiety), in which at least one carbon atom is replaced with a heteroatom such as oxygen, nitrogen and sulfur. In some implementations, heterocycyl groups contain 3 to 24 carbon atoms, 3 to 14 carbon atoms, or 3 to 6 carbon atoms. For example, a heterocycyl group can be a five-membered ring with at least one carbon replaced by oxygen or nitrogen.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic. In one implementation, the bicyclic or polycyclic ring may be fused ring. The fusion of the ring may be across a bond between two atoms, i.e. two cyclic rings share one bond or two atoms, for example, a decalin; the fusion of the ring may be across a sequence of atoms, i.e. two cyclic rings share three or more atoms, for example a norbornane.

By "substituted" as in "substituted alkyl," "substituted aryl," and the like, as alluded to in some of the definitions as described herein, is meant that in the alkyl, aryl, or other moiety, at least one hydrogen atom bound to a carbon (or other) atom is replaced with one or more non-hydrogen substituents. Examples of such substituents include, without limitation: halogen, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aryl alkoxy, $C_6$-$C_{24}$ alkyl aryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—(CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO⁻), carbamoyl (—(CO)—NH₂), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)₂), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)₂), di-N—($C_1$-$C_{24}$ alkyl), N—($C_5$-$C_{24}$ aryl)-substituted carbamoyl, thiocarbamoyl (—(CS)—NH₂), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)₂), mono-($C_5$-$C_{24}$ aryl)-substituted thiocarbamoyl (—(CO)—NH-aryl), di-($C_5$-$C_{24}$ aryl)-substituted thiocarbamoyl (—(CO)—N($C_5$-$C_{24}$ aryl)₂), di-N—($C_1$-$C_{24}$ alkyl), N—($C_5$-$C_{24}$ aryl)-substituted thiocarbamoyl, carbamido (—NH—(CO)—NH₂), cyano (—C≡N), cyanato (—O—C≡N), thiocyanato (—S—C≡N), formyl (—(CO)—H), thioformyl (—(CS)—H), amino (—NH₂), mono-($C_1$-$C_{24}$ alkyl)-substituted amino, di-($C_1$-$C_{24}$ alkyl)-substituted amino, mono-($C_5$-$C_{24}$ aryl)-substituted amino, di-($C_5$-$C_{24}$ aryl)-substituted amino, $C_2$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO₂), nitroso (—NO), sulfo (—SO₂—OH), sulfonato (—SO₂—O⁻), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO₂-alkyl), $C_5$-$C_{24}$ arylsulfonyl (—SO₂-aryl), boryl (—BH₂), borono (—B(OH)₂), boronato (—B(OR)₂ where R is alkyl or other hydrocarbyl), phosphono (—P(O)(OH)₂), phosphonato (—P(O)(O⁻)₂), phosphinato (—P(O)(O⁻)), phospho (—PO₂), phosphino (—PH2); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), and $C_5$-$C_{24}$ aryl (preferably $C_5$-$C_{14}$ aryl). In some implementations, the substituents as used herein are halogen, $C_1$-$C_4$ alkyl, $C_1$-$C_4$ haloalkyl, $C_1$-$C_4$ heteroalkyl, $C_1$-$C_6$ alkoxy, mono($C_1$-$C_6$alkyl)amino or di($C_1$-$C_6$alkyl)amino.

In addition, the functional groups as described herein may, if a particular group permits, be further substituted with one or more additional functional groups or with one or more hydrocarbyl moieties such as those specifically enumerated herein. Analogously, the hydrocarbyl moieties described herein may be further substituted with one or more functional groups or additional hydrocarbyl moieties such as those specifically enumerated.

LSF

The term "inhibit LSF" as used herein refers to inhibiting expression (level) of LSF and/or biological activity of LSF. In some implementations, the term "inhibit LSF" refers to a decrease in the protein level of LSF and/or gene transcript level of LSF. For example, inhibition of LSF can result in a reduction in the gene expression of TFCP2 encoding LSF. The term "inhibit LSF" also refers to a down-regulation or an inhibition of biological activity of LSF, e.g. the function of LSF to modulate expression of LSF-regulated downstream genes such as; thymidylate synthetase (TYMS), secreted phosphoprotein 1 (SPP1), complement factor H (CFH) and fibronectin 1 (FN1) (see Porta-de-la-Riva M, et al (2011) J. Biochem. 435:563-8, which is incorporated herein in its entirety by reference).

The terms "cellular LSF activity" and "biological activity of LSF" are used herein interchangeably. Both terms refer to the ability of LSF to regulate cellular processes downstream of LSF, for example, to modulate the expression of genes that are downstream of LSF. In some implementations, the biological activity of LSF can elicit a stimulatory effect on expression of LSF-downstream genes. In other implementations, the biological activity of LSF can induce an inhibitory effect on expression of LSF-downstream genes. In yet other implementations, the biological activity of LSF may be due to interactions with other cellular proteins.

The phrase "level of LSF" as used herein encompasses the expression and/or biological activity of LSF. As described herein, the term "expression" refers to the amount of the protein obtained by translation of RNA transcribed from a gene, and/or the amount of RNA transcribed from a gene.

The term "regulate" used herein in reference to expression of a gene, refers to producing an effect on, for example, gene expression. In some implementations, the effect can be stimulatory, such as increasing expression of a gene. In some implementations, the effect can be inhibitory, such as decreasing expression of a gene. The terms "regulate" and "modulate" are interchangeably used herein.

The terms "inhibitors of LSF" and "LSF inhibitors" used interchangeably herein, generally refers to agents that inhibit LSF. Inhibitors of LSF according to some implementation are chemical entities or molecules that can inhibit expression of LSF and/or biological activity of LSF, as disclosed herein, for example, compounds of any of Formula (I) and enantiomers, prodrugs, derivatives and pharmaceutically acceptable salts thereof, which are discussed further in the section Inhibitors of LSF.

The ability of a compound to inhibit LSF can be assessed by measuring a decrease in expression of LSF as compared to the level of LSF in the absence of inhibitors of LSF. In some implementations, the ability of a compound to inhibit LSF can be assessed by measuring a decrease in the biological activity, e.g., transcriptional activity of LSF as compared to the level of transcriptional activity of LSF in the absence of inhibitors of LSF. The expression of LSF includes the amount of RNA transcribed from a gene, e.g. TFCP2 that encodes LSF, and/or the amount of LSF proteins that is obtained by translation of RNA transcribed from a gene, e.g. TFCP2. For example, a LSF inhibitor as disclosed herein can inhibit expression of LSF by at least about 10%, at least about 15%, at least about 20%, at least about 30%, at least about 40%, at least about 50%, at least about 60%, at least about 70%, at least about 80%, at least about 90%, 95%, 99% or even 100%, as compared to a reference level in the absence of a LSF inhibitor.

Additionally, ability of a compound to inhibit LSF can be also assessed by measuring a decrease in or an inhibition of biological activity of LSF as compared to a negative control, e.g. the experimental condition in the absence of LSF inhibitors. The biological activity of LSF can refer to the ability of LSF to modulate expression of LSF-targeted genes such as thymidylate synthase (TYMS) and/or LSF-downstream genes, such as secreted phosphoprotein 1 (SPP1), complement factor H (CFH) and other tumor-associated genes (see Yoo et al., PNAS, 2010, 107; 8357-8362, which is incorporated herein in its entirety by reference). Accordingly, a LSF inhibitor as disclosed herein can inhibit biological activity of LSF, such as a decrease in expression of SPP1 that encodes OPN (also known as secreted phosphoprotein 1, SPP1), by at least about 10%, at least about 15%, at least about 20%, at least about 30%, at least about 40%, at least about 50%, at least about 60%, at least about 70%, at least about 80%, at least about 90%, 95%, 99% or even 100%, as compared to a reference level in the absence of a LSF inhibitor. In some implementations, ability of a compound to inhibit LSF is assessed by inhibition of LSF-induced tumorigenesis and metastasis of cancer cells, e.g. hepatocellular carcinoma cells in vitro or in an in vivo animal model as demonstrated in the Examples herein, as compared to a reference condition without treatment with such a LSF inhibitor. In such implementations, a LSF inhibitor can decrease a tumor weight and volume by at least about 15%, at least about 20%, at least about 30%, at least about 40%, at least about 50%, at least about 60%, at least about 70%, at least about 80%, at least about 90%, 95%, 99% or even 100%, as compared to no treatment with a LSF inhibitor.

Disorders and Diseases

The term 'disorder' or 'disease' used interchangeably herein, refers to any alteration in the state of the body or of some of its organs, interrupting or disturbing the performance of the functions and/or causing symptoms such as discomfort, dysfunction, distress, or even death to the person afflicted or those in contact with the person. A disease or disorder can also relate to distemper, ailing, ailment, malady, disorder, sickness, illness, complaint, indisposition, affection. In one implementation, the disorder or disease is cancer. In one implementation, the disease or disorder is liver cancer, e.g., hepatocellular carcinoma. In one implementation, the disease or disorder is a cancer selected from the group selected from: colon cancer, breast cancer, ovarian cancer, melanoma, endometrium cancer, pancreatic cancer, prostate cancer, bone cancer, kidney cancer, leukemia, large intestine cancer, lung cancer, small cell lung carcinoma (SSLC), stomach cancer and other cancers.

The term 'cancer' and 'malignancy' are used interchangeably herein, and refer to a disease that is characterized by uncontrolled, abnormal growth of cells. Cancer cells can spread locally or through the bloodstream and lymphatic system to other parts of the body. The term is also intended to include any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer. The term cancer also includes metastases which are cancer cells (e.g. a primary tumor, or a metastasis tumor) which has migrated to other locations in the subject and to establish new tumors at such locations. A small molecule LSF inhibitor as disclosed herein which "inhibits" cancer metastasis may result in the delayed appearance of secondary tumors, slowed development of primary or secondary tumors, decreased occurrence of secondary tumors, slowed or decreased severity of secondary effects of disease, arrested tumor growth and regression of tumors, among others. In the extreme, complete inhibition is referred to herein as prevention (e.g., virtually complete inhibition, no metastasis if it had not occurred, no further metastasis if there had already been metastasis of a cancer, or virtually complete inhibition of the growth of a primary tumor caused by re-seeding of the tumor by a metastasized cell.

A "cancer cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage dependence, proliferation, malignancy, contact inhibition and density limitation of growth, growth factor or serum dependence, tumor specific markers levels, invasiveness, tumor growth or suppression in suitable animal hosts such as nude mice, and the like, in vitro, in vivo, and ex vivo (see also Freshney, Culture of Animal Cells: A Manual of Basic Technique (3rd ed. 1994)).

A "tumorigenic cell," as used herein, is a cell that, when introduced into a suitable site in a subject, can form a tumor. The cell may be non-metastatic or metastatic. A variety of types of tumorigenic and/or metastatic cells can be used in a method according to some implementations, including cells from metastatic epithelial cancers, carcinomas, melanoma, leukemia, etc. The tumor cells may be, e.g., from cancers of breast, lung, colon, bladder, prostate, liver, gastrointestinal tract, endometrium, tracheal-bronchial tract, pancreas, liver, uterus, ovary, nasopharynges, prostate, bone or bone marrow, brain, skin or other suitable tissues or organs. In an implementation, the cancer cells are of human origin.

The term "tumor" or "tumor cell" are used interchangeably herein, refers to the tissue mass or tissue type of cell that is undergoing abnormal proliferation.

A "metastatic" cell, as used herein, refers to a cell that has a potential for metastasis and, when used in a methods according to some implementations, is able to seed a tumor or a cell colony of interest. A "highly metastatic" cell, as used herein, refers to a cell that has a high potential for metastasis; e.g., cells from a cell line such as, but not limited to LM2, MDA-MB-231, PC-3, DU-145, Lewis Lung carcinoma, as described herein, can be considered to be highly metastatic cells. Metastatic cells can be generated in a variety of ways, which are discussed further below.

A "sarcoma" refers to a type of cancer cell that is derived from connective tissue, e.g., bone (osteosarcoma) cartilage (chondrosarcoma), muscle (rhabdomyosarcoma or rhabdosarcoma), fat cells (liposarcoma), lymphoid tissue (lymphosarcoma), collagen-producing fibroblasts (fibrosarcoma). Sarcomas may be induced by infection with certain viruses, e.g., Kaposi's sarcoma, Rous sarcoma virus, etc.

The term "tissue" is intended to include intact cells, blood, blood preparations such as plasma and serum, bones, joints, muscles, smooth muscles, and organs. In some implementations, the tissue is liver tissue.

The term "subject" includes human and other mammalian subjects that receive either prophylactic or therapeutic treatment. The term "subject" and "individual" are used interchangeably herein, and refer to an animal, for example a human, to whom treatment, including prophylactic treatment, with the cells according to some implementations, is provided. The "non-human animals" according to some implementations include mammals such as rats, mice, rabbits, sheep, cats, dogs, cows, pigs, and non-human primates.

The terms "a reference sample" or "a reference level" as used interchangeably herein refer to a negative control of the condition. For example, in the context of treatment, a reference level is the level if a subject is not treated. In some implementations, a reference level in the context of diagnosis is the level present in a normal healthy subject. The term "normal healthy subject" refers to a subject who has no symptoms of any diseases or disorders, or who is not identified with any diseases or disorders, or who is not on any medication treatment, or a subject who is identified as healthy by physicians based on medical examinations. In some implementations, a reference level or sample used herein refers to the level measured at a previous time point from a subject being treated.

The terms "treat", "treatment" and "treating" used interchangeably, with respect to treatment of a disease or disorder, mean preventing the development of the disease, or altering the course of the disease (for example, but not limited to, slowing the progression of the disease), or reversing a symptom of the disease or reducing one or more symptoms and/or one or more biochemical markers in a subject, preventing one or more symptoms from worsening or progressing, promoting recovery or improving prognosis in a subject who is at risk of the disease, as well as slowing or reducing progression of existing disease. The term treating encompasses reducing or alleviating at least one adverse effect or symptom of a condition, disease or disorder associated with inappropriate proliferation, for example cancer. As used herein with respect to cancer, the term treating is used to refer to the reduction of a symptom and/or a biochemical marker of in appropriate proliferation, for example a reduction in at least one biochemical marker of cancer by at least 10%. For example, but are not limited to, a reduction in a biochemical marker of cancer, for example a reduction in, as an illustrative example only, at least one of the following biomarkers; CD44, telomerase, TGF-α, TGF-β, erbB-2, erbB-3, MUC1, MUC2, CK20, PSA, CA125, FOBT, by 10%, or a reduction in the rate of proliferation of the cancer cells by 10%, would be considered effective treatments by the methods as disclosed herein. As alternative examples, a reduction in a symptom of cancer, for example, a slowing of the rate of growth of the cancer by 10% or a cessation of the increase in tumor size, or a reduction in the size of a tumor by 10% or a reduction in the tumor spread (i.e. tumor metastasis) by 10% would also be considered as an effective treatment by the methods as disclosed herein. In other implementations, treatment can be therapeutic in terms of eliminating or reducing at least one symptom of the condition or disease. For example, in the case of HCC, therapeutic treatment refers to inhibiting or delaying the progression of HCC in a subject that is already inflicted with HCC. Measurable lessening includes any statistically significant decline in a measurable marker or symptom, such as measuring a tumor size or level of a biomarker.

As used herein, the term "treating" includes preventing the progression and/or reducing or reversing at least one adverse effect or symptom of a condition, disease or disorder associated with inappropriate proliferation, for example cancer. Accordingly, in some implementations, treatment can be prophylactic in terms of completely or partially preventing a disease or sign or symptom of cancer. For example, subjects at high risk of cancer, e.g., HCC, such as HBV or HCV, can be subjected to prophylactic treatment to prevent the onset of HCC. In some implementations, prophylactic treatment can be administered to subjects who had prior treatment of a disease and the disease is in remission. For example, for subjects who have their HCC tumors removed or stabilized by previous therapeutic methods can be prophylactically treated (e.g. with a LSF inhibitor as disclosed herein) to prevent the recurrence and metastasis of HCC.

As used herein, the terms "prevent," "preventing" and "prevention" refer to the avoidance or delay in manifestation of one or more symptoms or measurable markers of a disease or disorder. A delay in the manifestation of a symptom or marker is a delay relative to the time at which such symptom or marker manifests in a control or untreated subject with a similar likelihood or susceptibility of developing the disease or disorder. The terms "prevent," "preventing" and "prevention" include not only the complete avoidance or prevention of symptoms or markers, but also a reduced severity or degree of any one of those symptoms or markers, relative to those symptoms or markers arising in a control or non-treated individual with a similar likelihood or susceptibility of developing the disease or disorder, or relative to symptoms or markers likely to arise based on historical or statistical measures of populations affected by the disease or disorder. By "reduced severity" is meant at least a 10% reduction in the severity or degree of a symptom or measurable disease marker, relative to a control or reference, e.g., at least 15%, 20%, 30%, 40%, 50%, 60%, 70%, 80%, 90%, 95%, 99% or even 100% (i.e., no symptoms or measurable markers).

The terms "up-regulate", "increase" or "activate" are all used herein to generally mean an increase by a statically significant amount; for the avoidance of any doubt, the terms "up-regulate", "increase" or "higher" means an increase of at least 10% as compared to a reference level, for example an increase of at least about 20%, or at least about 30%, or at least about 40%, or at least about 50%, or at least about 60%, or at least about 70%, or at least about 80%, or at least about 90% or a 100% increase or more, or any increase between 10-100% as compared to a reference level, or an increase greater than 100%, for example, an increase at least about a 2-fold, or at least about a 3-fold, or at least about a 4-fold, or at least about a 5-fold or at least about a 10-fold increase, or any increase between 2-fold and 10-fold or greater as compared to a reference level. When "increase" is used in the context of the expression or activity of a gene or protein, it refers to a positive change in protein or nucleic acid level or activity in a cell, a cell extract, or a cell supernatant. For example, such an increase may be due to increased RNA stability, transcription, or translation, or decreased protein degradation. Preferably, this increase is at least 5%, at least about 10%, at least about 25%, at least about 50%, at least about 75%, at least about 80%, at least about 100%, at least about 200%, or even about 500% or more over the level of expression or activity under control conditions.

The terms "lower", "reduced", "reduction" or "decrease", "down-regulate" or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level. When "decrease" or "inhibition" is used in the context of the level of expression or activity of a gene or a protein, e.g. LSF, it refers to a reduction in protein or nucleic acid level or activity in a cell, a cell extract, or a cell supernatant. For example, such a decrease may be due to reduced RNA stability, transcription, or translation, increased protein degradation, or RNA interference. In some implementations, the small-molecule LSF inhibitors as disclosed herein decrease the activity or expression of LSF. Preferably, this decrease is at least about 5%, at least about 10%, at least about 25%, at least about 50%, at least about 75%, at least about 80%, or even at least about 90% of the level of expression or activity under control conditions. The term "level" as used herein in reference to LSF refers to expression or activity of LSF.

The terms "significantly different than,", "statistically significant," and similar phrases refer to comparisons between data or other measurements, wherein the differences between two compared individuals or groups are evidently or reasonably different to the trained observer, or statistically significant (if the phrase includes the term "statistically" or if there is some indication of statistical test, such as a p-value, or if the data, when analyzed, produce a statistical difference by standard statistical tests known in the art).

Formulations

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (24) $C_2$-$C_{12}$ alcohols, such as ethanol; and (25) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Useful pharmaceutical carriers for the preparation of the compositions hereof, can be solids, liquids or gases. Suitable pharmaceutical carriers and their formulation are described in Remington's Pharmaceutical Sciences by E. W. Martin. Such compositions will, in any event, contain an effective amount of the compounds of Formula (I) together with a suitable carrier so as to prepare the proper dosage form for proper administration to the recipient.

Liquid dosage forms for oral administration include, but are not limited to, pharmaceutically acceptable emulsions, microemulsions, solutions, suspensions, syrups and elixirs. In addition to the compounds of Formula (I), the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the compounds of Formula (I) are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcelhdose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monosteamte, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard-filled gelatin capsules using such excipients as lactose or milk sugar as well as high molecular weight polyethylene glycols, and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type can also be employed as fillers in soft and hard-filled gelatin capsules using such excipients as lactose or milk sugar as well as high molecular weight polethylene glycols, and the like.

The compounds of Formula (I) can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the compounds of Formula (I) can be admixed with at least one inert diluent such as sucrose, lactose or starch. Such dosage forms can also comprise, as in normal practice, additional substances other than inert diluents, e.g., tableting lubricants and other tableting aids such as magnesium stearate and microcrystalline cellulose. In the case of capsules, tablets and pills, the dosage forms can also comprise buffering agents. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for parenteral administration conveniently include sterile aqueous preparations of the agents that are preferably isotonic with the blood of the recipient. Suitable excipient solutions include phosphate buffered saline, saline, water, lactated Ringer's or dextrose (5% in water). Such formulations can be conveniently prepared by admixing the agent with water to produce a solution or suspension, which is filled into a sterile container and sealed against bacterial contamination. Preferably, sterile materials are used under aseptic manufacturing conditions to avoid the need for terminal sterilization. Such formulations can optionally contain one or more additional ingredients, which can include preservatives such as methyl hydroxybenzoate, chlorocresol, metacresol, phenol and benzalkonium chloride. Such materials are of special value when the formulations are presented in multidose containers.

Buffers can also be included to provide a suitable pH value for the formulation. Suitable buffer materials include sodium phosphate and acetate. Sodium chloride or glycerin can be used to render a formulation isotonic with the blood.

If desired, a formulation can be filled into containers under an inert atmosphere such as nitrogen and can be conveniently presented in unit dose or multi-dose form, for example, in a sealed ampoule.

Those skilled in the art will be aware that the amounts of the various components of the compositions according to some implementations to be administered in accordance with the method described herein to a subject will depend upon those factors noted above.

Injectable preparations, for example, sterile injectable aqueous or oleaginous suspensions can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable media prior to use.

In order to prolong the effect of a drug, it is often desirable to slow the absorption of the drug from subcutaneous or intramuscular injection. This can be accomplished by the use of a liquid suspension or crystalline or amorphous material with poor water solubility. The rate of absorption of the drug then depends upon its rate of dissolution that, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of Formula (I) with suitable non-irritating excipients or carriers such as cocoa butter, polyethylene glycol, or a suppository wax which are solid at ambient temperature but liquid at body temperature and therefore melt in the rectum or vaginal cavity and release the active compound.

A typical suppository formulation includes the compound or a pharmaceutically acceptable salt thereof which is active when administered in this way, with a binding and/or lubricating agent, for example, polymeric glycols, gelatins, cocoa-butter, or other low melting vegetable waxes or fats. Typical transdermal formulations include a conventional aqueous or nonaqueous vehicle, for example, a cream, ointment, lotion, or paste or are in the form of a medicated plastic, patch or membrane.

Typical compositions for inhalation are in the form of a solution, suspension, or emulsion that can be administered in the form of an aerosol using a conventional propellant such as dichlorodifluoromethane or trichlorofluoromethane.

Formulations of the compositions described herein include those suitable for topical administration. The formulations may conveniently be presented in unit dosage form and may be prepared by any methods well known in the art of pharmacy. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, ointments, pastes, emulsions, sprays, creams, lotions, slurries, suspensions, foams, controlled release formulations, gels, patches, implants, water-oil bilayer compositions, water-oil-powder trilayer compositions, serums, powders, mousses, hydrogels, single-use applicators, and the like, suitable for topical administration to the patient. The topical formulation can be delivered by way of a transdermal patch.

Compounds of Formula (I) also include pharmaceutically acceptable salts thereof. As used herein, the term "pharmaceutically-acceptable salts" refers to the conventional non-toxic salts or quaternary ammonium salts of LSF inhibitors as disclosed herein, e.g., from non-toxic organic or inorganic acids. These salts can be prepared in situ in the administration vehicle or the dosage form manufacturing process, or by separately reacting a LSF inhibitor in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), content of which is herein incorporated by reference in its entirety.

In some implementations of the aspects described herein, representative pharmaceutically acceptable salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

Derivatives and Prodrugs

The term "derivative" as used herein refers to a chemical substance related structurally to another, i.e., an "original" substance, which can be referred to as a "parent" compound. A "derivative" can be made from the structurally-related parent compound in one or more steps. The general physical and chemical properties of a derivative are also similar to the parent compound.

In some implementations, the compositions include prodrugs of compounds selected from Formula (I). As used herein, a "prodrug" refers to a compound that can be converted via some chemical or physiological process (e.g., enzymatic processes and metabolic hydrolysis) to a compound selected from the group consisting of compounds of Formula (I).

Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxyl, amino or mercapto group is bonded to any group that, when the prodrug of the active compound is administered to a subject, cleaves to form a free hydroxyl, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design*. 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs-principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", *Arfv. Drug Delivery Rev.* 8(1): 1-38 (1992); Fleisher et al. "Improved oral drug delivery: solubility limitations overcome by the use of prodrugs", *Arfv. Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs*, [*Symp.*] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), content of all of which is herein incorporated by reference in its entirety.

Other than in the operating examples, or where otherwise indicated, all numbers expressing quantities of ingredients or reaction conditions used herein should be understood as modified in all instances by the term "about." The term "about" when used in connection with percentages can mean±1%. The present invention is further explained in detail by the following, including the Examples, but the scope of the invention should not be limited thereto.

The term "consisting of" refers to compositions, methods, and respective components thereof as described herein, which are exclusive of any element not recited in that description of the implementation.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean±1%. The present invention is further explained in detail by the following, including the Examples, but the scope of the invention should not be limited thereto.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

It is understood that the foregoing detailed description and the following examples are illustrative only and are not to be taken as limitations upon the scope of the invention. Various changes and modifications to the disclosed implementations, which will be apparent to those of skill in the art, may be made without departing from the spirit and scope of the present invention. Further, all patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLES

General Reactions Schemes.

Compounds having Formula (I) can be made by convergent methods. Some examples are shown by Schemes 1, 2 and 3 for the preparation of the compound (II)

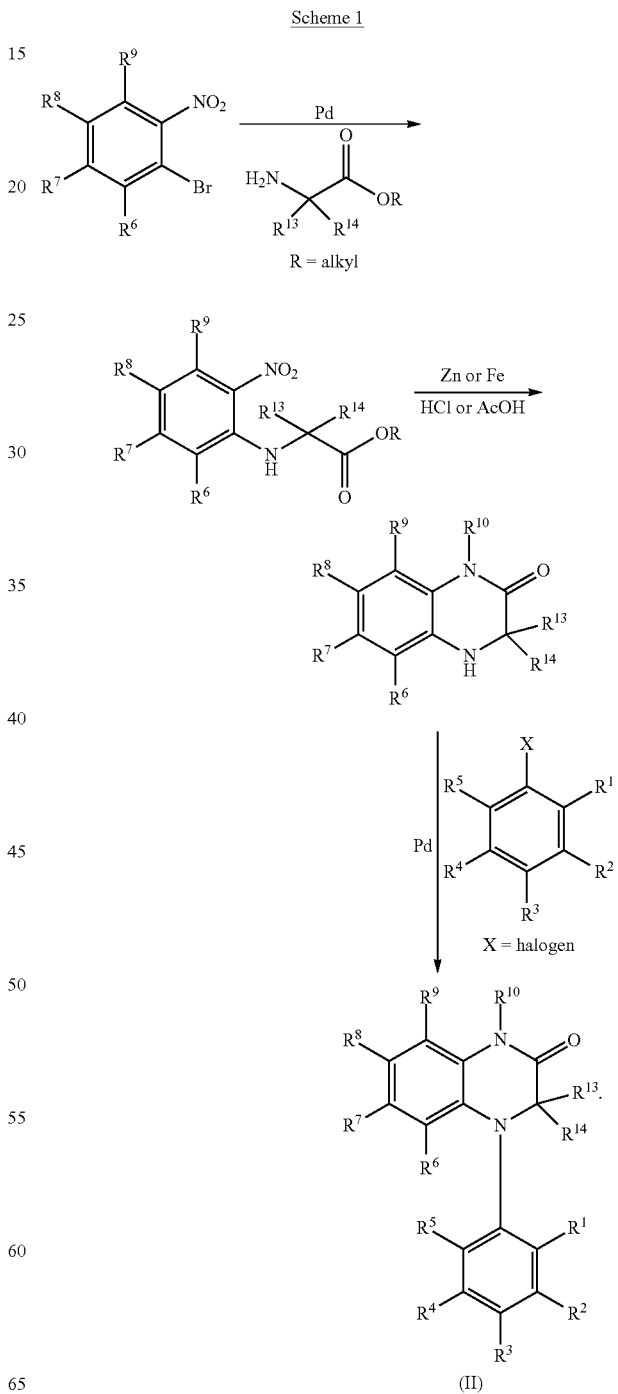

67

Scheme 2

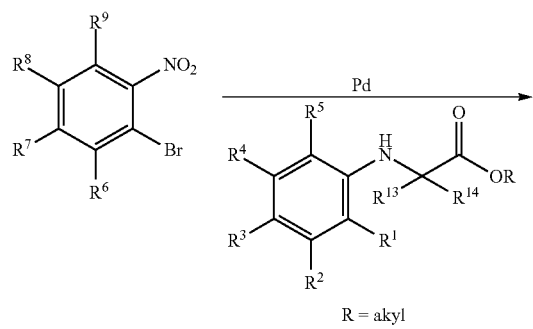

R = akyl

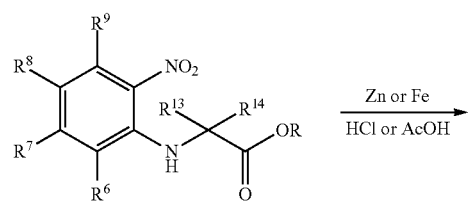

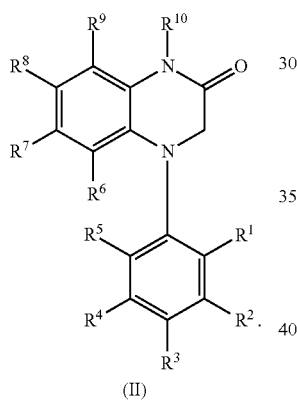

(II)

Scheme 3

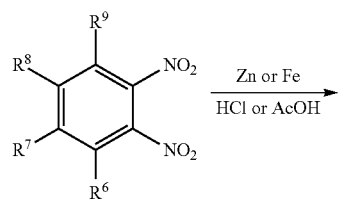

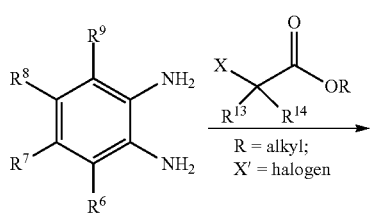

68

-continued

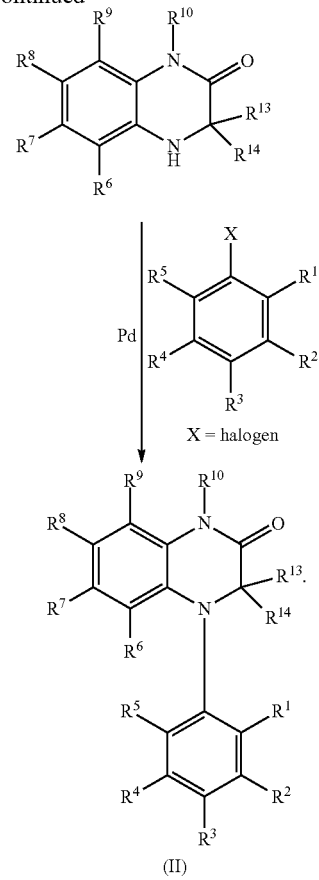

(II)

Synthesis of Exemplary Compounds

Exemplary compounds were synthesized as follows:

5-bromo-6-nitrobenzo[d][1,3]dioxole

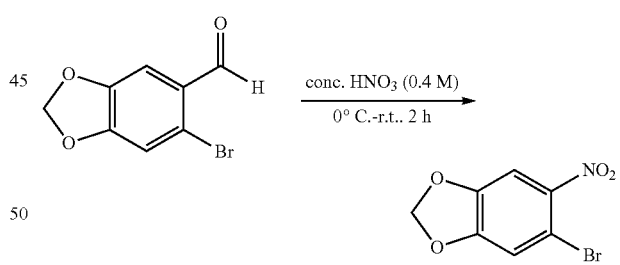

To a 100-mL round bottomed flask quipped with a magnetic Teflon-coated stir bar was added conc. nitric acid (33 mL). The reaction flask was cooled in an ice-water bath. With stirring, 6-bromobenzo[d][1,3]dioxole-5-carbaldehyde (4.58 g, 20 mmol) was added in small portions over 5 minutes. The reaction mixture was stirred at room temperature for 2 hours. Then, the mixture was poured into a 500-mL Erlenmeyer flask filled with 200 mL water cooled in an ice-water bath, forming a yellow precipitate. The slurry was filtered via vacuum filtration and the solid was rinsed with water (50 mL), and dried under reduced pressure to obtain 5-bromo-6-nitrobenzo[d][1,3]dioxole as a pale yellow solid (4.37 g, 89% yield). $^1$H NMR (CDCl$_3$, 400 MHz) δ 7.43 (s, 1H), 7.12 (s, 1H), 6.15 (s, 2H).

N-(2-ethoxyphenyl)-6-nitrobenzo[d][1,3]dioxol-5-amine

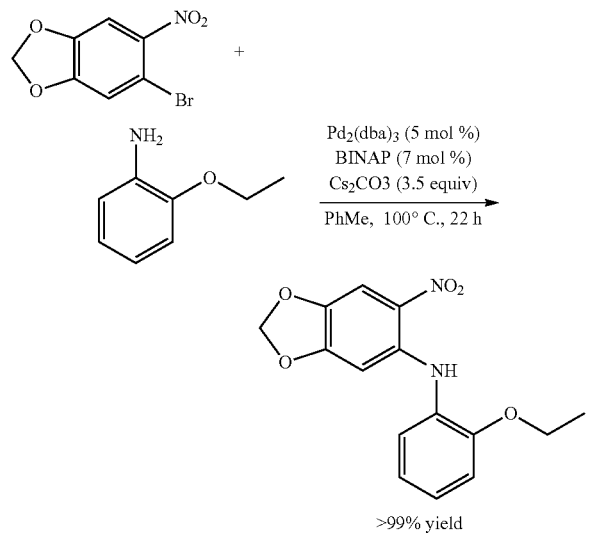

>99% yield

To a flame-dried 25-mL round bottomed flask equipped with a magnetic Teflon-coated stirbar and flushed with argon was added 5-bromo-6-nitrobenzo[d][1,3]dioxole (300 mg, 1.22 mmol) and dry toluene (4 mL, 0.3 M). Then, Pd$_2$(dba)$_3$ (56 mg, 0.061 mmol, 5 mol %), rac-BINAP (53 mg, 0.085 mmol. 7 mol %), and cesium carbonate (1.39 g, 4.27 mmol, 3.5 equiv) were added, and the flask was fitted with a water condenser. The reaction was stirred at 100° C. for 8 hours. Then, the reaction mixture was cooled to room temperature and concentrated via rotary evaporation. The crude product was purified via silica gel chromatography (3:1 hexanes: ethyl acetate) to afford N-(2-ethoxyphenyl)-6-nitrobenzo[d][1,3]dioxol-5-amine as a red solid (369 mg, >99% yield). $^1$H NMR (CDCl$_3$, 400 MHz) δ 10.10 (s, 1H), 7.64 (s, 1H), 7.34 (dd, J=8.1, 1.7 Hz, 1H), 7.15 (ddd, J=7.8, 7.8, 1.7 Hz, 1H), 7.00-6.94 (overlap, 2H), 6.71 (s, 1H), 5.98 (s, 2H), 4.09 (q, J=7.0 Hz, 2H), 1.41 (t, J=7.0 Hz, 3H).

Attempted Synthesis (1) of ethyl N-(2-ethoxyphenyl)-N-(6-nitrobenzo[d][1,3]dioxol-5-yl)glycinate

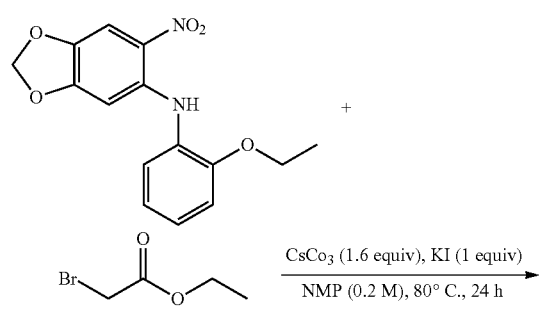

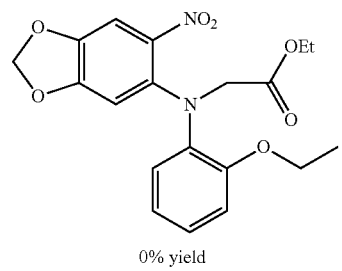

0% yield

To an oven-dried 10-mL round bottomed flask equipped with a Teflon-coated stir bar and flushed with argon was added N-(2-ethoxyphenyl)-6-nitrobenzo[d][1,3]dioxol-5-amine (151 mg, 0.50 mmol) and anhydrous NMP (2.50 mL, 0.20 M). Cesium carbonate (261 mg, 0.80 mmol, 1.6 equiv), potassium iodide (83 mg. 0.50 mmol, 1 equiv), and ethyl bromoacetoacetate (0.11 mL, 1.0 mmol, 2 equiv) were added and the reaction flask was fitted with a reflux condenser and heated to 80° C. for 20 hours. No reaction occurred and the desired product ethyl N-(2-ethoxyphenyl)-N-(6-nitrobenzo[d][1,3]dioxol-5-yl)glycinate was not isolated (0% yield).

Attempted Synthesis (2) of ethyl N-(2-ethoxyphenyl)-N-(6-nitrobenzo[d][1,3]dioxol-5-yl)glycinate

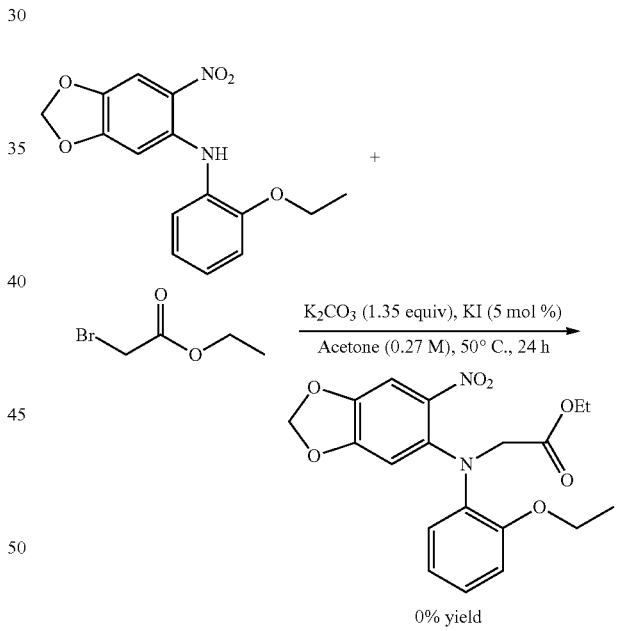

0% yield

To an oven-dried 10-mL round bottomed flask equipped with a Teflon-coated stir bar and flushed with argon was added N-(2-ethoxyphenyl)-6-nitrobenzo[d][1,3]dioxol-5-amine (151 mg, 0.50 mmol) and reagent grade acetone (1.85 mL, 0.27 M). Vacuum-oven dried potassium carbonate (93 mg, 0.675 mmol, 1.35 equiv), potassium iodide (4 mg, 0.025 mmol, 5 mol %), and ethyl bromoacetoacetate (0.066 mL, 0.60 mmol, 1.2 equiv) were added and the reaction flask was heated to 50° C. for 24 hours. No reaction occurred and the desired product ethyl N-(2-ethoxyphenyl)-N-(6-nitrobenzo[d][1,3]dioxol-5-yl)glycinate was not isolated (0% yield).

Attempted Synthesis (3) of ethyl N-(2-ethoxyphenyl)-N-(6-nitrobenzo[d][1,3]dioxol-5-yl)glycinate

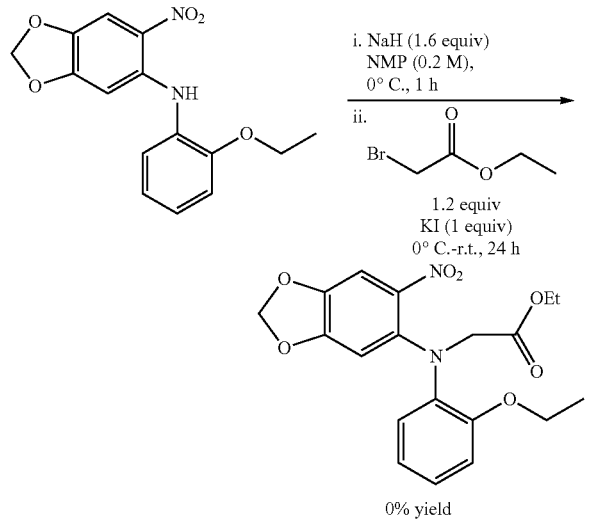

0% yield

To an oven-dried 10-mL round bottomed flask equipped with a Teflon-coated stir bar and flushed with argon was added sodium hydride (32 mg, 0.8 mmol, 60% in oil dispersion, 1.6 equiv) and NMP (1.25 mL). The flask was cooled to 0° C. In a separate oven-dried 5 mL round bottomed flask, N-(2-ethoxyphenyl)-6-nitrobenzo[d][1,3]dioxol-5-amine (173 mg, 0.5 mmol) was dissolved in NMP (1.25 mL). This solution was slowly added via syringe to the reaction flask and the mixture was stirred at 0° C. for 1 hour. The reaction mixture was warmed to room temperature for 15 minutes, and cooled back to 0° C. Ethyl bromoacetoacetate (0.066 mL, 0.6 mmol, 1.2 equiv) was added dropwise to the reaction flask. The reaction was stirred at 0° C. and allowed to warm to room temperature for a total of 24 hours. No reaction occurred and the desired product ethyl N-(2-ethoxyphenyl)-N-(6-nitrobenzo[d][1,3]dioxol-5-yl)glycinate was not isolated (0% yield).

2-chloro-N-(6-((2-ethoxyphenyl)amino)benzo[d][1,3]dioxol-5-yl)acetamide

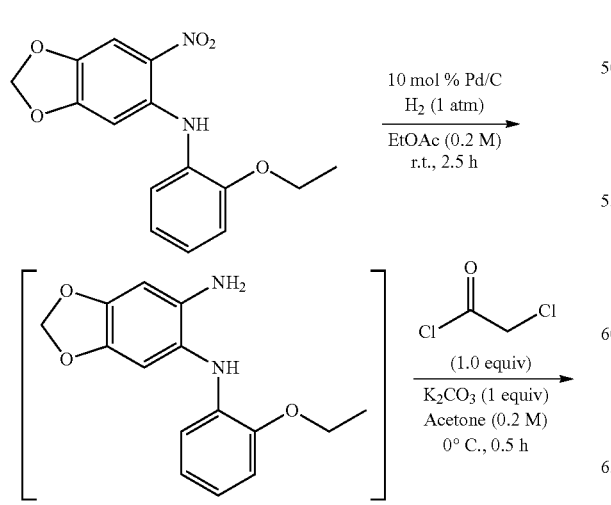

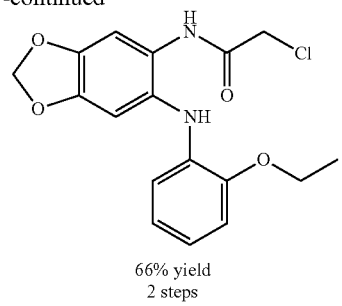

66% yield
2 steps

To a flame dried 25-mL round bottomed flask equipped with a magnetic Teflon-coated stir bar and flushed with argon was added with N-(2-ethoxyphenyl)-6-nitrobenzo[d][1,3]dioxol-5-amine (302 mg, 1.0 mmol) and 2-MeTHF (5 mL, 0.2 M). Then, Pd/C (106 mg, 0.1 mmol, 10 mol %, 10% Pd) was added to the flask, and the flask was fitted with a three-way T adapter. Then, the flask was flushed with hydrogen gas during three vacuum/flush cycles. The reaction was left stirring at room temperature for 2 hours until no more starting material was seen by TLC (3:1 Hexanes:Ethyl acetate). Then, the hydrogen balloon was removed for an argon balloon, and the flask was flushed with three vacuum/flush cycles, and the flask was cooled to 0° C. in an ice-water bath. Then, reagent grade acetone (5 mL, 0.2 M) was added, followed by vacuum-oven dried potassium carbonate (138 mg, 1.0 mmol, 1 equiv). Chloroacetyl chloride (0.08 mL, 1.0 equiv) was added via syringe and the reaction was stirred at 0° C. for 0.5 hours until no more intermediate was seen by TLC. The reaction mixture was then filtered through a pipet filled with Celite and then concentrated. The crude product was purified via column chromatography (gradient from hexanes to 3:1 hexanes: ethyl acetate) to afford 2-chloro-N-(6-((2-ethoxyphenyl)amino)benzo[d][1,3]dioxol-5-yl)acetamide (231 mg, 66% yield over 2 steps). $^1$H NMR (CDCl$_3$, 400 MHz) δ 8.87 (s, 1H), 7.83 (s, 1H), 6.85 (m, 1H), 6.79-6.72 (overlap, 2H), 6.45 (m, 1H), 5.98 (s, 2H), 4.16-4.07 (overlap, 4H), 1.46 (t, J=7.0 Hz, 3H).

8-(2-ethoxyphenyl)-7,8-dihydro-[1,3]dioxolo[4,5-g]quinoxalin-6(5H)-one

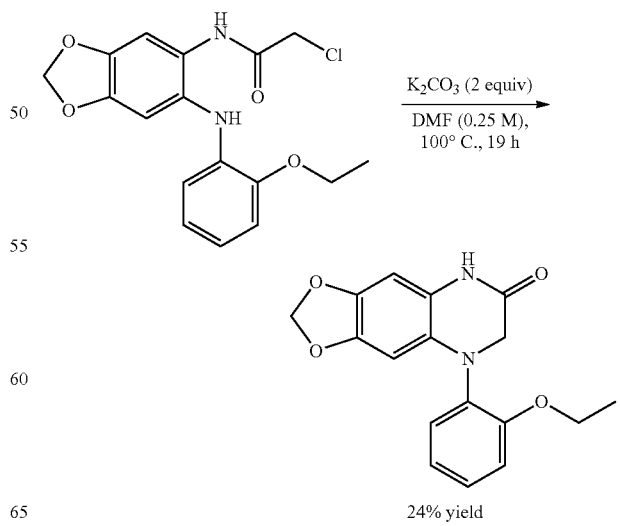

24% yield

To an oven-dried 10-mL round bottomed flask equipped with a magnetic Teflon-coated stir bar and flushed with argon was added 2-chloro-N-(6-((2-ethoxyphenyl)amino)benzo[d][1,3]dioxol-5-yl)acetamide (230 mg, 0.659 mmol) in dry DMF (2.1 mL, 0.31 M) Then, dry potassium carbonate (182 mg, 1.30 mmol 2 equiv) was added, and the flask was fitted with a water condenser and heated to 100° C. for 18 hours. Then, the reaction was poured into a separatory funnel that contained 10 mL of ice cold water. The aqueous phase was extracted with EtOAc (4×50 mL). The combined organic layers were washed with saturated aqueous sodium chloride (50 mL) and dried with anhydrous sodium sulfate ($Na_2SO_4$), filtered, and concentrated via rotary evaporation. The crude product was purified via column chromatography (1:1 hexanes:ethyl acetate) to afford 8-(2-ethoxyphenyl)-7,8-dihydro-[1,3]dioxolo[4,5-g]quinoxalin-6(5H)-one as a light brown powder (50 mg, 24% yield). 41 NMR ($CDCl_3$, 400 MHz) δ 8.62 (s, 1H), 7.89 (s, 1H), 6.85 (m, 1H), 6.79-6.74 (overlap, 2H), 6.73 (s, 1H), 6.44 (m, 1H), 5.97 (s, 2H), 5.67 (s, 1H), 4.17-4.09 (overlap, 4H), 1.47 (t, J=7.0 Hz, 3H).

3-ethoxy-N,N-dimethylaniline

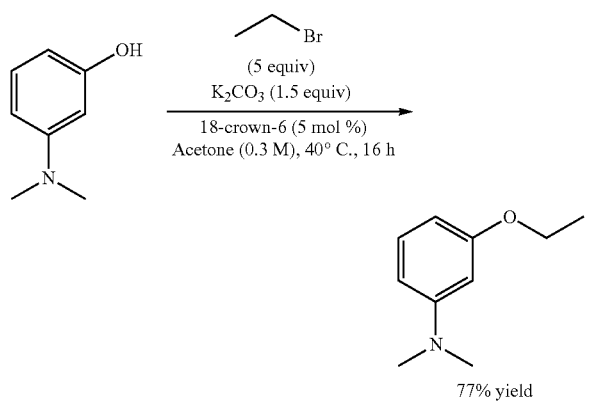

77% yield

To a flame-dried 250-mL round bottomed flask equipped with a magnetic Teflon-coated stir bar and flushed with argon was added 3-(dimethylamino)phenol (2.74 g, 20.0 mmol), and acetone (65 mL, 0.3 M) followed by the addition of anhydrous potassium carbonate (3.76 g, 27.24 mmol) and 18-crown-6 (264 mg, 1 mmol, 5 mol %). Then, bromoethane (10.9 g, 7.41 mL, 100 mmol, 5 equiv) was added via syringe. The reaction mixture was fitted with a glycol reflux condenser and heated at 40° C. for 16 hours, and then cooled to room temperature. The reaction was filtered and the filtered solid was washed with acetone. The filtrate was concentrated via rotary evaporation and the product was purified via column (gradient from hexanes to 5:1 hexanes:ethyl acetate) to afford 3-ethoxy-N,N-dimethylaniline as a clear, pale yellow liquid (2.56 g, 77% yield). $^1$H NMR ($CDCl_3$, 400 MHz) δ 7.13 (dd, J=8.7, 8.7 Hz, 1H), 6.36 (dd, J=8.7, 2.3 Hz, 1H), 6.31-6.21 (overlap, 2H), 4.03 (q, J=7.0 Hz, 2H), 2.93 (s, 6H), 1.41 (t, J=7.0, 3H).

3-ethoxy-N,N-dimethyl-4-nitrosoaniline

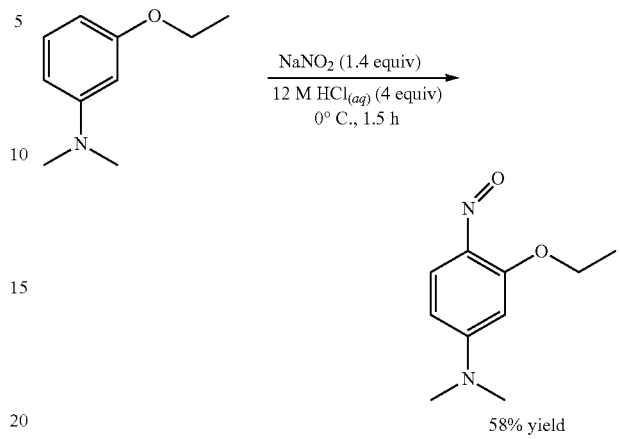

58% yield

To a 100-mL round bottomed flask equipped with a magnetic Teflon-coated stir bar was added 3-ethoxy-N,N-dimethyl-aniline (2.50 g, 15.1 mmol) was dissolved in HCl (12 M, 5.0 mL) and Water (47 mL, 0.32 M). The reaction was placed into an ice-water bath. Sodium nitrite (1.46 g, 21.2 mmol) was added portion-wise over 30 minutes, and the reaction was stirred at 0° C. for an additional hour. The reaction mixture was poured into a 500-mL Erlenmeyer flask and neutralized by the addition of saturated aqueous sodium bicarbonate (~100 mL). The mixture was diluted with 100 mL DCM, and extracted with an additional 2×~150 mL DCM. The combined organic layers were washed with saturated aqueous sodium chloride (~50 mL), dried over anhydrous sodium sulfate ($Na_2SO_4$), filtered, and concentrated via rotary evaporation to afford 3-ethoxy-N,N-dimethyl-4-nitrosoaniline as a green solid (1.72 g, 58% yield). $^1$H NMR ($CDCl_3$, 400 MHz) δ 6.67 (d, J=9.0 Hz, 1H), 6.16-6.10 (overlap, 2H), 4.44 (q, J=7.0 Hz, 2H), 3.16 (s, 6H), 1.63 (t, J=7.0 Hz, 3H).

3-ethoxy-N1,N1-dimethylbenzene-1,4-diamine

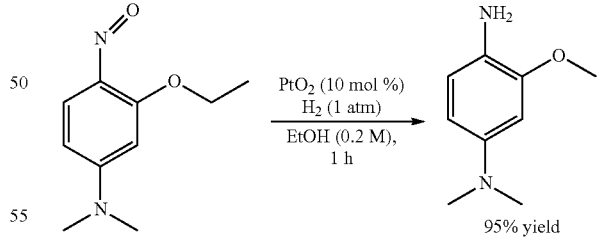

95% yield

To a flame-dried 25-mL round bottomed flask equipped with a magnetic Teflon-coated stir bar flushed with argon was added 3-ethoxy-N,N-dimethyl-4-nitrosoaniline (600 mg, 3.1 mmol), anhydrous ethanol (15.4 mL, 0.2 M), and platinum (IV) oxide (70 mg, 0.031 mmol, 10 mol %). A three-way adapter was attached and balloon full of hydrogen gas was placed on the adapter. The reaction was flushed with hydrogen gas 3 times, and allowed to stir at room temperature for one hour under hydrogen. The mixture was filtered through a pad of Celite and then concentrated via rotary evaporation and then further under high vacuum (0.4 mmHg). No further purification was needed and 3-ethoxy-N1,N1-dimethylbenzene-1,4-diamine was obtained a dark blue liquid (528 mg, 95% yield). ¹H NMR (CDCl₃, 400 MHz) δ 6.66 (d, J=8.4 Hz, 1H), 6.39 (d, J=2.6 Hz, 1H), 6.29 (dd, J=8.4, 2.6 Hz, 1H), 4.06 (q, J=7.0 Hz, 2H), 3.46 (br s, 2H), 2.82 (s, 6H), 1.43 (t, J=7.0 Hz, 3H).

2-ethoxy-N4,N4-dimethyl-N1-(6-nitrobenzo[d][1,3]dioxol-5-yl)benzene-1,4-diamine

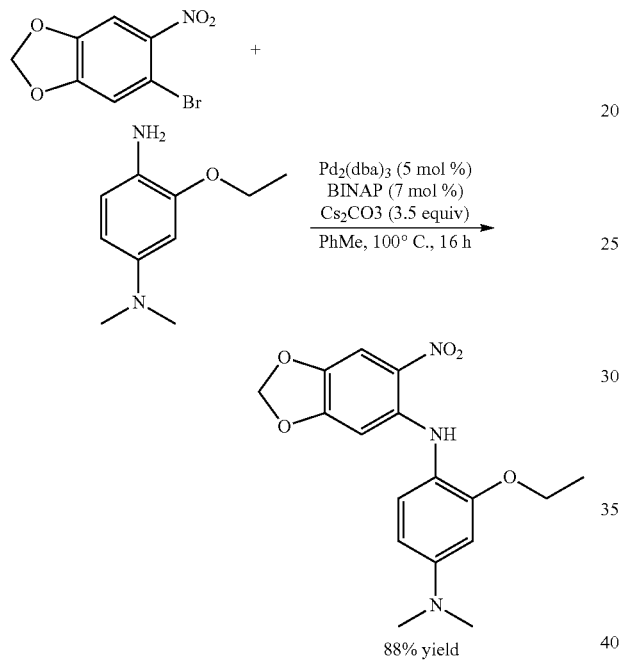

Attempted Synthesis of ethyl N-(4-(dimethylamino)-2-ethoxyphenyl)-N-(6-nitrobenzo[d][1,3]dioxol-5-yl)glycinate

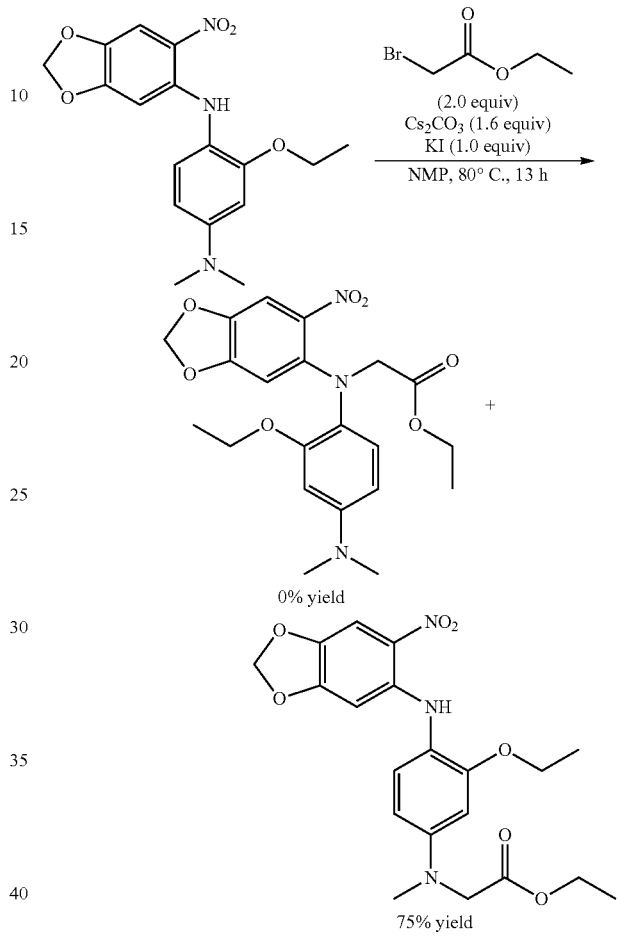

To a flame-dried 25-mL round bottomed flask equipped with a magnetic Teflon-coated stir bar and flushed with argon was added 5-bromo-6-nitrobenzo[d][1,3]dioxole (480 mg, 1.95 mmol) and dry toluene (6.50 mL, 0.3 M). Pd₂(dba)₃ (89 mg, 0.098 mmol, 5 mol %), rac-BINAP (85 mg, 0.137 mmol, 7 mol %), and cesium carbonate (2.22 g, 6.83 mmol, 3.5 equiv) were added, and the flask was flushed with argon. 3-ethoxy-N1,N1-dimethylbenzene-1,4-diamine (528 mg, 2.93 mmol, 1.5 equiv) was added and the reaction flask was fitted with a reflux condenser and allowed to stir at 100° C. overnight. The reaction mixture was cooled to room temperature, concentrated, then dry-loaded onto silica gel. The crude product was purified via column chromatography (gradient from hexanes to 3:1 hexanes: ethyl acetate) to afford 2-ethoxy-N4,N4-dimethyl-N1-(6-nitrobenzo[d][1,3]dioxol-5-yl)benzene-1,4-diamine as an red-orange solid (595 mg, 88% yield). ¹H NMR (CDCl₃, 400 MHz) δ 9.94 (s, 1H), 7.59 (s, 1H), 7.11 (d, J=8.7 Hz, 1H), 6.42 (s, 1H), 6.35-6.30 (overlap, 2H), 5.92 (s, 2H), 4.04 (q, J=7.0 Hz, 2H), 2.98 (s, 6H), 1.34 (t, J=7.0 Hz, 3H).

To a flame-dried 10-mL round bottomed flask equipped with a magnetic Teflon-coated stir bar and flushed with argon was added 2-ethoxy-N4,N4-dimethyl-N1-(6-nitro-1,3-benzodioxol-5-yl)benzene-1,4-diamine (109 mg, 317 μmol, 1.00 equiv.), cesium carbonate (206 mg, 634 μmol, 2.00 equiv.), and potassium iodide (63.2 mg, 380 μmol, 1.20 equiv.), and the flask was fitted with argon balloon and rubber septa. The solids were dissolved in NMP (1.5 mL, 0.2 M), ethyl bromoacetoacetate (0.07 mL, 63 umol, 2.0 equiv.) was added to the flask, and the mixture was heated to 80° C. for 13 hours. The reaction mixture was cooled to room temperature, poured into water (100 mL), and extracted with EtOAc (3×50 mL). The combined organic layers were washed with saturated aqueous sodium sulfate (50 mL), dried over anhydrous sodium sulfate (Na₂SO₄), filtered, and concentrated via rotary evaporation. The crude product was purified via column chromatography (1:3 hexanes:ethyl acetate) to afford ethyl N-(3-ethoxy-4-((6-nitrobenzo[d][1,3]dioxol-5-yl)amino)phenyl)-N-methylglycinate as an off-white solid (99 mg, 75% yield). ¹H NMR (400 MHz, CDCl₃) δ 9.94 (s, 1H), 7.59 (s, 1H), 7.11 (d, J=8.5 Hz, 1H), 6.43 (s, 1H), 6.28 (overlap, 2H), 5.94 (s, 2H), 4.20 (q, J=7.1 Hz, 2H), 4.07 (s, 2H), 4.02 (q, J=7.0 Hz, 2H), 3.10 (s, 3H), 1.33 (t, J=7.0 Hz, 3H), 1.26 (t, J=7.1 Hz, 4H).

5,6-dinitro-1,3-benzodioxole

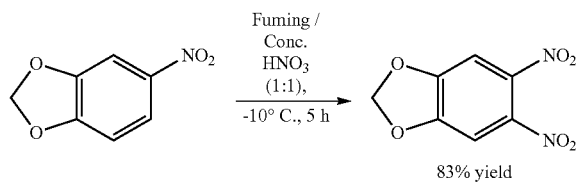 [SMILES: O=[N+]([O-])c1ccc2c(c1)OCO2 ; O=[N+]([O-])c1cc2c(cc1[N+](=O)[O-])OCO2]

83% yield

To a flame-dried 25-mL round bottomed flask equipped with a magnetic Teflon-coated stir bar and flushed with argon was added conc. nitric acid (6.0 mL) and fuming nitric acid (6.0 mL). The flask was cooled to −10° C. in an ice/acetone bath. 5-nitro-1,3-benzodioxole (579 mg, 3.46 mmol, 1.00 equiv.) was added as a single portion, and the walls of the flask were rinsed with minimal conc. nitric acid followed by minimal fuming nitric acid (~0.25 mL each). The mixture was stirred at −10° C. for 5 h. The mixture was poured into ice-cold water (150 mL), which formed a light yellow precipitate. The precipitate was collected by vacuum filtration to afford 5,6-dinitro-1,3-benzodioxole (613 mg, 83% yield) as a light yellow solid. $^1$H NMR (400 MHz, CDCl$_3$) δ 7.31 (s, 2H), 6.27 (s, 2H).

benzo[d][1,3]dioxole-5,6-diamine

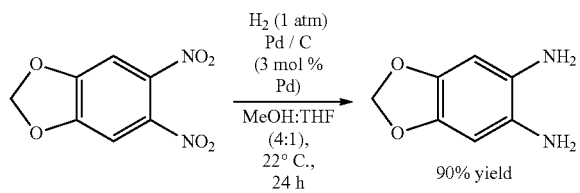 [SMILES: O=[N+]([O-])c1cc2c(cc1[N+](=O)[O-])OCO2 ; Nc1cc2c(cc1N)OCO2]

90% yield

To a flame dried 25-mL round bottomed flask equipped with a magnetic Teflon-coated stir bar and flushed with argon was added 5,6-dinitro-1,3-benzodioxole (599 mg, 2.83 mmol, 1.00 equiv.) and Pd/C (90.2 mg, 84.7 μmol, 10% Pd). The flask was fitted with a three-way T adapter equipped with an argon balloon and vacuum line. The flask was evacuated/backfilled 3 times with argon. The adapter was partially removed and under a stream of argon, methanol (16 mL) and THF (4 mL) were added to the flask by syringe, and the adapter was refitted. The argon balloon was replaced with a hydrogen balloon, and the flask evacuated/backfilled 3 times with hydrogen. The mixture was stirred at room temperature for 24 hours. The reaction mixture was filtered over Celite and rinsed with dichloromethane. The organic solution was concentrated via rotary evaporation to afford benzo[d][1,3]dioxole-5,6-diamine as an off-white solid (389 mg, 90% yield). $^1$H NMR (400 MHz, DMSO) b 6.24 (s, 2H), 5.68 (s, 2H), 4.12 (s, 4H).

7,8-dihydro-[1,3]dioxolo[4,5-g]quinoxalin-6(5H)-one

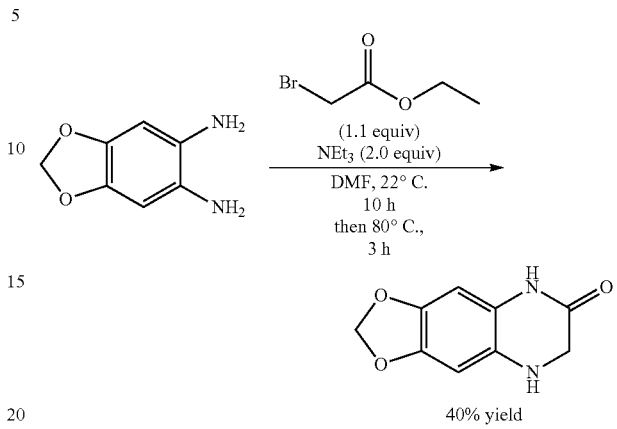

40% yield

To a flame dried 25-mL round bottomed flask equipped with a magnetic Teflon-coated stir bar and flushed with argon was added benzo[d][1,3]dioxole-5,6-diamine (840 mg, 5.52 mmol, 1.00 equiv.) and DMF (3.3 mL, 1.0 M). The flask was flushed with argon and fitted with a rubber septa and argon balloon. Ethyl bromoacetate (627 μL, 6.08 mmol, 1.10 equiv.) and triethylamine (1.54 mL, 11.0 mmol, 2.00 equiv.) were added by syringe. The mixture was stirred at room temperature for 10 hours, at which point the flask was heated to 80° C. and stirred for an additional 3 hours. The reaction was cooled to room temperature and concentrated by rotary evaporation. The residue was dissolved in dichloromethane (~1 mL), and a grey solid was precipitated by the addition of hexanes (~1 mL). The precipitate was collected by vacuum filtration to afford 7,8-dihydro-[1,3]dioxolo[4,5-g]quinoxalin-6(5H)-one as a grey solid (426 mg, 40% yield). $^1$H NMR (400 MHz, DMSO) b 10.00 (s, 1H), 6.39 (s, 1H), 6.36 (s, 1H), 5.82 (s, 2H), 5.65 (s, 1H), 3.58 (s, 2H).

3-ethoxy-4-iodo-N,N-dimethyl-aniline

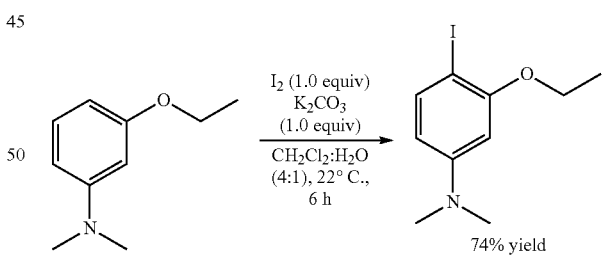

74% yield

To a flame dried 250-mL round bottomed flask equipped with a magnetic Teflon-coated stir bar and flushed with argon was added 3-ethoxy-N,N-dimethyl-aniline (1.10 g, 6.68 mmol, 1.00 equiv.) potassium carbonate (923 mg, 6.68 mmol, 1.00 equiv.), dichloromethane (170 mL) and water (40 mL). Iodine (1.70 g, 6.68 mmol, 1.00 equiv.) was added as a single portion and the mixture was stirred at room temperature for 6 h, at which time the mixture was poured into a 250 mL seperatory funnel, and saturated sodium thiosulfate (20 mL) was added. The organic layer was extracted, and the aqueous layer was extracted with dichloromethane (2×30 mL). The combined organic layers were dried over anhydrous sodium sulfate (Na$_2$SO$_4$), filtered, and concentrated via rotary evaporation. The crude residue was purified by column chromatography (toluene) to yield 3-ethoxy-4-iodo-N,N-dimethyl-aniline (1.44 g, 74% yield) as a grey solid. $^1$H NMR (400 MHz, CDCl$_3$) δ 7.51 (d, J=8.7 Hz, 1H), 6.20 (d, J=2.1 Hz, 1H), 6.13 (dd, J=8.7, 2.1 Hz, 1H), 4.07 (q, J=7.0 Hz, 2H), 2.94 (s, 6H), 1.47 (t, J=7.0 Hz, 3H).

Attempted Synthesis (1) of 8-(4-(dimethylamino)-2-ethoxyphenyl)-7,8-dihydro-[1,3]dioxolo[4,5-g]quinoxalin-6(5H)-one

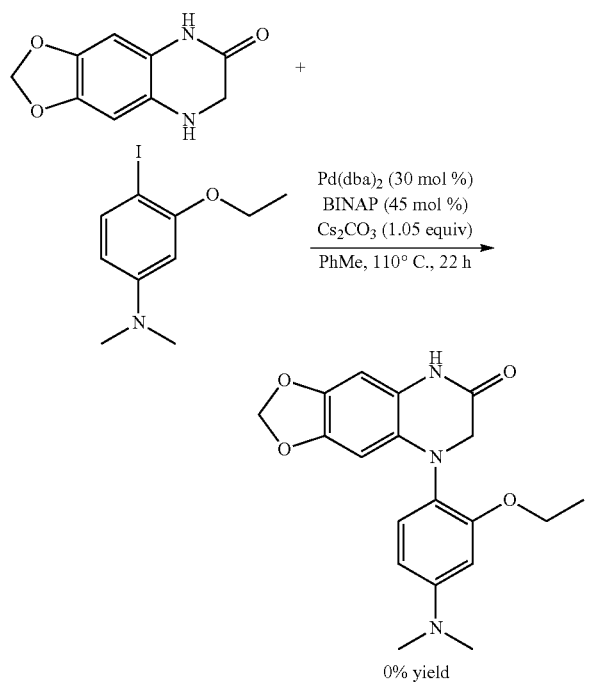

To a flame-dried reaction vial equipped with a magnetic Teflon-coated stir bar and flushed with argon was added 7,8-dihydro-5H-[1,3]dioxolo[4,5-g]quinoxalin-6-one (34.3 mg, 178 μmol, 1.20 equiv.), 3-ethoxy-4-iodo-N,N-dimethyl-aniline (43.3 mg, 148 μmol, 1.00 equiv.), rac-BINAP (8.4 mg, 13 μmol, 30 mol %), Pd$_2$dba$_3$ (8.2 mg, 9.0 μmol, 45 mol %), and cesium carbonate (50.9 mg, 156 μmol, 1.05 equiv.). The solids were suspended in toluene (0.30 mL, 0.5 M), the vial was flushed with argon, and sealed with a Teflon-backed crimp-cap. The reaction was heated to 110° C. and stirred for 18 hours. No consumption of starting materials was observed by TLC, and no evidence of product was observed by LCMS, and the reaction was not further purified.

Attempted Synthesis (2) of 8-(4-(dimethylamino)-2-ethoxyphenyl)-7,8-dihydro-[1,3]dioxolo[4,5-g]quinoxalin-6(5H)-one

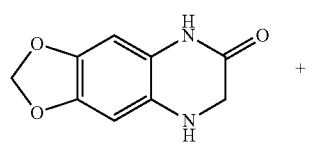

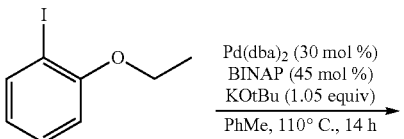

To a flame-dried 5-mL round bottomed flask equipped with a magnetic Teflon-coated stir bar and flushed with argon was added 7,8-dihydro-5H-[1,3]dioxolo[4,5-g]quinoxalin-6-one (96.1 mg, 0.500 mmol, 1.20 equiv.), 3-ethoxy-4-iodo-N,N-dimethyl-aniline (121 mg, 0.416 mmol, 1.00 equiv.), rac-BINAP (117 mg, 187 μmol, 30 mol %), Pd$_2$dba$_3$ (71.8 mg, 125 μmol, 45 mol %), and potassium tert-butoxide (49.1 mg, 437 μmol, 1.05 equiv.). The solids were suspended in toluene (0.83 mL, 0.5 M), the vial was flushed with argon, and sealed with a Teflon-backed crimp-cap. The reaction was heated to 110° C. and stirred for 18 hours. No consumption of starting materials was observed by TLC, and no evidence of desired product was observed by LCMS, and the reaction was not further purified.

Attempted Synthesis (3) of 8-(4-(dimethylamino)-2-ethoxyphenyl)-7,8-dihydro-[1,3]dioxolo[4,5-g]quinoxalin-6(5H)-one

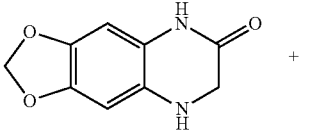

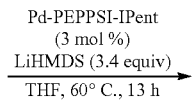

-continued

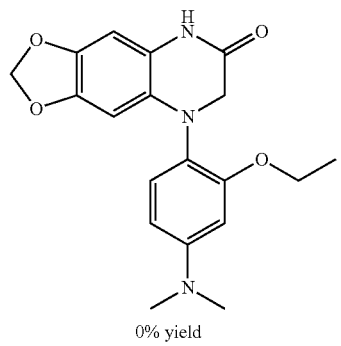

0% yield

To a flame-dried 5-mL round bottomed flask equipped with a magnetic Teflon-coated stir bar and flushed with argon was added 7,8-dihydro-5H-[1,3]dioxolo[4,5-g]quinoxalin-6-one (96.1 mg, 0.500 mmol, 1.00 equiv.), 3-ethoxy-4-iodo-N,N-dimethyl-aniline (145 mg, 0.500 mmol, 1.00 equiv.), and Pd-PEPPSI-iPent (11.9 mg, 15.0 µM, 3.0 mol %). The vial was sealed with a Teflon-backed crimp-cap and evacuated/backfilled 3× with argon. Lithium bis(trimethylsilyl)azanide (1 M in THF, 1.70 mL, 1.70 mmol, 3.40 equiv.) was added via syringe, and the vial was evacuated/backfilled 2× with argon. The vial was heated to 60° C. and stirred for 13 hours. Decomposition of starting materials was observed by TLC, no evidence of desired product was observed by LCMS, and the reaction was not further purified.

8-(4-(dimethylamino)-2-ethoxyphenyl)-7,8-dihydro-[1,3]dioxolo[4,5-g]quinoxalin-6(5H)-one

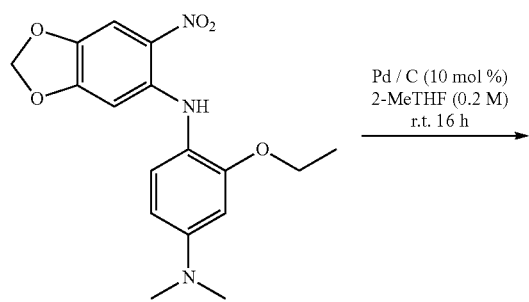

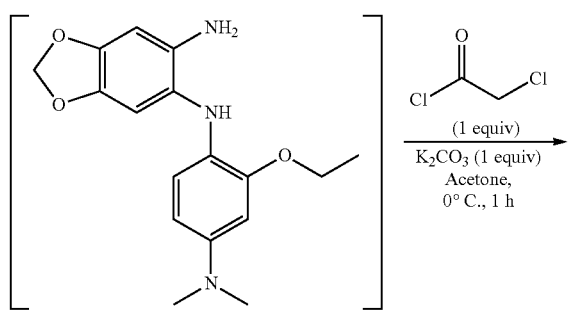

-continued

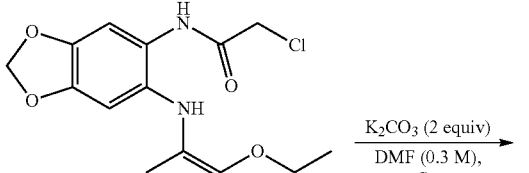

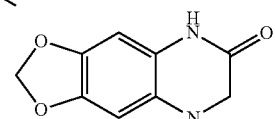

11% yield
3 steps

To a flame dried 25-mL round bottomed flask equipped with a magnetic Teflon-coated stir bar and flushed with argon was added N-(2-ethoxyphenyl)-6-nitrobenzo[d][1,3]dioxol-5-amine (345 mg, 1.0 mmol) and 2-MeTHF (5 mL, 0.2 M). Then, Pd/C (106 mg, 10 mol %, 10% Pd) was added to the flask, and the flask was fitted with a three-way T adapter. The flask was flushed with hydrogen gas during three vacuum/flush cycles. The reaction was left stirring at room temperature for 16 hours. The hydrogen balloon was removed for an argon balloon, and the flask was flushed with three vacuum/flush cycles, and the flask was cooled to 0° C. in an ice-water bath. Then, reagent grade acetone (5 mL, 0.2 M) was added, followed by vacuum-oven dried potassium carbonate (138 mg, 1.0 mmol, 1 equiv). Chloroacetyl chloride (0.08 mL, 1.0 mmol, 1.0 equiv) was added via syringe and the reaction was stirred at 0° C. for 0.5 hours. The reaction mixture was filtered through a pipet filled with Celite and concentrated. The crude mixture was dissolved in dry DMF (3.25 mL, 0.31 M), and transferred to an oven-dried 10-mL round bottomed flask flushed with argon. Vacuum-oven dried potassium carbonate (276 mg, 2 mmol, 2 equiv) was added, and the reaction was stirred at 100° C. for 1.5 hours. The reaction was poured into a separatory funnel that contained ice-cold water (10 mL). The aqueous phase was extracted with EtOAc (4×50 mL). The combined organic layers were washed with saturated aqueous sodium chloride (50 mL) and dried with anhydrous sodium sulfate ($Na_2SO_4$), filtered, and concentrated. The crude product was dry-loaded onto silica gel and purified via column chromatography (1:1 hexanes:ethyl acetate) to afford 8-(4-(dimethylamino)-2-ethoxyphenyl)-7,8-dihydro-[1,3]dioxolo[4,5-g]quinoxalin-6(5H)-one as a light brown solid (39 mg, 11% yield over 3 steps). $^1$H NMR (CDCl$_3$, 400 MHz) δ 8.93 (s, 1H), 7.00 (d, J=8.3 Hz, 1H), 6.40 (s, 1H), 6.33-6.26 (overlap, 2H), 5.94 (s, 1H), 5.78 (s, 2H), 4.15 (s, 2H), 4.03 (q, J=7.0 Hz, 2H), 2.97 (s, 6H), 1.29 (t, J=7.0 Hz, 3H).

7-bromo-2,3-dihydrobenzo[b][1,4]dioxine-6-carbaldehyde

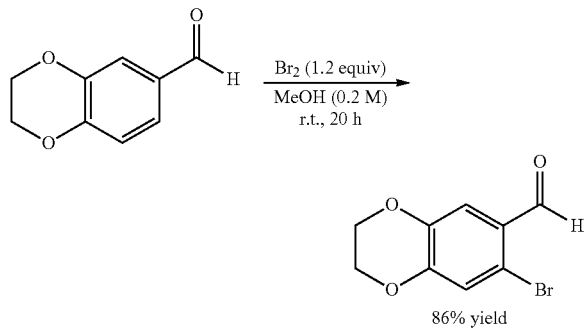

86% yield

To a 100-mL round bottomed flask equipped with a magnetic Teflon-coated stir bar and flushed with argon was added 2,3-dihydro-1,4-benzodioxine-6-carbaldehyde (2.00 g, 12.18 mmol) and methanol (60.2 mL, 0.2 M). Bromine (0.749 mL, 14.62 mmol, 1.2 equiv) was added via syringe as a single portion, and the mixture was stirred at room temperature for 20 hours. Water (100 mL) was added to the reaction mixture and an off-white precipitate formed. The solid was collect via vacuum filtration and rinsed with water (100 mL). The solid was dissolved in dichloromethane (100 mL) and dried with anhydrous sodium sulfate ($Na_2SO_4$), filtered, and concentrated to afford 7-bromo-2,3-dihydrobenzo[b][1,4]dioxine-6-carbaldehyde as a white powder (2.54 g, 86% yield) that required no further purification. $^1$H NMR ($CDCl_3$, 400 MHz) δ 10.17 (s, 1H), 7.47 (s, 1H), 7.13 (s, 1H), 4.32 (m, 2H), 4.28 (m, 2H).

6-bromo-7-nitro-2,3-dihydrobenzo[b][1,4]dioxine

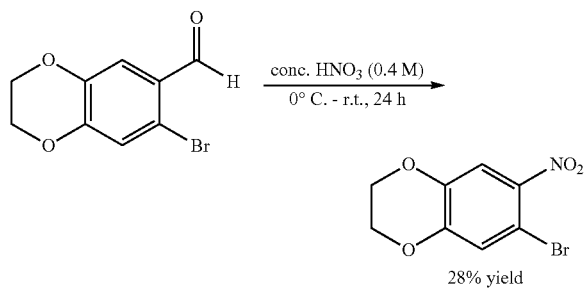

28% yield

To a 100-mL round bottomed flask quipped with a magnetic Teflon-coated stir bar was added conc. nitric acid (14 mL). With stirring, 7-bromo-2,3-dihydrobenzo[b][1,4]dioxine-6-carbaldehyde (1.33 g, 5.47 mmol) was added in small portions over 5 minutes. The reaction mixture was stirred at room temperature for 24 hours. Then, the mixture was poured into a 250-mL Erlenmeyer flask filled with water (25 mL) cooled in an ice-water bath, forming an off-white precipitate. The slurry was filtered via vacuum filtration and the solid was rinsed with water (50 mL). The solid was dissolved in dichloromethane (50 mL), dried with anhydrous sodium sulfate ($Na_2SO_4$), filtered, and concentrated via rotary evaporation. The crude product was dry-loaded onto silica gel and purified via column chromatography (gradient from hexanes to 7.5:1 hexanes:ethyl acetate to afford 6-bromo-7-nitro-2,3-dihydrobenzo[b][1,4]dioxine as a white solid (405 mg, 28% yield). $^1$H NMR ($CDCl_3$, 400 MHz) δ 7.59 (s, 1H), 7.21 (s, 1H), 4.33 (m, 2H), 4.30 (m, 2H).

2-ethoxy-N4,N4-dimethyl-N1-(7-nitro-2,3-dihydrobenzo[b][1,4]dioxin-6-yl)benzene-1,4-diamine

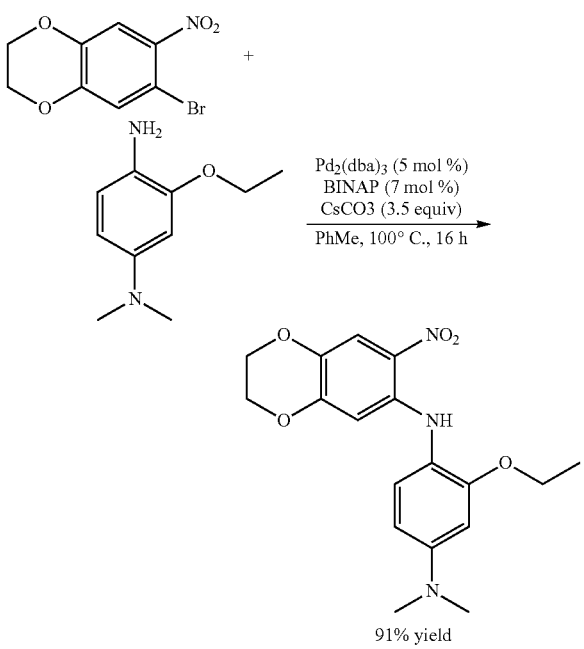

91% yield

To a flame-dried 25-mL round bottomed flask equipped with a magnetic Teflon-coated stir bar and flushed with argon was added 6-bromo-7-nitro-2,3-dihydrobenzo[b][1,4] dioxine (280 mg, 1.08 mmol) and dry toluene (3.60 mL, 0.3 M). $Pd_2(dba)_3$ (49 mg, 0.054 mmol, 5 mol %), rac-BINAP (46 mg, 0.075 mmol, 7 mol %), and cesium carbonate (1.23 g, 3.77 mmol, 3.5 equiv) were added, and the flask was flushed with argon. 3-ethoxy-N1,N1-dimethylbenzene-1,4-diamine (291 mg, 1.62 mmol, 1.5 equiv) was added and the reaction flask was fitted with a reflux condenser and allowed to stir at 100° C. overnight. The reaction mixture was cooled to room temperature, concentrated, then dry-loaded onto silica gel. The crude product was purified via column chromatography (gradient from hexanes to 3:1 hexanes: ethyl acetate) to 2-ethoxy-N4,N4-dimethyl-N1-(7-nitro-2,3-dihy drobenzo[b][1,4]dioxin-6-yl)benzene-1,4-diamine as a dark red solid (353 mg, 91% yield). $^1$H NMR ($CDCl_3$, 400 MHz) δ 9.25 (s, 1H), 7.75 (s, 1H), 7.14 (d, J=8.4 Hz, 1H), 6.47 (s, 1H), 6.35-6.29 (overlap, 2H), 4.27 (m, 2H), 4.20 (m, 2H), 4.04 (q, J=7.0 Hz, 2H), 2.97 (s, 6H), 1.35 (t, J=7.0 Hz, 3H).

9-(4-(dimethylamino)-2-ethoxyphenyl)-2,3,8,9-tetrahydro-[1,4]dioxino[2,3-g]quinoxalin-7(6H)-one

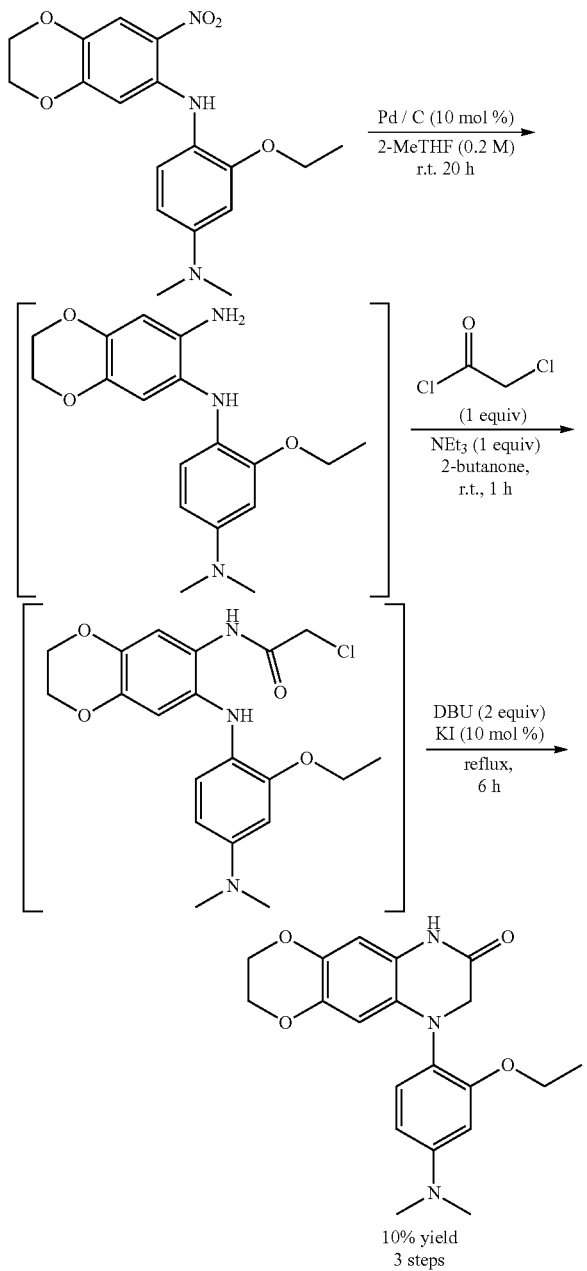

10% yield
3 steps

To a flame dried 25-mL round bottomed flask equipped with a Teflon-coated stir bar and flushed with argon was added 2-ethoxy-N4,N4-dimethyl-N1-(7-nitro-2,3-dihydrobenzo[b][1,4]dioxin-6-yl)benzene-1,4-diamine equipped with (390 mg, 1.09 mmol) and anhydrous THE (5 mL). Then, Pd/C (115 mg, 10 mol %, 10% Pd) was added to the flask, and the flask was fitted with a three-way T adapter. The flask was flushed with hydrogen gas during three vacuum/flush cycles. The reaction was left stirring at room temperature under hydrogen for 20 hours. The hydrogen balloon was replaced for an argon balloon, and the flask was flushed with three vacuum/flush cycles. Then, 2-butanone (5.0 mL) was added, followed by triethylamine (0.15 mL, 1.09 mmol, 1 equiv). Then, chloroacetyl chloride (0.086 mL, 1.09 mmol, 1.0 equiv) was added via syringe and the reaction was stirred at room temperature for 1 hour. DBU (0.327 mL, 2.18 mmol, 2 equiv), and KI (18 mg, 0.109 mmol, 10 mol %) were added to the reaction mixture, and the reaction was heated to 70° C. for 6 hours. The reaction mixture was filtered through Celite and the solids were rinsed with chloroform (50 mL). The filtrate was washed with water (25 mL), dried with anhydrous sodium sulfate ($Na_2SO_4$), filtered and concentrated via rotary evaporation. The crude product was purified by column chromatography (gradient from hexanes to 1:1 hexanes:ethyl acetate) to afford 9-(4-(dimethylamino)-2-ethoxyphenyl)-2,3,8,9-tetrahydro-[1,4]dioxino[2,3-g]quinoxalin-7(6H)-one as a brown-green solid (40 mg, 10% yield over three steps, ~80% purity). $^1$H NMR ($CDCl_3$, 400 MHz) δ 8.40 (s, 1H), 7.00 (d, J=8.3 Hz, 1H), 6.35-6.26 (overlap, 3H), 4.21-4.08 (overlap, 6H), 4.02 (q, J=7.0 Hz, 2H), 2.97 (s, 6H), 1.29 (t, J=7.0 Hz, 3H).

Activity Studies

FIGS. 1A-4 show results for growth inhibition of Huh7 cells upon contact with compounds (FQI-37Q), (FQI-34Q), (FQI-1Q), (JAK 196-22), and (JAK 196.23). Compounds (FQI-37Q) and (FQI-34Q) show high activities (GI50 about 0.5 μM and lower). Compound (FQI-1Q) show moderate activity (GI50=3.60 μM). Compounds (JAK 196-22) and (JAK 196.23) did not show measurable activity up to about 10 μM.

FIGS. 1A-1C illustrate the activity of compound (FQI-37Q). Three plots are shown showing the results in three trials. Growth inhibition of Huh7 cells show GI50 values of 0.186 μM, 0.251 μM and 0.380 μM.

FIG. 2 illustrates the activity of compound (FQI-34Q). Growth inhibition of Huh7 cells for (FQi-37Q) was measured as 0,501 μM.

FIGS. 3A and 3B illustrate the activity of compound (FQI-1Q). Two plots are shown for two trials with (FQI-1Q). Growth inhibition of Huh7 cells for (FQI-1Q) show GI50 values of 3.60 μM which is repeated.

Figure 4:
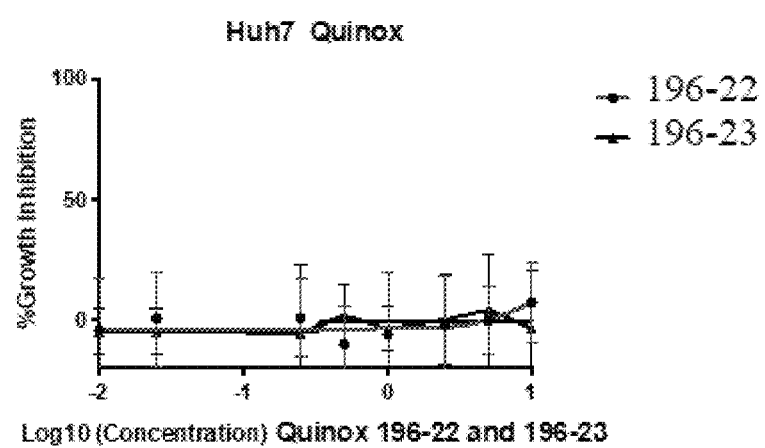

FIG. 4 illustrates the activity of compounds (JAK 196-22) and (JAK 196.23).

What is claimed is:
1. A compound of Formula (I):

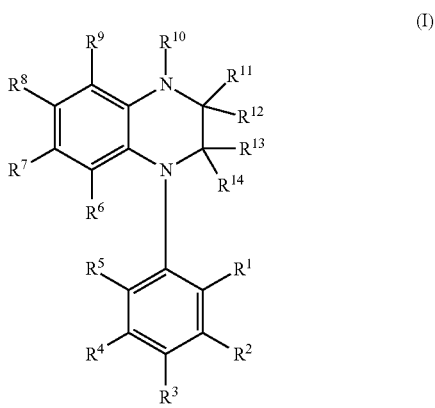

or enantiomers, derivatives, and pharmaceutically acceptable salts thereof; and none, one, or more vicinal pairs of $R^1$, $R^2$, $R^3$, $R^4$, $R^5$, $R^6$, $R^7$, $R^8$, and $R^9$ each, together with the carbons to which they are attached, form a 5-8 membered cycloalkyl or heterocyle ring; and the remaining $R^1$, $R^2$, $R^3$, $R^4$, $R^5$, $R^6$, $R^7$, or $R^9$ are each independently selected from the group consisting of hydrogen, halogen, $OR^{1A}$, $NR^{1A}R^{2A}$, $SR^{1A}$, $SO_2R^{1A}$, —$NO_2$, $C_1$-$C_6$ alkyl, $C_1$-$C_6$ haloalkyl, $C_1$-$C_6$ heteroalkyl, $C_2$-$C_8$alkenyl, aryl, and heteroaryl, and $R^8$ is selected from the group consisting of hydrogen, halogen, $OR^{1A}$, $NR^{1A}R^{2A}$, $SR^{1A}$, $SO_2R^{1A}$, $C_1$-$C_6$ alkyl, $C_1$-$C_6$ haloalkyl, $C_1$-$C_6$ heteroalkyl, $C_2$-$C_8$alkenyl and aryl;

$R^{10}$ is hydrogen, $C_1$-$C_6$ alkyl, $C_1$-$C_6$ haloalkyl, $C_1$-$C_6$ heteroalkyl, $C_2$-$C_8$alkenyl, aryl, heteroaryl, or halogen; or $R^{10}$ and one of the vicinal $R^{11}$ or $R^{12}$ groups together form a double bond between the carbon atoms they are attached to;

none or a vicinal pair of $R^{11}$, $R^{12}$, $R^{13}$ and $R^{14}$ together form a double bond between the carbon atoms they are attached to and the remaining $R^{11}$, $R^{12}$, $R^{13}$ and $R^{14}$ are each independently selected from the group consisting of hydrogen, halogen, $C_1$-$C_6$ alkyl, $C_1$-$C_6$ haloalkyl, $C_1$-$C_6$ heteroalkyl, $C_2$-$C_8$alkenyl, $OR^{3A}$, $SR^{3A}$, $SO_2R^{3A}$, $NR^{3A}R^{4A}$, heteroaryl, and aryl; or one or two of a germinal pair of $R^{11}$, $R^{12}$, $R^{13}$ and $R^{14}$ together form a carbonyl (=O) and the remaining $R^{11}$, $R^{12}$, $R^{13}$ and $R^{14}$ are each independently selected from the group consisting of hydrogen, halogen, $C_1$-$C_6$ alkyl, $C_1$-$C_6$ haloalkyl, $C_1$-$C_6$ heteroalkyl, $C_2$-$C_8$alkenyl, $OR^{3A}$, $SR^{3A}$, $SO_2R^{3A}$, $NR^{3A}R^{4A}$, halogen, heteroaryl, and aryl;

wherein, $R^{1A}$, $R^{2A}$, $R^{3A}$ and $R^{4A}$ are each independently selected from the group consisting of hydrogen, $C_1$-$C_8$ alkyl, $C_2$-$C_8$ alkenyl, $C_2$-$C_8$ alkynyl, cycloalkyl, heterocyclyl, $C_1$-$C_8$ haloalkyl, $C_1$-$C_8$ heteroalkyl, heteroaryl, and aryl, wherein the alkyl, alkenyl, alkynyl, cycloalkyl, heterocyclyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl or $C_1$-$C_6$ alkoxy, and any of the 5-8 membered cycloalkyl, the heterocycle ring, the alkyl, the haloalkyl, the heteroalkyl, the alkenyl, the heteroaryl, and the aryl can be optionally substituted with halogen, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono($C_1$-$C_6$ alkyl)amino or di($C_1$-$C_6$ alkyl)amino.

2. The compound according to claim 1, wherein at least one germinal pair of $R^{11}$, $R^{12}$, $R^{13}$ and $R^{14}$ together forms a carbonyl (=O).

3. The compound according to claim 1, wherein at least one vicinal pair of $R^{10}$ and $R^{12}$, or $R^{12}$ and $R^{14}$ together form a double bond between the carbon atoms they are attached to.

4. The compound according to claim 1, wherein $R^7$ and $R^8$ together with the carbons to which they are attached, form a 5-8 membered cycloalkyl or heterocycle ring.

5. The compound of claim 1, wherein the compound is of Formula (IA):

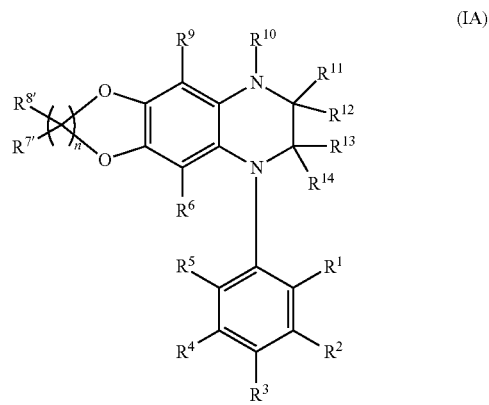

(IA)

wherein n is 1, 2 or 3; and $R^{7'}$ and $R^{8'}$ independently are hydrogen or halogen.

6. The compound of claim 5, wherein n is 1 or 2.

7. The compound of claim 5, wherein $R^{7'}$ is H or F.

8. The compound of claim 5, wherein $R^{8'}$ is H or F.

9. The compound of claim 1, wherein $R^6$ is hydrogen, halogen, $OR^{1A}$ $NR^{1A}R^{2A}$, $SR^{1A}$, or $C_1$-$C_6$ alkyl.

10. The compound of claim 9, wherein $R^6$ is hydrogen, halogen or $OR^{1A}$.

11. The compound of claim 1, wherein $R^9$ is hydrogen, halogen, $OR^{1A}$, $NR^{1A}R^{2A}$, $SR^{1A}$, or $C_1$-$C_6$ alkyl.

12. The compound of claim 11, wherein $R^9$ is hydrogen, halogen or $OR^{1A}$.

13. The compound of claim 1, wherein $R^{10}$ is hydrogen or $C_1$-$C_6$ alkyl.

14. The compound of claim 1, wherein $R^1$ is hydrogen, halogen, $OR^{1A}$, $NR^{1A}$, $R^{2A}$, $SR^{1A}$, $C_1$-$C_6$alkyl or —$NO_2$.

15. The compound of claim 14, wherein $R^1$ is O($C_1$-$C_6$ alkyl).

16. The compound of claim 1, wherein $R^2$ is hydrogen, halogen, $OR^{1A}$, $NR^{1A}R^{2A}$, $SR^{1A}$, $C_1$-$C_6$alkyl or —$NO_2$.

17. The compound of claim 16, wherein $R^2$ is hydrogen or halogen.

18. The compound of claim 1, wherein $R^3$ is hydrogen, halogen, $OR^{1A}$, $NR^{1A}R^{2A}$, $C_1$-$C_6$alkyl, $C_2$-$C_8$alkenyl, $C_1$-$C_6$ haloalkyl, or —$NO_2$.

19. The compound of claim 18, wherein $R^3$ is N($C_1$-$C_6$ alkyl)$_2$, halogen, $C_1$-$C_6$ haloalkyl, or —$NO_2$.

20. The compound of claim 1, wherein $R^4$ is hydrogen, halogen, $OR^{1A}$, $NR^{1A}R^{2A}$, $SR^{1A}$, $C_1$-$C_6$alkyl or —$NO_2$.

21. The compound of claim 20, wherein $R^4$ is hydrogen or halogen.

22. The compound of claim 1, wherein $R^5$ is hydrogen, halogen, $OR^{14}$, $NR^{14}R^{24}$, $SR^{14}$, $C_1$-$C_6$alkyl or —$NO_2$.

23. The compound of claim 22, wherein $R^5$ is hydrogen or halogen.

24. The compound of claim 1, wherein $R^1$ is $O(C_1$-$C_6$ alkyl) and $R^3$ is $N(C_1$-$C_6$ alkyl)$_2$.

25. The compound of claim 1, wherein $R^2$, $R^4$ and $R^5$ are hydrogen.

26. The compound of claim 1, wherein $R^{11}$ and $R^{12}$, or $R^{13}$ and $R^{14}$ are hydrogen.

27. The compound of claim 1, wherein the compound is

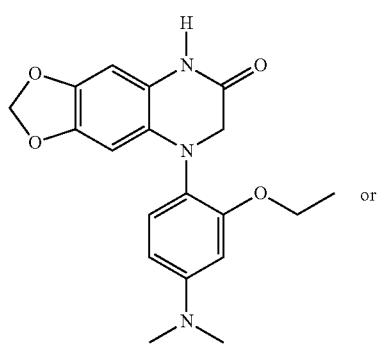

(FQI-34Q)

or

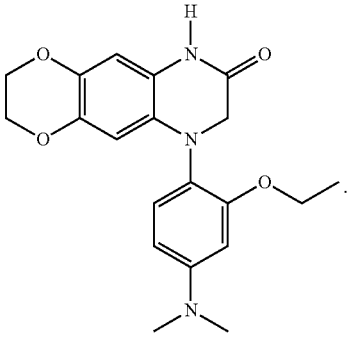

(FQI-37Q)

28. A pharmaceutical composition comprising a compound of claim 1 and a pharmaceutically acceptable excipient or carrier.

29. A method for inhibiting LSF in a subject, the method comprising administering an effective amount of a compound of claim 1 to a subject in need thereof.

30. A method for treating cancer in a subject, the method comprising administering an effective amount of a compound of claim 1 to a subject in need thereof.

* * * * *